US005562903A

United States Patent [19]
Co et al.

[11] Patent Number: 5,562,903
[45] Date of Patent: Oct. 8, 1996

[54] HUMANIZED ANTIBODIES THAT RECOGNIZE DIFUCOSYL LEWIS BLOOD GROUP ANTIGENS Y-6 AND B-7-2

[75] Inventors: Man S. Co, Cupertino, Calif.; Hans Loibner, Vienna, Austria

[73] Assignee: Sandoz Ltd., Basel, Switzerland

[21] Appl. No.: 53,171

[22] Filed: Apr. 22, 1993

Related U.S. Application Data

[63] Continuation of Ser. No. 932,180, Aug. 19, 1992, abandoned.

[30] Foreign Application Priority Data

Aug. 21, 1991 [GB] United Kingdom ............ 9118013
Mar. 2, 1992 [GB] United Kingdom ............ 9204514

[51] Int. Cl.$^6$ ............ A61K 39/395; C07K 16/28
[52] U.S. Cl. ............ 424/133.1; 530/387.3; 530/387.5; 530/388.85; 424/137.1; 424/155.1
[58] Field of Search ............ 530/387.3, 387.5, 530/388.85; 435/240.27; 424/133.1, 137.1, 155.1

[56] References Cited

FOREIGN PATENT DOCUMENTS

| 0125023 | 11/1984 | European Pat. Off. . |
|---|---|---|
| 0239400 | 9/1987 | European Pat. Off. . |
| 0285059 | 10/1988 | European Pat. Off. . |
| 0445078 | 4/1991 | European Pat. Off. . |
| 8601533 | 3/1986 | WIPO . |
| 9007861 | 7/1990 | WIPO . |
| 9109967 | 7/1991 | WIPO . |
| 9203165 | 5/1992 | WIPO . |

OTHER PUBLICATIONS

Kabat, "Sequences of Proteins of Immunological Interest," 1987, USDHHS, pp. 50, 167.
Fahey et al. Clin Exp. Immunol. 88: 1–5, 1992.
Waldman,. Science 252:1657–1662, 1991.
Wawrzynczak et al. Clin, Exp. Immunol. 82:189–193, 1990.
Kimmel et al., J. Neurosurg. 66:161–171, 1987.
Schlom, in "Molecular Foundations of Oncology," S. Broder, Ed., Williams & Wilkins, 1991, pp. 95–134.
Riechmann et al, Nature, vol. 33224, pp. 323–327 (1988).
Queen et al, Pro. Nat. Acad. Sci. USA, vol. 86, pp. 10029–10033 (Dec. 1989).

*Primary Examiner*—Paula K. Hutzell
*Attorney, Agent, or Firm*—Townsend and Townsend and Crew LLP

[57] ABSTRACT

Humanized monoclonal antibodies that recognize the difucosyl Lewis blood group antigens Y-6 and B-7-2 are disclosed. The antibodies have a humanized light chain variable region and a humanized heavy chain variable region with CDRs from antibody BR55-2. Fragments of the antibodies and pharmaceutical compositions containing them are also disclosed.

12 Claims, 42 Drawing Sheets a) mc45 5' TATATCTAGAATTCCCCCCCCCCCCCCCCC 3' b) mc46 5' TATAGAGCTCAAGCTTGGATGGTGGGAAGATGGATACAGTTGGTGC 3' c) mc47 5' TATAGAGCTCAAGCTTCCAGTGGATAGAC(CAT)GATGGGG(GC)TGT(TC)GTTTTGGC 3'

FIG. 2

```
             10         20         30         40         50         60
   ATCAGTCTCCTCAGGCTGTCTCCTCAGGTTGCCTCCTCAAAATGAAGTTGCCTGTTAGGC
                                              M  K  L  P  V  R 70         80         90        100        110        120
   TGTTGGTGCTGATGTTCTGGATTCCTGCTTCCAGCAGTGATGTTTTGATGACCCAAACTC
    L  L  V  L  M  F  W  I  P  A  S  S  S  D  V  L  M  T  Q  T 130        140        150        160        170        180
   CACTCTCCCTGCCTGTCAGTCTTGGAGATCAAGCCTCCATCTCTTGCAGATCTAGTCAGA
    P  L  S  L  P  V  S  L  G  D  Q  A  S  I  S  C  R  S  S  Q 190        200        210        220        230        240
   GCATTGTACATAGTAATGGAAACACCTATTTAGAATGGTACCTGCAGAAACCAGGCCAGT
    S  I  V  H  S  N  G  N  T  Y  L  E  W  Y  L  Q  K  P  G  Q
              CDR1

250        260        270        280        290        300
   CTCCAAAGCTCCTGATCTCCAAAGTTTCCAACCGATTTTCTGGGGTCCCAGACAGGTTCA
    S  P  K  L  L  I  S  K  V  S  N  R  F  S  G  V  P  D  R  F
                          CDR2

310        320        330        340        350        360
   GTGGCAGTGGATCAGGGACAGATTTCACACTCAAGATCAGCAGAGTGGAGGCTGAGGATC
    S  G  S  G  S  G  T  D  F  T  L  K  I  S  R  V  E  A  E  D 370        380        390        400        410        420
   TGGGAGTTTATTACTGCTTTCAAGGTTCACATGTTCCATTCACGTTCGGCTCGGGGACAA
    L  G  V  Y  Y  C  F  Q  G  S  H  V  P  F  T  F  G  S  G  T
                     CDR3

430
   AGTTGGAAATAAAA
    K  L  E  I  K
```

FIG. 3

```
         10        20        30        40        50        60
TTGACAGAGGAGGCCAGTCTGGATTCGATTCCCAGTTCCTCACATTCAGTGATCAGCACT 70        80        90       100       110       120
GAACACGGACCCTCACCATGAACTTGGGGCTCAGCTTGATTTTCCTTGTCCTTGTTTTAA
                  M  N  L  G  L  S  L  I  F  L  V  L  V  L 130       140       150       160       170       180
AAGGTGTCCAGTGTGAAGTGAAGCTGGTGGAGTCTGGGGGAGGCTTAGTGCAGCCTGGAG
 K  G  V  Q  C  E  V  K  L  V  E  S  G  G  G  L  V  Q  P  G 190       200       210       220       230       240
GGTCCCTGAAACTCTCCTGTGCAACCTCTGGATTCACTTTCAGTGACTATTACATGTATT
 G  S  L  K  L  S  C  A  T  S  G  F  T  F  S  D  Y  Y  M  Y
                                                 ─────────────
                                                     CDR1

250       260       270       280       290       300
GGGTTCGCCAGACTCCAGAGAAGAGGCTGGAGTGGGTCGCATACATTAGTAATGGTGGTG
 W  V  R  Q  T  P  E  K  R  L  E  W  V  A  Y  I  S  N  G  G
                                             ─────────────────

310       320       330       340       350       360
GTAGTAGCCATTATGTAGACAGTGTAAAGGGCCGATTCACCATCTCCAGAGACAATGCCA
 G  S  S  H  Y  V  D  S  V  K  G  R  F  T  I  S  R  D  N  A
 ─────────────────────────────
            CDR2

370       380       390       400       410       420
AGAACACCCTGTACCTGCAAATGAGCCGTCTGAGGTCTGAGGACACAGCCATGTATCACT
 K  N  T  L  Y  L  Q  M  S  R  L  R  S  E  D  T  A  M  Y  H 430       440       450       460       470       480
GCGCAAGGGGGATGGATTACGGGGCCTGGTTTGCTTACTGGGGCCAGGGGACTCTGGTCA
 C  A  R  G  M  D  Y  G  A  W  F  A  Y  W  G  Q  G  T  L  V
          ──────────────────────────
                   CDR3

490
CTGTCTCTGCA
 T  V  S  A
```

FIG. 4

```
         10         20         30         40         50         60
TCTAGACCACCATGAAGTTGCCTGTTAGGCTGTTGGTGCTGATGTTCTGGATTCCTGCTT
          M  K  L  P  V  R  L  L  V  L  M  F  W  I  P  A 70         80         90        100        110        120
CCAGCAGTGATGTTTTGATGACCCAAACTCCACTCTCCCTGCCTGTCAGTCTTGGAGATC
 S  S  S  D  V  L  M  T  Q  T  P  L  S  L  P  V  S  L  G  D 130        140        150        160        170        180
AAGCCTCCATCTCTTGCAGATCTAGTCAGAGCATTGTACATAGTAATGGAAACACCTATT
 Q  A  S  I  S  C  R  S  S  Q  S  I  V  H  S  N  G  N  T  Y 190        200        210        220        230        240
TAGAATGGTACCTGCAGAAACCAGGCCAGTCTCCAAAGCTCCTGATCTCCAAAGTTTCCA
 L  E  W  Y  L  Q  K  P  G  Q  S  P  K  L  L  I  S  K  V  S 250        260        270        280        290        300
ACCGATTTTCTGGGGTCCCAGACAGGTTCAGTGGCAGTGGATCAGGGACAGATTTCACAC
 N  R  F  S  G  V  P  D  R  F  S  G  S  G  S  G  T  D  F  T 310        320        330        340        350        360
TCAAGATCAGCAGAGTGGAGGCTGAGGATCTGGGAGTTTATTACTGCTTTCAAGGTTCAC
 L  K  I  S  R  V  E  A  E  D  L  G  V  Y  Y  C  F  Q  G  S 370        380        390        400        410        420
ATGTTCCATTCACGTTCGGCTCGGGGACAAAGTTGGAAATAAAACGTAAGTAGACTTTTG
 H  V  P  F  T  F  G  S  G  T  K  L  E  I  K
```

CTCTAGA

FIG. 8

```
         10         20         30         40         50         60
TCTAGACCACCATGAACTTGGGGCTCAGCTTGATTTTCCTTGTCCTTGTTTTAAAAGGTG
             M  N  L  G  L  S  L  I  F  L  V  L  V  L  K  G 70         80         90        100        110        120
TCCAGTGTGAAGTGAAGCTGGTGGAGTCTGGGGGAGGCTTAGTGCAGCCTGGAGGGTCCC
 V  Q  C  E  V  K  L  V  E  S  G  G  G  L  V  Q  P  G  G  S 130        140        150        160        170        180
TGAAACTCTCCTGTGCAACCTCTGGATTCACTTTCAGTGACTATTACATGTATTGGGTTC
 L  K  L  S  C  A  T  S  G  F  T  F  S  D  Y  Y  M  Y  W  V 190        200        210        220        230        240
GCCAGACTCCAGAGAAGAGGCTGGAGTGGGTCGCATACATTAGTAATGGTGGTGGTAGTA
 R  Q  T  P  E  K  R  L  E  W  V  A  Y  I  S  N  G  G  G  S 250        260        270        280        290        300
GCCATTATGTAGACAGTGTAAAGGGCCGATTCACCATCTCCAGAGACAATGCCAAGAACA
 S  H  Y  V  D  S  V  K  G  R  F  T  I  S  R  D  N  A  K  N 310        320        330        340        350        360
CCCTGTACCTGCAAATGAGCCGTCTGAGGTCTGAGGACACAGCCATGTATCACTGCGCAA
 T  L  Y  L  Q  M  S  R  L  R  S  E  D  T  A  M  Y  H  C  A 370        380        390        400        410        420
GGGGGATGGATTACGGGGCCTGGTTTGCTTACTGGGGCCAGGGGACTCTGGTCACTGTCT
 R  G  M  D  Y  G  A  W  F  A  Y  W  G  Q  G  T  L  V  T  V

↓ 430        440
CTGCAGGTGAGTCCTAACTTCTAGA
 S  A
```

FIG. 9

```
                    10         20         30         40         50
H-hu-BR55-2/1:  EVQLLESGGG LVQPGGSLRL SCAASGFTFS DYYMYWVRQA PGKGLEWVAY
or H-hu-BR55-2/2:                                          E R
or H-hu-BR55-2/3:                                          E R 60         70         80         90        100
             ISNGGGSSHY VDSVKGRFTI SRDNSKNTLY LQMNSLRAED TALYYCARGM
                                                                H
                                   A                            H 110        119
             DYGAWFAYWG QGTLVTVSS
```

```
           10         20         30         40         50         60
    TATATCTAGA CCACCATGAA GTTGCCTGTT AGGCTGTTGG TGCTGATGTT CTGGATTCCT 70         80         90        100
    GCTTCCAGCA GTGATATTGT GATGACCCAA TCTCCACTCT CCCTGCCT
``` jb 38

```
           10         20         30         40         50         60
    TATAGGTACC ATTCTAAATA GGTGTTTCCA TTACTATGTA CAATGCTCTG ACTAGACCTG 70         80         90        100
    CAAGAGATGG AGGCTGGCTC TCCAGGAGTG ACAGGCAGGG AGAGTGGA
``` jb 39

```
           10         20         30         40         50         60
    TATAGGTACC TTCAGAAACC AGGCCAGTCT CCACAGCTCC TGATCTCCAA AGTTTCCAAC 70         80         90        100        110        120
    CGATTTTCTG GGGTCCCAGA CAGGTTCAGT GGCAGTGGAT CAGGGACAGA TTTCACACTC

130
    AAGATCAGCA GAG
``` jb 40

```
           10         20         30         40         50         60
    TATATCTAGA GCAAAAGTCT ACTTACGTTT TATTTCCAAC TTTGTCCCCT GGCCGAACGT 70         80         90        100        110        120
    GAATGGAACA TGTGAACCTT GAAAGCAGTA ATAAACTCCC ACATCCTCAG CCTCCACTCT

130
    GCTGATCTTG AG
```

FIG. 14

```
              10         20         30         40         50         60
         TATATCTAGA CCACCATGAA CTTCGGGCTA AGCTTGATTT TCCTTGTCCT TGTTTTAAAA 70         80         90        100        110        120
         GGTGTCCAGT GTGAAGTGCA ACTGCTGGAG TCTGGGGGAG GCTTAGTGCA GCCTGGAGGA

130
         AGTCTACGAC TC
``` mc 109

```
              10         20         30         40         50         60
         TATAGAGCTC CCACCACCGT TGCTAATGTA TGCGACCCAC TCCAGCCTCT TTTCTGGAGC 70         80         90        100        110        120
         CTGGCGAACC CAGTACATGT AATAATCACT GAAAGTGAAT CCAGAGGCTG CACAGGAGAG

130
         TCGTAGACTT CCT
``` mc 110

```
              10         20         30         40         50         60
         TATAGAGCTC ACATTACGTA GATTCGGTCA AGGGCCGATT CACCATCTCC AGAGATAATG 70         80         90        100        110
         CCAAGAACAC CCTGTACCTG CAGATGAACT CACTGCGAGC TGAGGACACG GCCTTATA
``` mc 111

```
              10         20         30         40         50         60
         TATATCTAGA AAAAAGCCAG CTTACCTGAG GAGACGGTGA CCAGGGTCCC TTGGCCCCAG 70         80         90        100        110
         TATGCGAACC ATGCCCCGTA GTCCATCCCT CTTGCACAGT GATATAAGGC CGTGTCCT
```

HUMANIZED ANTIBODIES THAT RECOGNIZE DIFUCOSYL LEWIS BLOOD GROUP ANTIGENS Y-6 AND B-7-2

This is a continuation of application Ser. No. 07/932,180, filed Aug. 19, 1992, now abandoned.

The use of monoclonal antibodies (=Mabs) in therapeutic applications is gaining increasing acceptance. One such group of Mabs, of murine origin, is BR55-2 and fragments thereof having the same specificity and their variants, disclosed in e.g. Wistar EP 285 059, M. Blaszcyk-Thurin et al, *J. Biol. Chem.* 262 (1987)/372–379, or Z. Steplewsky et al, *Hybridoma* 9(1990) 201–210. These publications also disclose their preparation and their use in the detection and therapy of, basically, cancer of epithelial origin. The BR55-2 class of antibodies recognizes the difucosyl Lewis blood group antigens Y-6 and B-7-2 normally associated with cancer of epithelial origin. Mabs with specificity of BR55-2 are also useful for immunotherapy of HIV-infections, since the Lewis Y antigen is also selectively expressed on HIV infected cells.

There are, however, several drawbacks in using murine Mabs for therapeutic purposes in humans. First, such antibodies can induce a human anti-mouse antibody response; second, the half life of murine Mabs in the circulation is relatively short compared to human immunoglobulin; third, the Fc portion of murine Mabs may not elicit ADCC or CDC as effectively as the Fc portion of a human antibody. To overcome these possible problems recombinant DNA technologies have been applied to develop Mabs in which a part of the original mouse components are substituted by analogous human components. One such approch are human/mouse chimeric Mabs, containing the variable region of the murine antibody and the constant region of human immunoglobulin heavy and light chains. A further developement in this direction consists in the construction of "fully humanized" antibodies by recombinant DNA technology in which only the minimum necessary parts of the parent mouse antibody, the complementarity determining regions (CDRs), are combined with human variable region frameworks and human constant regions, For the design and construction of these "fully humanized" Mabs, sequence homology and molecular modelling may be used to select a combination of mouse and human sequence elements that would further reduce immunogenicity while retaining the binding properties.

One embodiment of this invention concerns human/mouse chimeric Mabs recognizing the difucosyl Lewis blood group antigens Y-6 and B-7-2. A further embodiment of this invention concerns "fully humanized" monoclonal antibodies recognizing the difucosyl Lewis blood group antigens Y-6 and B-7-2. More particularly it concerns monoclonal antibodies containing only the minimum necessary parts of the parent mouse antibody BR55-2. It concerns also processes for the production of these antibodies and their use as pharmaceuticals.

A first step of the development of these new Mabs, the cloning and sequencing of the heavy chain and light chain variable domain cDNA for the murine Mab IgG3 BR55-2, can be carried out in the following manner:

The variable domain cDNA for the heavy chain and light chain of murine Mab BR55-2 was cloned by the anchored PCR method (Chiang Y. L., Sheng-Dong R., Brown A. and Larrick J. W.: *Bio Techniques* 7, 360–366 [1989]). which is outlined in FIG. 1. First, a total RNA preparation was prepared using the hot phenol method. Briefly, 1×10$^7$ Mab BR55-2 hybridoma cells (ATCC HB9324) were resuspended in 1.2 ml of RNA extraction buffer (50 mM sodium acetate, pH 5.2, 1% SDS), vortexed and incubated with 0.6 ml of phenol, pH 5.2, at 65° C. for 15 minutes, followed by another 15 minutes incubation on ice, The extract was spun in a microfuge; the aqueous phase was recovered and ethanol precipitated twice. The RNA pellet was resuspended in water and quantitated at $OD_{260}$. cDNA was synthesized from the total RNA using reverse transcriptase (5 µg total RNA, 40 ng $dT_{12-18}$ (Pharmacia), 200 units of M-MLV reverse transcriptase (BRL), 40 units of RNAsin (Pomega), 50 mM Tris-HCl, pH 8.3, 75 mM KCl, 10 mM DTT, 3 mM $MgCl_2$ and 0.5 mM each dNTP in a 20 µl reaction volume). The G-tailing was achieved with terminal deoxynucleotidyl transferase (TdT) (cDNA, 15 units TdT (BRL), 0.1M potassium cacodylate, pH 7.2, 2 mM $CoCl_2$, 0.2 mM DTT and 1 mM dGTP in a 20 µl reaction volume). Under the conditions described, tails generally contained about 20 bases. One half of the G-tailed product was then amplified to generate the $V_L$ gene and the other half amplified to provide the $V_H$ gene using Taq polymerase. The $V_L$ gene is amplified with the primer mc45 (sequence shown in FIG. 2a), that anneals to the G tail, and a primer mc46 (FIG. 2b) that anneals to the constant region of the kappa light chain. The $V_H$ gene was amplified with primers mc45 (FIG. 2a) and mc47 (FIG. 2c) that anneals to the constant region of gamma chains. EcoRI and HindIII sites are included in the upstream and downstream primers for convenient subcloning into pUC18 vector. An alternate set of restriction sites (XbaI and SacI) are also included in the primers for the rare event that EcoRI and HindIII sites are present in the variable region genes. The PCR reactions were performed in a programmable heating block using 30 rounds of temperature cycling (92° C. for 1 minute, 50° C. for 2 minutes and 72° C. for 3 minutes). The reaction included the G-tailed product, 1 µg of each primer and 2.5 units of Taq polymerase (Perkin Elmer Cetus) in a final volume of 100 µl, with the reaction buffer recommended by the manufacturer. The PCR product bands were excised from a low-melting agarose gel, digested with restriction enzymes and cloned into pUC18 vector for sequence determination. The nucleotide sequence and the translated amino acid sequence of the light chain and heavy chain variable domain is shown in FIGS. 3 and 4. The initiation codon is underlined. The first amino acid of the mature protein is marked 1, Complementarity determining regions (CDRs) are underlined and labeled.

The generation of the human/mouse chimeric Mabs can be carried out in the following manner:

1. Construction of Expression Vectors

Separate expression vectors were used to express the chimeric human BR55-2 IgG1 and IgG3 antibody light and heavy chains: pVk for the light chain, pVg1 for the gamma 1 heavy chain and pVg3 for the gamma 3 heavy chain. Diagrams of these vectors, with relevant restriction sites indicated, are presented in FIGS. 5 to 7. First pVk and then pVg1 and pVg3 are described in detail below; nucleotide position numbers start with 1 at the EcoRI site and refer to the complete plasmids.

Plasmid pVk

Proceeding clockwise (FIG. 5), pVk first contains the human cytomegalovirus (CMV) major immediate early (IE) enhancer and promoter (Boshart M. et al., *Cell* 41, 521–520 [1985]). The function of the promoter is to initiate transcription of the light chain gene at nucleotide 536, and the function of the enhancer, extending over approximately nucleotides 12 to 418, is to strongly increase the level of transcription (Boshart M. et al., *Cell* 41, 521–520 [1985]). Thus the part of human CMV used is regulatory; no proteins are encoded. The CMV region is preceded by a short oligonucleotide linker used to connect it to the EcoRI site of the preceding pBR322 fragment.

The CMV region is followed by another linker containing an XbaI site. The variable region of an antibody light chain gene such as BR55-2 may be cloned into the XbaI site. The XbaI site is followed by part of a genomic clone (Hieter P. A. et al.: *Cell* 22, 197–207 [1985]) of the human kappa light chain constant region ($C_L$), including the coding sequence, polyadenylation (poly A) signal, and part of the preceding intron.

The $C_L$ region is followed by a gene encoding xanthine guanine phosphoribosyl transferase (gpt), together with regulatory elements (enhancer, promoter, splice signals, poly A signal) from Simian Virus 40 (SV40) needed for transcription. The function of this region, which was taken as a unit from the plasmid pSV2-gpt (Mulligan R. C. & Berg P.: *Proc. Natl. Acad. Sci. USA* 78, 2072–2076 [1981]), is to provide a selectable drug-resistance marker after transfection of pVk into mammalian cells. Moving counter-clockwise within this one unit, first there is an SV40 segment containing the SV40 enhancer and early promoter (Reddy V. B. et al.: *Science* 200, 494–502 [1978]), to ensure strong transcription initiation. This segment is followed by the coding sequence of the *E. coli* gpt gene (Richardson K. K. et al.: *Nucleic Acids Research* 11, 8809–8816 [1983]). The gpt gene is followed by an SV40 segment containing the small t antigen intron, believed to increase mRNA levels, and then another SV40 segment containing a poly A signal for ending the mRNA transcript. The direction of transcription of the gpt gene is opposite to that of the kappa light chain gene.

Finally, pVk contains a large part of the widely used *E. coli* vector plasmid pBR322 (Sutcliffe J. G.: *Cold Spring Harbor Symp. Quant. Biol.* 43, 77–90 [1979]), comprising the origin of replication and ampicillin resistance gene (amp), respectively used for growth and selection in *E. coli*. These procaryotic elements are expected to be non-functional after pVk is transfected into mammalian cells.

Plasmid pVg1$^c$. This plasmid is similar to pVk but contains a heavy chain instead of light chain constant region and a different selectable marker. Specifically, proceeding clockwise (FIG. 6), pVg1 contains the same CMV enhancer and promoter for strong transcription initiation as pVk, inserted with the same EcoRI and XbaI linkers, The variable region of an antibody heavy chain such as BR55-2 can be inserted at the XbaI site. That site is followed by part of a genomic clone (Ellison J. W. et al.: *Nucleic Acids Research* 10, 4071–4079 [1979]), containing the human gamma 1 heavy chain constant region ($C_H$) including the $C_H1$, hinge (H), $C_H2$ and $C_H3$ exons with the intervening introns, part of the intron preceding $C_H1$, and a poly A site following $C_H3$.

The $C_H$ region is followed by a gene encoding hygromycin B phosphotransferase (hyg), together with regulatory elements (enhancer, promoter, splice signals, poly A signal) from SV40 needed for transcription. This unit is identical to the gpt unit in pVk, except that hyg replaces gpt. The hyg gene (Gritz L. & Davies J.: *Gene* 25, 179–188 [1983]) was cloned from an *E. coli* plasmid and confers resistance to the antibiotic hygromycin B, so it can be used as a selectable marker after transfection into mammalian cells. Finally, pVg1 contains the same part of the plasmid pBR322 as pVk, containing the origin of replication and amp gene for use in *E. coli*.

Plasmid pVg3$^c$. This plasmid is identical to pVg1$^c$ except that the XbaI-BamHI fragment containing the human gamma 1 heavy chain constant region is replaced by a XbaI-BamHI fragment containing the human gamma 3 heavy chain constant region (FIG. 7), including the $C_H1$, hinge (H), $C_H2$ and $C_H3$ exons with the intervening introns, part of the intron preceding $C_H1$, and a poly A site following $C_H3$ (Takahashi N. et al.: *Cell* 29, 671–679 [1982]). The gamma 3 hinge region differs from the gamma 1 hinge region in that the former is comprised of 4 exons separated by 3 introns.

Both pVk, pVg1$^c$ and pVg3$^c$ were constructed from their component parts in a number of steps by standard methods (Sambrook J. et al.: *Molecular Cloning, A Laboratory Manual*, 2$^{nd}$ ed., Cold Spring Harbor Laboratory Press, N.Y. [1989]), including synthesis of oligonucleotide linkers. Their structure was carefully verified during and after construction by restriction mapping and sequencing.

2. Construction of Variable Domain Segments

Chimeric BR55-2 light chain.

The actual expressed chimeric BR55-2 light chain gene consists of two adjacent parts: a human genomic kappa constant region built into the vector pVk (see above), and the murine light chain variable region ($V_L$) constructed by PCR. To generate the $V_L$ XbaI fragment, primers were constructed to anneal to the 5' and 3' ends of the murine cDNA clone. The 5' primer was constructed to include an XbaI site and a consensus CCACC sequence followed by the first ATG codon and 15 nucleotides of the signal peptide sequence. The 3' primer included the last 15 nucleotides of the variable region gene, followed by 23 nucleotides which are the same as the sequence that follows $J_K4$ in the mouse genomic sequence. The primer also includes an XbaI site. The PCR generated fragment was then digested with XbaI and cloned into the XbaI site in the pVk vector. Thus, the cloned segment (FIG. 8) encodes the $V_L$ domain, including the J segment and a typical immunoglobulin leader (signal) peptide, which is cleaved off as the light chain is secreted. In addition, the segment includes the same 23 base pairs after the J segment that follow the mouse $J_K4$ segment. The purpose of these nucleotides is to provide a splice donor signal to ensure that the intron between the $V_L$ region and the downstream $C_L$ region (FIG. 5) is correctly spliced out. The correct orientation and sequence of the complete variable region ($V_L$) segment in pVk was then verified by sequencing again. All manipulations were done by standard methods (Sambrook J. et al.: *Molecular Cloning, A Laboratory Manual*, 2$^{nd}$ ed, Cold Spring Harbor Laboratory Press, N.Y. [1989]). Thus, the complete chimeric BR55-2 light chain gene consists of 1926 bp between an XbaI and a BamHI site (FIG. 5). It contains a variable region exon (including leader and J segments), followed by a short intron and then a constant region exon. The particular kappa constant region used is of the Inv3 allotype (Hieter P. A. et al.: *Cell* 22:, 197–207 [1985]), which occurs in 80% of the Caucasian population and 70% of the Black population (Sell S.: *Immunology, Immunopathology and Immunity*, 3$^{rd}$ ed. Harper & Row, Hagerstown, pp. 28 [1980]). The DNA following the termination codon of the $C_L$ segment contains a presumptive poly A signal (Boshart M. et al.: *Cell* 41, 521–520 [1985]) to allow termination of the mRNA transcript.

Chimeric BR55-2 Heavy Chain. The actual expressed heavy chain gene consists of two adjacent pans: a human genomic gamma 1 (or gamma 3) constant region built into the vector pVg1$^c$ (or pVg3$^c$), and the murine heavy chain variable region ($V_H$), constructed by PCR in the same manner as described above and cloned into the XbaI site of pVg1$^c$ (or pVg3$^c$) (FIGS. 6 and 7). The PCR generated segment (FIG. 9) encodes the $V_H$ domain, including the J segment and a typical immunoglobulin leader (signal) peptide, which is cleaved off as the heavy chain is secreted. In addition, the segment includes the same 19 base pairs after the J segment that follow the mouse $J_H3$ segment. The purpose of these nucleotides is to provide a splice donor signal to ensure that the intron between the $V_H$ and the downstream $C_H1$ is correctly spliced out. The orientation and sequence of the complete segment was verified after cloning into the XbaI site of the $pVg1^c$ (or $pVg3^c$).

Thus, the complete chimeric BR55-2 heavy chain gene contains a variable region exon (including leader and J segments), followed by a short intron and then the constant region (FIGS. 6 and 7). The gamma 1 constant region was obtained as a human genomic clone and therefore itself consists of 4 exons—$C_H1$, H (hinge), $C_H2$ and $C_H3$—separated by 3 introns. The gamma 3 constant region is similar to the gamma 1 constant region except that an extended H (hinge) is composed of four exons separated by three introns. The particular gamma 1 constant region used has the Gm(1,17) allotypic markers (Ellison J. W. et al.: *Nucleic Acids Research* 10, 4071–4079 [1979]), which occur in 60% of the Caucasian population and 100% of the Black population (Sell S.: *Immunology, Immunopathology and Immunity*, $3^{rd}$ ed. Harper & Row, Hagerstown, pp. 28 [1980]). The DNA following the termination codon of the $C_H3$ segment contains a presumptive poly A signal (Ellison J. W. et al.: *Nucleic Acids Research* 10, 4071–4079 [1979]) to allow termination of the mRNA transcript.

3. Transfected Cell Line

Host Cell System

The host cell line was Sp2/0-Ag14 (ATCC CRL 1581), which was developed by M. Shulman, C. D. Wilde and G. Kohler in 1978 (Shulman M. et al.: *Nature* 276, 269–270 [1978]). They isolated it as a re-clone of Sp/2/HL-Ag, which was derived from Sp2/HLGK, a hybrid between a BALB/c spleen cell with antisheep red blood cell activity and the mouse myeloma line P3x63Ag8. Sp2/0-Ag14 does not survive in HAT medium and has the important characteristic that it does not synthesize or secrete any immunoglobulin chains. For this reason, the cell line is commonly used as a fusion partner in generating hybridomas. It is equally suitable as a host cell line for producing a chimeric antibody, because only the transfected immunoglobulin genes will be expressed.

A vial of Sp2/0-Ag14 cells obtained from the American Type Culture Collection was thawed and then passaged several times to produce enough cells to perform DNA transfections. The cells were grown and the transfectants maintained in DMEM medium+10% fetal bovine serum (FBS).

Transfection of Cells. Transfection was by electroporation using a Gene Pulser apparatus (Bio-Rad) at 360 V and 25 µFD capacitance according to the manufacturer's instructions. Before transfection, the light chain- and heavy chain-containing plasmids were linearized using BamHI, extracted with phenol-chloroform, and ethanol-precipitated. All transfections were done using 20 µg plasmid DNA and about $10^7$ cells in PBS. The cells from each transfection were plated into one 96-well tissue culture plate. After 48 hours, selective medium was applied.

Cells were selected in DMEM+10% FBS+HT media supplement (Sigma)+1 µg/ml mycophenolic acid. After the wells had become confluent with surviving colonies of cells, medium from each well was assayed for the presence and quantity of secreted antibodies by ELISA. A high-yielding clone from each transfection was grown up to produce antibody for purification.

4. Purification of Chimeric BR55-2 Antibodies.

IgG1 chimeric antibody

BR55-2 IgG1 chimeric antibody was purified from serum-free conditioned media plus 0.5% FBS using Protein A Sepharose chromatography. 4 liter of culture medium was concentrated 16-fold using a Pellicon system equipped with a 10,000 MW CO cellulose membrane. The pH of the concentrate was adjusted to 8.5 using 1M Tris and the slight precipitate that formed was removed by centrifugation. The concentrate was then loaded, at a flow rate of 2 ml/min, onto a 1,6×12 cm Protein A Sepharose column (Pharmacia) which was pre-equilibrated with 0.15M NaCl, 50 mM Tris, pH 8.5 until the absorbance at 280 nm returned to baseline, and the bound IgG1 was eluted with 0.15M NaCl, 0.1M acetic acid. The fractions were collected into one-tenth volume of sodium bicarbonate, to neutralize the pH, and the pooled fractions were dialized against PBS and filter sterilized. Protein concentration was estimated by taking OD at 280 nm (1 mg/ml=1,35 OD). Antibodies were more than 95% pure based on SDS-PAGE analysis and size-exclusion HPLC (see FIG. 42).

IgG3 Chimeric Antibody

BR55-2 IgG3 chimeric antibody was purified from serum-free conditioned media using Protein G agarose chromatography. 4 liter of culture medium were concentrated 16 fold using a Pellicon system equipped with a 10,000MW CO cellulose membrane. The pH of the concentrate was adjusted to 5.0 using 1M acetic acid and the slight precipitate that formed was removed by centrifugation. The concentrate was then loaded, at a flow rate of 1 ml/min, onto a 1×6.5 cm Protein G agarose column (Pierce) which was pre-equilibrated with 0.15M NaCl, 20 mM sodium acetate, pH 5.0. The column was washed with 0.15M NaCl, 20 mM sodium acetate, pH 5.0 until the absorbance at 280 nm returned to baseline and the bound IgG3 was eluted with 0.1M glycine/HCl, pH 2.8. The fractions were collected into one-tenth volume of sodium bicarbonate, to neutralize the pH, and the pooled fractions were dialyzed against PBS and filter sterilized. Protein concentration was estimated by taking OD at 280 nm (1 mg/ml=1.35 OD). Antibodies were more than 95% pure based on SDS-PAGE analysis, and size-exclusion HPLC (see FIG. 42).

The "fully humanized" Mabs can be generated in the following manner:

1. Construction of Expression Vectors

Separate expression vectors were used to express the humanized BR55-2 IgG1 antibody light and heavy chains: pVk for the light chain, $pVg1^R$ for the gamma 1 heavy chain. Diagrams of these vectors, with relevant restriction sites indicated, are presented in FIGS. 5 and 10. pVk is as described above, $pVg1^R$ is described in detail below; nucleotide position numbers start with 1 at the EcoRI site and refer to the complete plasmids.

Plasmid $pVg1^R$. This plasmid is similar to pVk but contains a heavy chain instead of light chain constant region and a different selectable marker. Specifically, proceeding clockwise (FIG. 10), pVg1 contains the same CMV enhancer and promoter for strong transcription initiation as pVk, inserted with the same EcoRI and XbaI linkers. The variable region of an antibody heavy chain such as humanized BR55-2 can be inserted at the XbaI site. That site is followed by part of a genomic clone (Ellison J. W. et al., *Nucleic Acids Research* 10, 4071–4079 [1982]) containing the human gamma 1 heavy chain constant region ($C_H$) including the $C_H1$, hinge (H), $C_H2$ and $C_H3$ exons with the intervening introns, part of the intron preceding $C_H1$, and a poly A site following $C_H3$.

The $C_H$ region is followed by a gene encoding a mutant gene for dihydrofolate reductase (dhfr), together with regulatory elements (enhancer, promoter, splice signals, poly A signal) from SV40 needed for transcription. This unit is identical to the gpt unit in pVk, except that dhfr replaces gpt. The mutant dhfr gene (Simonsen C. C. et al., *Proc. Natl. Acad. Sci. USA* 80, 2495–2499 [1983]) confers resistance to methotrexate, so it can be used as a selectable marker after transfection into mammalian cells. The mutant dhfr was cloned from a wide-type gene with a single amino acid substitution at position 22 (Leu to Arg) and can be employed as a dominant selectable marker in cultured cells expressing normal levels of wide-type dihydrofolate reductase. This marker also allows to select higher antibody producers by subjecting cells to increased level of methotrexate. Finally, pVg1$^R$ contains the same part of the plasmid pBR322 as pVk, containing the origin or replication and amp gene for use in *E. coli*.

Plasmids pVg2, pVg3$^R$ and pVg4

These plasmids were constructed to express the human γ2, γ3 and γ4 heavy chains, respectively. The plasmids are identical to pVg1$^R$ except that the XbaI-BamHI fragment containing the human γ1 heavy chain constant region is replaced by XbaI-BamHI fragments containing the γ2, γ3 and γ4 heavy chain constant regions, respectively (Takahashi N., et al., *Cell* 29, 671–679 [1982] and Ellison, J. et al., *Proc. Natl. Acad. Sci. USA* 79, 1984–1988 [1982]). All the plasmids were constructed from their component parts in a number of steps by standard methods (Sambrook J. et al.: *Molecular Cloning, A Laboratory Manual*, 2$^{nd}$ ed., Cold Spring Harbor Laboratory Press, N.Y. [1989]), including synthesis of oligonucleotide linkers. Their structure was carefully verified during and after construction by restriction mapping and sequencing.

2. Computer Modeling of Humanized Variable Region Domain

In order to retain high binding affinity in the humanized antibody, the general procedures of Queen et al. (Queen, C. et al., *Proc. Natl. Acad. Sci. USA*, 86: 10029–10033 (1989)) were followed. The more homologous a human antibody is to the original murine antibody, the less likely will combining the murine CDRs with the human framework be to introduce distortions into the CDRs that could reduce affinity. The first step in the designing of humanized antibody is to perform a sequence homology search to select the best framework. Comparison of variable regions of BR55-2, murine IgG3, with a few selected human antibodies is shown below (E. A. Kabat et al., *Sequences of Proteins of Immunological Interest*, 4th Edition [1987], U.S. Dept. of Health and Human Services) (sequence homology including CDRs given in percentage):

| Ab | VL | VH |
|---|---|---|
| Eu | 54% | 43% |
| Sie | 57% | 41% |
| Ou | 48% | 41% |
| Lay | 56% | 64% |
| Pom | 56% | 64% |
| Tew | 77% | — |

Pom was selected to provide the framework for the humanized heavy chain and Tew for the humanized light chain variable region. Normally the heavy chain and light chain from the same human antibody are chosen to provide the framework sequences, so as to reduce the possibility of incompatibility in the assembling of the two chains. The BR55-2, murine IgG3, light chain variable region, however, shows a significantly higher homology to the Tew framework compared to any others.

Therefore, Tew was chosen to provide the framework for the humanized light chain variable region, despite the absence of available sequence for the heavy chain. Pom was chosen to provide the framework for the heavy chain because of its high homology to the BR55-2, murine IgG3, heavy chain sequence.

Next, the computer programs ABMOD and ENCAD (Zilber, B. T. et al., *Biochemistry* 29: 10032–10041) were used to construct a molecular model of the BR55-2, murine IgG3, variable domain. Inspection of the refined model of murine BR55-2 revealed several amino acid residues in the framework that have significant contacts with the CDR residues (category 4 below). To design the humanized light and heavy chain BR55-2 variable regions, at each position the amino acid was chosen to be the same as in the Tew or Pom sequence, respectively, unless that position fell in one or more of the four categories:

(1) The position fell within a CDR, (2) The Pom or Tew amino acid was unusual for human antibodies at that position, whereas the BR55-2. murine IgG3, amino acid was typical for human antibodies at that position.

(3) The position was immediately adjacent to a CDR.

(4) The model described above suggested that the amino acid may be physically close to the antigen binding region (CDRs).

| Category | Light Chain | Heavy Chain |
|---|---|---|
| 1 | 24–39, 55–61, 94–102 | 31–35, 50–66, 99–108 |
| 2 | 108 | 82, 87 |
| 3 | | 109 |
| 4 | 54 | 73, 74, 109 |

The humanized light chain and heavy chain sequences are labeled L-hu-BR55-2 and H-hu-BR 55-2/1, respectively. Binding affinity measurements showed that the binding affinity of the humanized antibody is roughly four fold lower than that of the BR55-2 mouse/human chimeric IgG1 antibody.

Since the overall electrostatics of a protein can affect the binding of a substrate, this effect was investigated in an effort to increase the binding affinity of the humanized antibody. The amino acid sequences of the humanized heavy chain and the murine heavy chain were compared to identify framework residue differences that result in a charge change. Several humanized heavy chain variants with single or double amino acid substitutions from the murine sequence were constructed. One variant with substitutions at position 42 (Gly to Glu) and position 44 (Gly to Arg) increases the binding affinity by two fold. One variant with a substitution at position 95 (Tyr to His), which is involved in the interfacing with the light chain, also increases binding affinity by two fold. A variant chain, incorporating these three substitutions, the sequence of which is labeled H-hu-BR55-2/2, was constructed and shown to bind to the antigen with affinity within two fold of the BR55-2 mouse/human chimeric IgG1 antibody.

It was also found that substituting residue: 75 in the heavy chain with the murine residue enhances antibody secretion. The humanized heavy chain sequence, which incorporates this additional change, is labeled H-hu-BR55-2/3. The heavy chains described above were then cotransfected each with the L-hu-BR55-2 light chain to produce the respective humanized antibodies.

The variants with the heavy chain sequence H-hu-BR55-2/2 and H-hu-BR55-2/3 were named BR55-2 humanized IgG1/2 and BR55-2 humanized IgG1/3 respectively. An alignment and comparison of the three humanized heavy chain variants is shown in FIG. 11. A comparison of the humanized light chain, L-hu-BR55-2, and the humanized heavy chain, H-hu-BR55-2/3, with the respective Tew and Pom sequences are shown in FIGS. 12 and 13.

3. Construction of Variable Domain Segments

Humanized BR55-2 Light Chains. The actual expressed humanized BR55-2 light chain gene consists of two adjacent parts: a human genomic kappa constant region built into the vector pVk (see above), and the humanized light chain variable region ($V_L$) constructed by total gene synthesis from oligonucleotides.

For the construction of light chain variable region gene, nucleotide sequences were selected that encode the protein sequences of the humanized light chain, including the signal peptide, generally utilizing codons found in the mouse sequence. Several degenerate codons were changed to create restriction sites or to remove undesirable ones. The nucleotide sequences also included a splice donor signal from the $J_K4$ in the mouse genomic sequence and an XbaI site at each end. The gene was constructed from four overlapping synthetic oligonucleotides (FIG. 14). For the variable domain gene, two pairs of overlapping synthetic oligonucleotides on alternating strands were synthesized that encompassed the entire coding sequences as well as the signal peptide and the splice donor signal. The oligonucleotides were synthesized on an Applied Biosystems 380B DNA synthesizer. Each oligo was about 110–140 base long with a 15 base overlap. Double stranded DNA fragments were synthesized with Klenow polymerase, digested with restriction enzymes, ligated to pUC18 vector and sequenced. The two fragments with the correct sequences were then ligated into the XbaI sites of pVk expression vector.

Thus, the cloned segment encodes the humanized $V_L$ domain, including the J segment and a typical immunoglobulin leader (signal) peptide, which is cleaved off as the light chain is secreted. In addition, the segment includes the same 23 base pairs after the J segment that follow the mouse $J_K4$ segment. The purpose of these nucleotides is to provide a splice donor signal to ensure that the intron between the $V_L$ region and the downstream $C_L$ region (FIG. 5) is correctly spliced out. The correct orientation and sequence of the complete variable region ($V_L$) segment in pVk was then verified by sequencing again. All manipulations were done by standard methods (Sambrook, J. et al., *Molecular Cloning: A Laboratory Manual*, $2^{nd}$ ed., 1989).

Thus, the complete humanized BR55-2 light chain gene consists of the segment between a XbaI and a BamHI site (FIG. 5). It contains a variable region exon (including leader and J segments), followed by a short intron and then a constant region exon. The particular kappa constant region used is of the Inv3 alloype (Hieter, P. A. et al., *Cell* 22: 197–207 (1980)), which occurs in 80% of the Caucasian population and 70% of the Black population (Sell, S., *Immunology, Immunopathology and Immunity*, $3^{rd}$ ed. (Harper and Row: Hagerstown, Md.) pp. 28 (1980)). The DNA following the termination codon of the $C_L$ segment contains a presumptive poly A signal (Boshart, M. et al., *Cell* 41: 521–530 (1985)) to allow termination of the mRNA transcript.

Humanized BR55-2 Heavy Chains

The actual expressed heavy chain gene consists of two adjacent parts: a human genomic gamma 1 constant region built into the vector pVg1, and the humanized heavy chain variable region ($V_H$), constructed by total gene synthesis in the same manner as described above and cloned into the XbaI site of pVg1 (FIG. 10). The XbaI fragment, which can be synthesized from four oligonucleotides (FIG. 15), encodes the humanized $V_H$ domain, including the J segment and a typical immunoglobulin leader (signal) peptide, which is cleaved off as the heavy chain is secreted. In addition, the segment includes the same 19 base pairs after the J segment that follows the mouse $J_H3$ segment. The purpose of these nucleotides is to provide a splice donor signal to ensure that the intron between the $C_H$ and the downstream $C_H1$ is correctly spliced out. The orientation and sequence of the complete segment was verified after cloning into the XbaI site of the pVg1.

Thus, the complete humanized BR55-2 γ1 heavy chain gene contains a variable region exon (including leader and J segments), followed by a short intron and then the constant region (FIG. 6). The gamma 1 constant region was obtained as a human genomic clone and therefore itself consists of 4 exons—$C_H1$, H (hinge), $C_H2$ and $C_H3$—separated by 3 introns. The particular gamma 1 constant region used has the Gm (Chiang, Y. L., Sheng-Dong, R., Brow, A. and Larrick, J. W., *BioTechniques* 7, 360–366 (1989)) allotypic markers (Ellison, J. W. et al., *Nucleic Acids Research* 10: 4071–4079 (1982)), which occur in 60% of the Caucasian population and 100% of the Black population (Sambrook, J. et al., *Molecular Cloning: A Laboratory Manual*, $2^{nd}$ ed. (Cold Spring Harbor Laboratory Press, N.Y.) (1989)). The DNA following the termination codon of the $C_H3$ segment contains a presumptive poly A signal to allow termination of the mRNA transcript.

For expression of humanized BR55-2 IgG1, IgG2, IgG3 and IgG4, the XbaI fragment coding the humanized BR55-2 heavy chain variable region, including the signal sequence and the 3' splicing signal, was inserted into the XbaI site of the respective vectors. Orientation and sequence of the variable region gene was confirmed by restriction digestion and sequencing. Each of the heavy chain expressing plasmids was cotransfected with the humanized BR55-2 light chain expressing plasmid into SP2/0 cells.

4. Transfected Cell Lines

This step of the process is similar to the procedure described for the mouse/human chimeric Mabs. However, based on the methotrexate resistance introduced in the respective pVg1$^R$, pVg2, pVg3$^R$ and pVg4 it is possible to obtain a high yielding cell line by selection of antibody-producing cells from the transfection in 50 nM methotrexate. This can be done in the following manner.

Surviving cells were subjected to increasing concentrations of methotrexate (two fold stepwise) until the level of antibody production reaches the maximum. The best producing cells were then subcloned twice by limited dilution and the highest-yielding clone was selected for production of the respective antibody.

5. Purification of Humanized Mabs

This step of the process can be carried out similarly to the procedure described for the mouse/human chimeric Mabs. The IgG1, IgG2 and IgG4 Mabs were purified using Protein A Sepharose columns, the IgG3 was purified using a Protein G Agarose column. Isotypes of the purified Mabs were confirmed by a human IgG subclass EIA kit (Isotypes, Inc. Newark, Del.) (see also FIG. 42).

The potential of an unconjugated antitumor Mab for tumor cell destruction is determined by its binding properties to the tumor associated antigen as well as by the constant domains responsible for activation of effector functions.

In general, the binding properties of a mouse/human chimeric Mab are similar compared to the binding properties of the parent murine Mab. However, fully humanized Mabs obtained by grafting of the CDR into human framework and reshaping by molecular modelling may exhibit lower binding affinity than the parent murine Mab and the mouse/human chimeric Mabs. Remarkably, the binding properties of the fully humanized Mabs described in this invention are still comparable to the binding properties of the mouse/human chimeric Mabs and the parent murine Mabs.

Murine Mabs BR55-2, depending on their subclass, activate both human complement and human effector cells for tumor cell destruction, the murine IgG3 subclass being most effective in this respect. In case of the mouse/human chimeric Mabs and the fully humanized Mabs with binding specificity of BR55-2 described in this invention the most active subclass for activation of human effector functions is human IgG1. However, the pattern of activation of human effector functions is different. While the complement activation ability is somewhat diminished in comparison to murine IgG3, the ability for activation of human effector cells for tumor cell destruction is superior.

The Lewis Y antigen is also selectively expressed on HIV-infected cells. Based on this observation Mabs with specificity of BR55-2 are also useful for immunotherapy of HIV-infection. BR55-2 humanized IgG1/3 displays significant antiviral properties by reducing by more than 90% the infectivity of HIV-infected cultures of human PBMCs. Therefore BR55-2 mouse/human chimeric Mabs and BR55-2 humanized Mabs are promising for immunotherapy of HIV. Since the Lewis Y carbohydrate antigen is specified by the infected cell and not by the viral genom, HIV escape mutants (which are a major problem in therapy of AIDS) are highly unlikely to occur during immunotherapy with Mabs with specificity of BR55-22, leading to at unique advantage of such a therapy over existing treatment modalities.

The above mentioned properties and activities can be shown in the following tests and studies:

1. Binding of Mouse/Human Chimeric and Humanized Variants of BR55-2 to SKBR5 Breast Cancer Cell Line The Lewis Y carbohydrate antigen is strongly expressed on the surface of the human breast cancer cell line SKBR5. Both the BR55-2/mouse/human chimeric Mabs and the BR55-2 humanized Mabs efficiently bind to this cell line in a cell-ELISA (see example 1 for experimental details and FIGS. 16 to 18 for results). The binding of BR55-2 mouse/human chimeric IgG1 (bearing the same variable region as the parent murine IgG3Mab) to this cell line was also compared with the binding of BR55-2 humanized IgG1/3 (bearing only the CDRs of the parent murine IgG3Mab inserted in human framework) using fluorescence activated flow cytometry (see example 2 for experimental details). As shown in FIGS. 19 and 20, the binding properties of both variants are comparable, the affinity is almost fully retained after the humanization procedure.

2. Complement Dependent Cytotoxicity Mediated by Mouse/Human Chimeric and Humanized Variants of BR55-2

The destruction of several Lewis Y antigen positive human tumor cell lines by BR55-2 mouse/ human chimeric IgG1 and -IgG3 as well as by BR55-2 humanized IgG1/2 and -IgG1/3 via activation of human complement was tested in comparison to the parent murine IgG3Mab. The cell lines used were: SKBR5: breast cancer; CATO: gastric cancer; MCF7: breast cancer; SW 948: colon cancer; SW2: small cell lung cancer. The results are shown in FIGS. 21 to 30. They indicate that the human IgG3 subclass is significantly less active in complement mediated destruction than the human IgG1 subclass. The BR55-2 humanized IgG1 variants mediate tumor cell lysis comparable to the BR55-2 mouse/human chimeric IgG1. However, the parent mouse IgG3Mab is more potent in complement dependent lysis (see example 3 for experimental details).

3. Antibody Dependent Cellular Cytotoxicity Mediated by Mouse/Human Chimeric and Humanized Variants of BR55-2

The destruction of several Lewis Y antigen positive human tumor cell lines by BR55-2 mouse/human chimeric IgG1 and -IgG3 as well as by BR55-2 humanized IgG1/2 and -IgG1/3 via activation of human peripheral mononuclear cells as well as human monocytes and human granulocytes was tested in comparison to the parent murine IgG3Mab. The cell lines used were: CATO: gastric cancer; SKBR5: breast cancer; MCF7: breast cancer; SW948: colon cancer; SW2: small cell lung cancer. The human IgG3 subclass is less active in tumor cell destruction via activation of human effector cells than the human IgG1 subclass. However, the ADCC activity of BR55-2 mouse/human chimeric IgG1 as well as of the BR55-2 humanized IgG1 variants tested is significantly superior to the activity of the parent murine IgG3Mab. This activity pattern is similar for human PBMCs, human monocytes and human granulocytes as effector cells. Interestingly, for BR55-2 humanized IgG1/2 in all experiments a higher efficacy was found than for BR55-2 humanized IgG1/3 which by itself is comparable to BR55-2 mouse/human chimeric IgG1 (see example 4 for experimental details). The results are shown in FIGS. 31 to 41.

4. Mixed Cell HIV-infectivity Assay

Human PBMCs were infected with HIV and feeded after one week with fresh autologous serum and lymphocytes to provide complement and effector cells, respectively. After one week incubation with BR55-2 humanized IgG1/3 infectivity of the cell culture supernatant was titrated in MT-4 cells (see example 5 for experimental details). BR55-2 humanized IgG1/3 significantly inhibits the infectivity, especially in the presence of fresh serum. The results are shown in Table 1.

TABLE 1

Infectivity of supernatants of HIV-infected human PBMC cultures treated with BR55-2 humanized IgG1/3

|  | Titer* (heat inactivated serum) | Titer* (fresh serum) |
|---|---|---|
| BR55-2 humanized IgG1/3 (80 μg/ml) | 1:316 | 1:100 |
| PBS (control) | 1:1000 | 1:3160 |

*end-point titers from titration of the PBMC supernatants in MT-4 cells.

The following examples illustrate the invention but are not limitative. All temperatures are given in degrees centigrade. The abbreviations have the following meanings:

ADCC: antibody dependent cellular cytotoxicity amp: ampicillin

BSA: bovine serum albumin

CDC: complement dependent cytotoxicity

CDR: complementarity determining regions

CMV: cytomegalovirus dhfr: dihydrofolate reductase

DNA: desoxyribonucleic acid dGTP: desoxyguanosine-5'-triphosphate dNTP: desoxynucleotide-5'-triphosphate DTT: dithiothreitol EDTA: ethylene diamine tetraacetic acid
ELISA: enzyme-linked immunosorbent assay
FBS: fetal bovine serum
Fc: fragment crystallizable
FCS: fetal calf serum
gpt: guanine phosphoribosyl transferase
HAMA: human anti-mouse antibody
HBSS: Hank's buffered saline (Gibco)
HIV: human immunodeficiency virus
Ig: Immunoglobulin
Mab: monoclonal antibody
PAGE: polyacrylamide gel electrophoresis
PBMC: peripheral blood mononuclear cells
PBS def.: phosphate buffered saline
PBS def.2: PBS def.+0.1% EDTA+0.1% NaN$_3$+1% FCS (heat inactivated)
PCR: polymerase chain reaction
PHA: phytohemaglutinin
polyA: polyadenylation
RNA: ribonucleic acid
RPMI: Roswell Park Memorial Institute
SCLC: small cell lung cancer
SDS: sodium dodecyl sulfate
SV40: Simian Virus 40
TdT: terminal desoxynucleotidyl transferase
The materials referred to in the examples are as follows:
Cell Lines
SKBR5: human breast cancer cell line
MCF7: human breast cancer cell line
SW948: human colon cancer cell line
CATO: human gastric cancer cell line
SW2: human small cell lung cancer line
Medium A
RPMI 1640+2 g/l NaHCO$_3$
100 U/ml Penicillin G
100 μg/ml streptomycin sulfate
4 mM glutamine
10% FCS (heat-inactivated, γ-globulin-free)
Medium A2
Medium A without phenol red
HAT Medium
hypoxanthine-aminopterin-thymidine
DMEM Medium
Dulbecco's modified eagles medium
Lymphoprep
density 1.077±0.001 g/ml
PBS complete
138.0 mM NaCl
1.5 mM KOH
2.7 mM KCl
6.5 mM Na$_2$HPO$_4$
0.9 mM CaCl$_2$.2H$_2$O
0.5 mM MgCl$_2$.6H$_2$O
PBS Deficient
138.0 mM NaCl
1.5 mM KOH
2.7 mM KCl
6.5 mM Na$_2$HPO$_4$
pH 7.2
Coating Buffer
15 mM Na$_2$CO$_3$
35 mM NaHCO$_3$
3 mM NaN$_3$
pH 9.6
Staining Buffer
24.3 mM citric acid
51.4 mM Na$_2$HPO$_4$
pH 5.0
Washing Buffer
0.2% Triton X-100
2% NaCl
in PBS deficient
Substrate Solution
40 mg o-phenylenediamine dihydrochloride
100 ml staining buffer
20 μl H$_2$O$_2$ (30%)
Na$_2$$^{51}$CrO$_4$
1 mCi/ml

EXAMPLE 1

Binding of BR55-2 Mouse/Human Chimeric IgG1
and BR55-2 Mouse/Human Chimeric IgG3 to
SKBR5 Cell Line (cell-ELISA)

Microtiter plates are pretreated with poly-L-lysine hydrobromide (20–30 kD; 20 μg/ml in PBS def.; 100 μl/well; 30 minutes, room temperature), washed twice with PBS def. (200 μl/well) and then incubated overnight at 4° with a suspension of SKBR5 cells to be tested at a concentration of 4×10$^6$ cells/ml (50 μl of cell suspension/well). After removal of the supernatant the cells are fixed with 50 μl glutardialdehyde (0.1% in physiological saline) per well for 5 minutes at room temperature, the supernatant is removed, 200 μl/well of PBS def./1% BSA/0.1% NaN$_3$ are added and left for 1 hour at room temperature. After removal of the supernatants and washing twice with 200 μl PBS/Tween 20 (0.05%) per well, the antibody dilutions (100 μg/ml down to 0.08 μg/ml in PBS def.) are incubated for 1 hour at 37°. Unbound antibody is washed out twice with 100 μl of ice-cold PBS/Tween 20 (0.05%) per well and peroxidase-conjugated antibody is added. The conjugate used is goat anti-human IgG-peroxidase (such as the reagents of Chemicon Co.) 1:1000 in PBS def./2% FCS. After incubation for 45 minutes at 37° the wells are washed thrice with the above PBS/Tween 20 solution and then 100 μl of substrate solution is added to each well. After 5 minutes colour development is stopped by addition of 50 μl of 4N H$_2$SO$_4$/well. Binding of the antibody to the cells is determined by measuring extinction at 492 nm (calibration is at 620 nm).

EXAMPLE 2

Binding of BR55-2 Mouse/Human Chimeric IgG1
and BR55-2 Humanized IgG1/3 to SKBR5 Cell
Line (Fluorescence-activated Flow Cytometry)

SKBR5 cells are cultivated in medium A2, spun down at 400 g, washed in PBS def. 2 and aliquoted into vials for fluorescence-activated flow cytometry (e.g. using FACScan; Becton Dickinson). To 10$^6$ cells in 500 μl medium A2 appropriate antibody dilutions are added in 250 μl PBS def. and incubated for 1 hour at 4°. After washing the cells with PBS def. 2 FITC labeled goat antihuman IgG is added (such as the reagents of Axell; 6 μg/vial in 100 μl PBS def.) and incubated overnight at 4°. The cells are washed as described above and resuspended in 300 μl PBS def. 2 (with 2% paraformaldehyde). After 2 hours incubation at 4° 150 μl PBS def. 2 are added and the cell suspensions are analyzed using the flow cytometer.

EXAMPLE 3

Complement Dependent Cytotoxicity (CDC) Using Human Serum

On the day preceding the assay the respective tumor target cells are transferred into fresh medium A and kept at 37°/5% $CO_2$ in a cell culture flask.

$^{51}$Cr labelling of the target cells:

The cells are collected from the culture flask and incubated at a concentration of 5×10$^6$ cells in 800 μl of medium A at 37°/5% $CO_2$ for 1 hour with 100 μCi $Na_2$ $^{51}CrO_4$. The cells are then washed with medium A to remove the excess $^{51}$Cr, resuspended in fresh medium A and their concentration is adjusted to 2.5×10$^5$ cells/ml.

CDC

100 μl aliquots of this suspension of target cells are pipetted into each well and 50 μl aliquots of the antibody solution, diluted to the desired concentrations in PBS def., are added. Then 100 μl aliquots of a human serum (final dilution 1:2.5) are added per well and the cells are incubated overnight at 37°/5% $CO_2$. The supernatants are harvested with a Skatron-Harvesting-Press and counted in a γ-counter. This yields the value for the experimental release. For determination of total $^{51}$Cr release the cells are treated as above but with the human serum replaced by a solution of 2% SDS, 50 mM $Na_2CO_3$ and 10 mM EDTA. The value for spontaneous $^{51}$Cr release is obtained by replacing the human serum with medium A and the antibody solution with 50 μl PBS def.

After counting the result is computed as follows:

$$\frac{\%}{\text{lysis}} = \frac{(\text{experimental release minus spontaneous release}) \times 100}{\text{total release minus spontaneous release}}$$

EXAMPLE 4

Antibody-dependent Cellular Cytotoxicity (ADCC)

On the day preceding the assay the respective tumor target cells are transferred into fresh medium A and kept at 37°/5% $CO_2$ in a cell culture flask.

$^{51}$Cr labelling of the target cells is effected as described in example 3.

Isolation of PBMC 50 ml of heparinized fresh human blood are diluted with 50 ml of PBS complete containing 0.1% glucose. 15 ml aliquots of this solution are layered on top of 15 ml of Lymphoprep solution and the tubes are centrifuged at 800 g for 30 minutes. The plasma supernatants are discarded, the PBMC layers are collected and diluted to 50 ml with PBS complete +0.1% glucose. After centrifugation (250 g, 10 minutes), resuspension of the pellet in 25 to 30 ml PBS complete+0.1% glucose, and recentrifugation (350 g, 10 minutes), the pellet is collected, suspended in medium A, the cells are counted and the suspension is diluted with medium A to about 2×10$^6$ to 9×10$^6$ cells/ml. 100 μl aliquots are pipetted into each well of a microtiter plate and the effector cells are incubated overnight at 37°/5% $CO_2$.

Isolation of Monocytes. Human monocytes are isolated via centrifugal elutriation as described (Thelen M. et al., *Blood* 75, 2223–2228 [1990]). The cells are resuspended in medium A and diluted to 10$^7$ cells/ml. 100 μl aliquots are pipetted into each well of a microtiterplate and incubated overnight at 37°/5% $CO_2$.

Isolation of Granulocytes. 50 ml of heparinized fresh human blood are diluted with 50 ml of PBS complete containing 0.1% glucose. 15 ml aliquots of this solution are layered on top of 15 ml of Lymphoprep solution and the tubes are centrifuged at 800 g for 30 minutes. The supernatants are discarded and the pellets are diluted in 30 ml HBSS. After gently rotating a further dilution is done to 1:5 with HBSS+6% Dextran. After 20 min (room temperature) erythrocytes are sedimented, the granulocytes in the supernatant are collected, spun down and washed twice with medium A. The cells are resuspended in medium A and diluted to 10$^7$ cells/mi. 100 μl aliquots are pipetted into each well of a microtiterplate and incubated overnight at 37°/5% $CO_2$.

ADCC

100 μl of $^{51}$Cr-labelled target cells are added to the preincubated effector cells in the desired ratio of effector cells to target cells. 50 μl of antibody solution diluted to the desired concentrations with PBS def. are added and the plate is incubated overnight (about 18 hours) at 37°/5% $CO_2$. The supernatants are then harvested with a Skatron-Harvesting Press and counted in a γ-counter. This yields the value for the experimental release.

Total $^{51}$Cr release is determined as above but replacing PBMC with 100 μl of 2% SDS, 50 mM $Na_2CO_3$ and 10 mM EDTA and replacing the antibody solution with 50 μl of PBS def. Spontaneous $^{51}$Cr release is obtained by replacing PBMC with 100 μl of medium A and the antibody solution with 50 μl of PBS def. The result is computed as described in example 3.

EXAMPLE 5

Mixed Cell HIV-infectivity Assay

PBMC from a healthy donor were separated from peripheral blood and stimulated with 5 μg/ml PHA for three days, inoculated with HIV$_{III}$B (M. Popovic et al., *Science* 224, 497 [1984]) overnight, washed and cultured in growth medium. One week after inoculation when infection was indicated by syncytium formation, fresh serum and PBMCs were obtained from the same donor, and some of the serum was heat inactivated (56° for 30 min). Uninfected PBMC. (0.6× 10$^6$) were mixed with 0.3×10$^6$ infected PBMC and 300 μl serum with or without heat inactivation. Appropriate concentration of BR55-2 humanized IgG1/3 or PBS was added to the mixture which was then cultured in a total volume of 1.5 ml growth medium per well of a 24-well cell culture plate. After one week a ten-fold dilution series of each supernatant was used for infection of MT-4 cells to get an approximate end point titer measured by production of HIV p24 antigen in culture supernatants of MT-4 cells as indicator for HIV-infections as described previously (J. Hansen et al., *J. Virol.* 65, 6461 [1991]).

On view of the above experimental results chimeric and humanized Mabs of BR55-2 and fragments thereof having the same specificity and variants thereof, are thus indicated for use in the diagnosis and treatment of cancer of epithelial origin, e.g. breast-, colorectal-, ovarian-, prostate-, pancreatic- or gastric cancer,; and of small cell lung cancer and for use in the tratment of HIV infections, especially of AIDS.

Since they show a restricted binding specificity associated with a lack of cross-reactivity to related antigens expressed on blood cells, e.g. erythrocytes, they are particularly suited for therapeutic use in humans.

For the above-mentioned use the dosage will, of course, vary depending upon e.g. the compound employed, the subject patient's age, the stage of disease, the mode of administration or the treatment desired, and can be determined by the specialist in each individual situation. It will also vary when the antibodies are used in combination with chemotherapeutic agents or immunostimulators. Administration is e.g. parenteral by injection or infusion. The dosage administered is e.g. of from about 10 mg to about 300 mg of chimeric or humanized Mab as defined above, given in intervals of 3 to 7 days, preferably by slow intravenous infusion.

The invention therefore also concerns a method of treatment of cancer of epithelial origin, e.g. breast-, colorectal-, ovarian-, prostate-, pancreatic- or gastric cancer, of small cell lung cancer and of HIV infections, especially of AIDS, which comprises administering to a subject in need of such treatment an effective amount of the antibody.

BRIEF DESCRIPTION OF THE FIGURES

FIG. 2: Primers: primers used in the anchored polymerase chain reactions.

a) mc45 anneals to the G-tail (SEQ ID NO:1);

b) mc46 anneals to the constant region of kappa chain (SEQ ID NO:2);

c) mc47 anneals to the constant region of gamma chains (SEQ ID NO:3). The sequence in parenthesis indicates a base degeneracy at the position. The degeneracy was introduced so that the primer would be able to recognize all classes of gamma chains.

FIG. 3: BR55-2 murine IgG3 light chain variable domain sequence (SEQ ID NOS:4 and 5): the initiation codon is underlined. The first amino acid of the mature protein is marked 1. CDR's are underlined. 5' untranslated sequence is also given.

FIG. 4: BR55-2 murine IgG3 heavy chain variable sequence (SEQ ID NOS:6 and 7): the initiation codon is underlined. The first amino acid of the mature protein is marked 1. CDR's are underlined. 5' untranslated sequence is also given.

Figure 1:
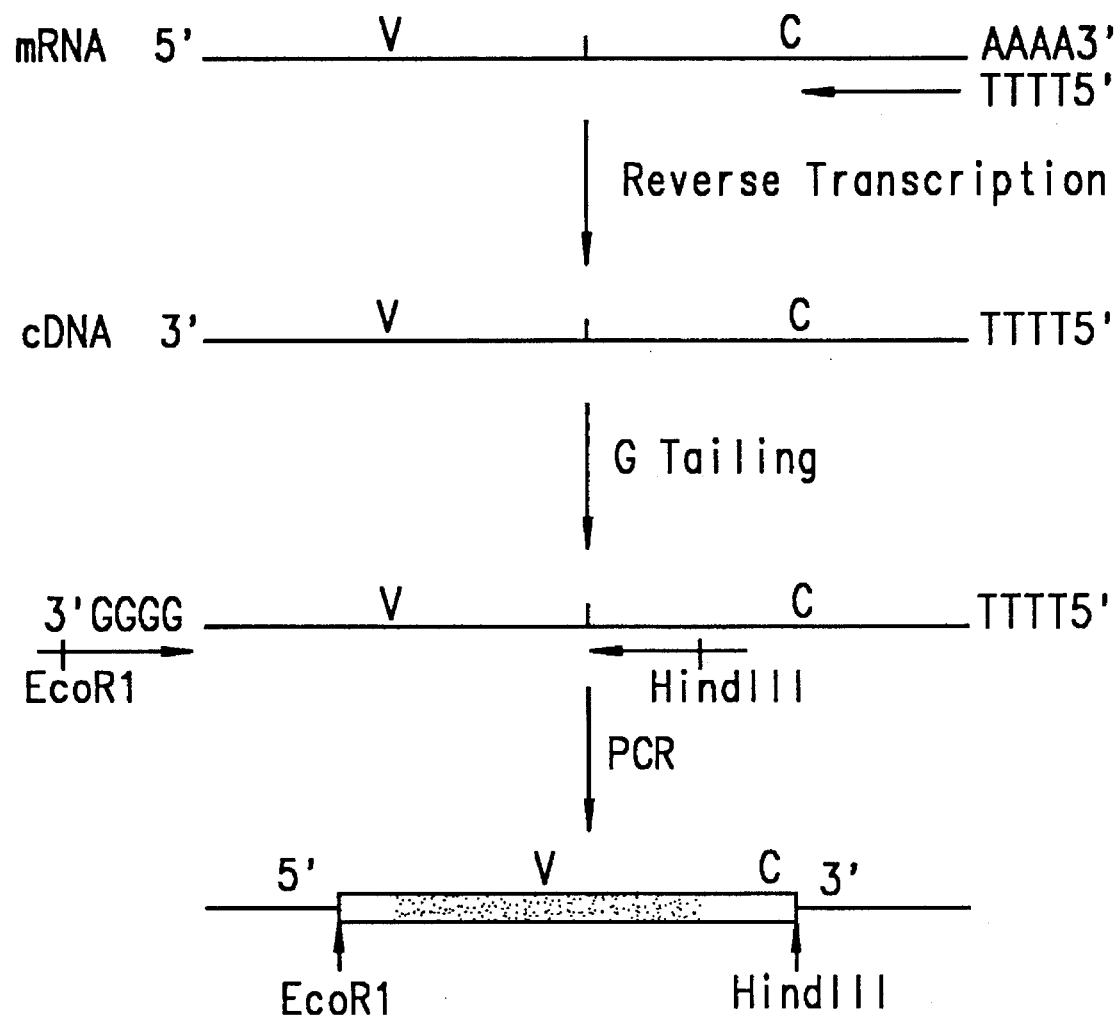
FIG. 1: Immunoglobulin Cloning Strategy: $V_H$ and $V_L$ genes were cloned using the anchored polymerase chain reaction (PCR). cDNA was synthesized from 5 μg of total RNA using reverse transcriptase and oligo dT as primers. A G-tail was attached to the 3'end of the cDNA using terminal deoxynucleotidyl transferase (TdT). The G-tail cDNA was then amplified using a pair of primers, one annealed to the constant region of light chain or heavy chain, the other annealed to the G-tail. Restriction sites are incorporated into the upstream and downstream primers for convenient cloning into pUC18 vector for sequence determination.
Figure 5:
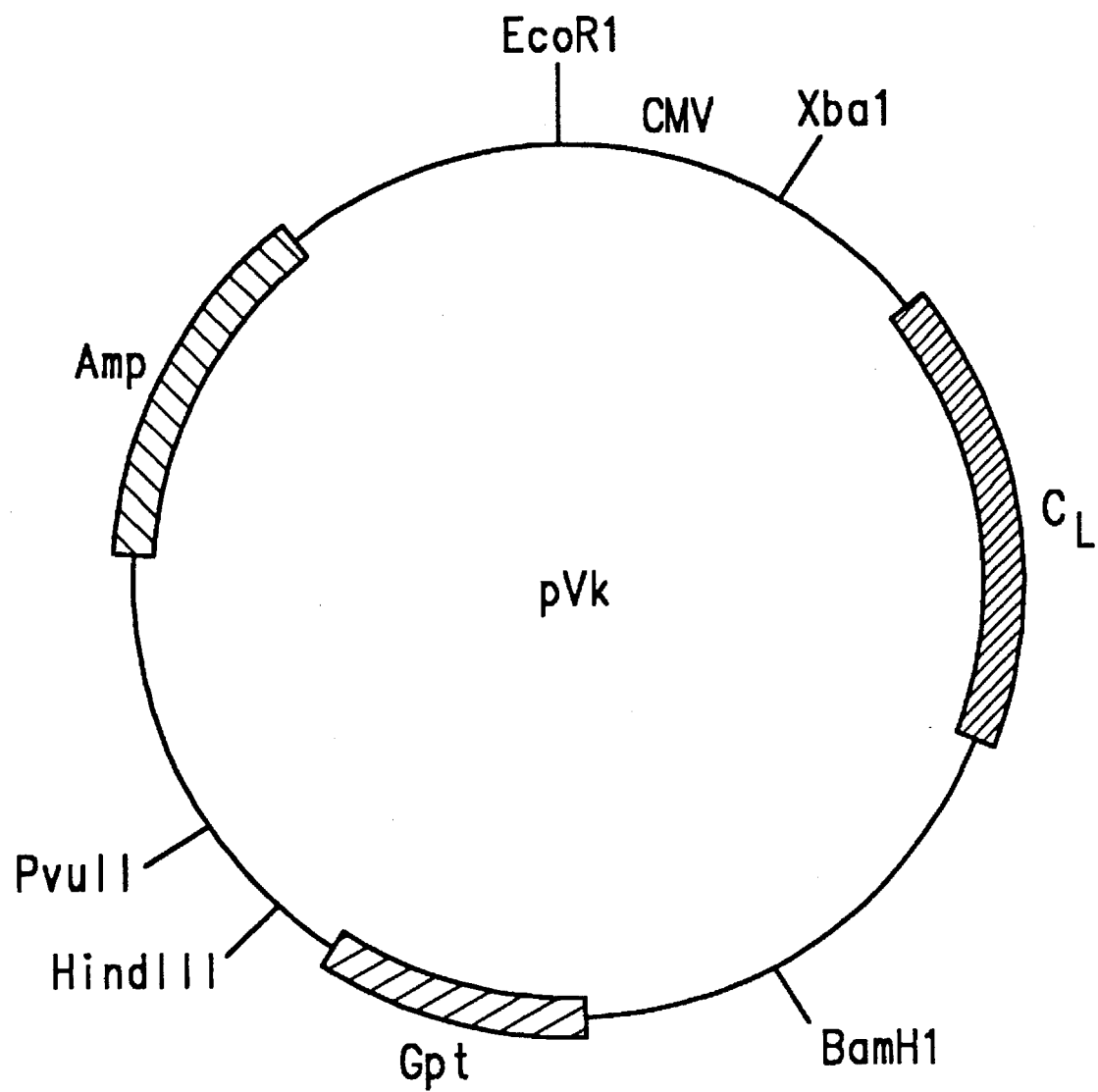

FIG. 5: Diagram of plasmid pVk: component parts are labeled, coding regions are shown as boxes, and restriction sites used in the construction are labeled.

Figure 6:
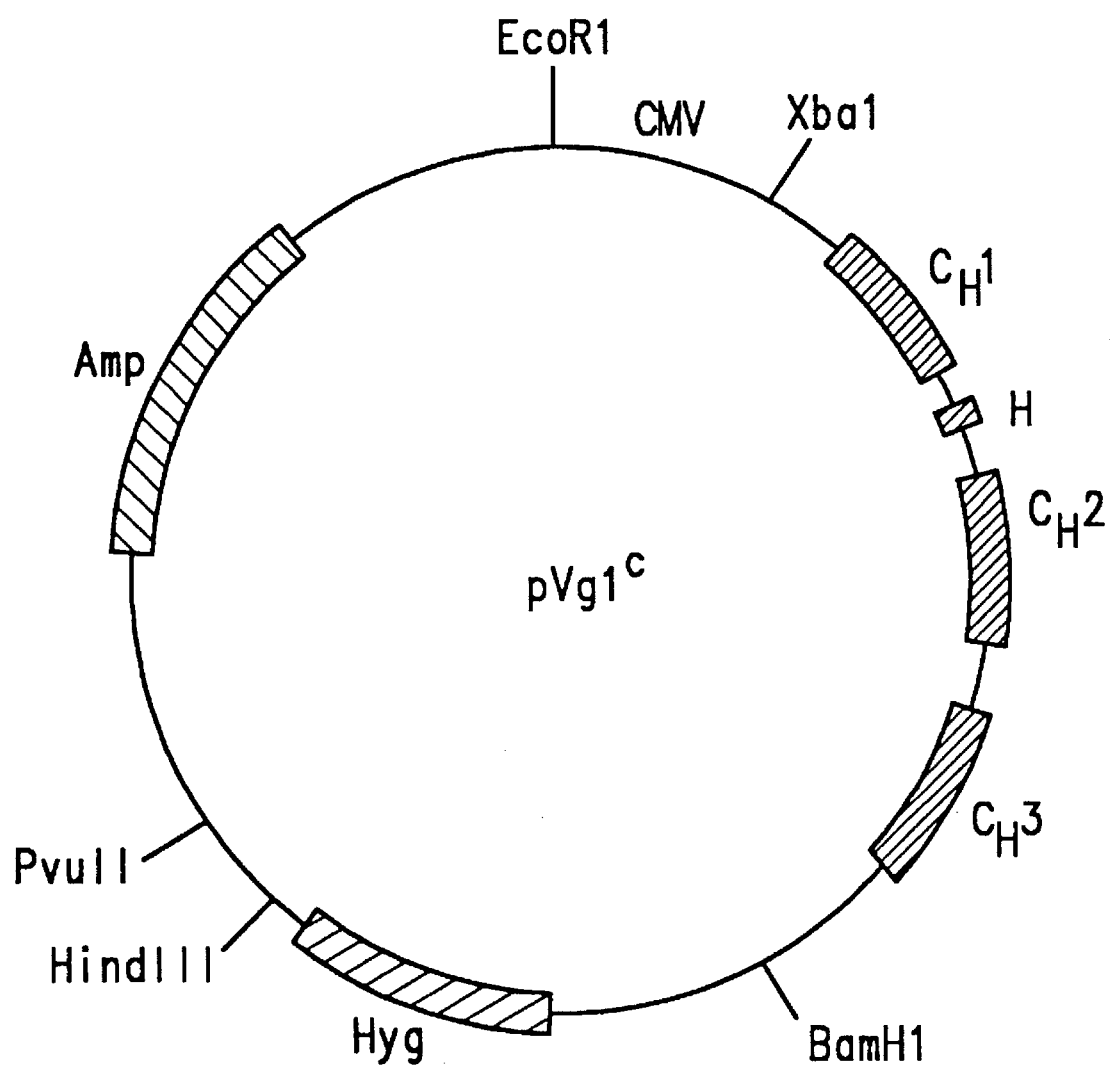

FIG. 6: Diagram of plasmid $pVg1^c$: component parts are labeled, coding regions are shown as boxes, and restriction sites used in the construction are labeled.

Figure 7:
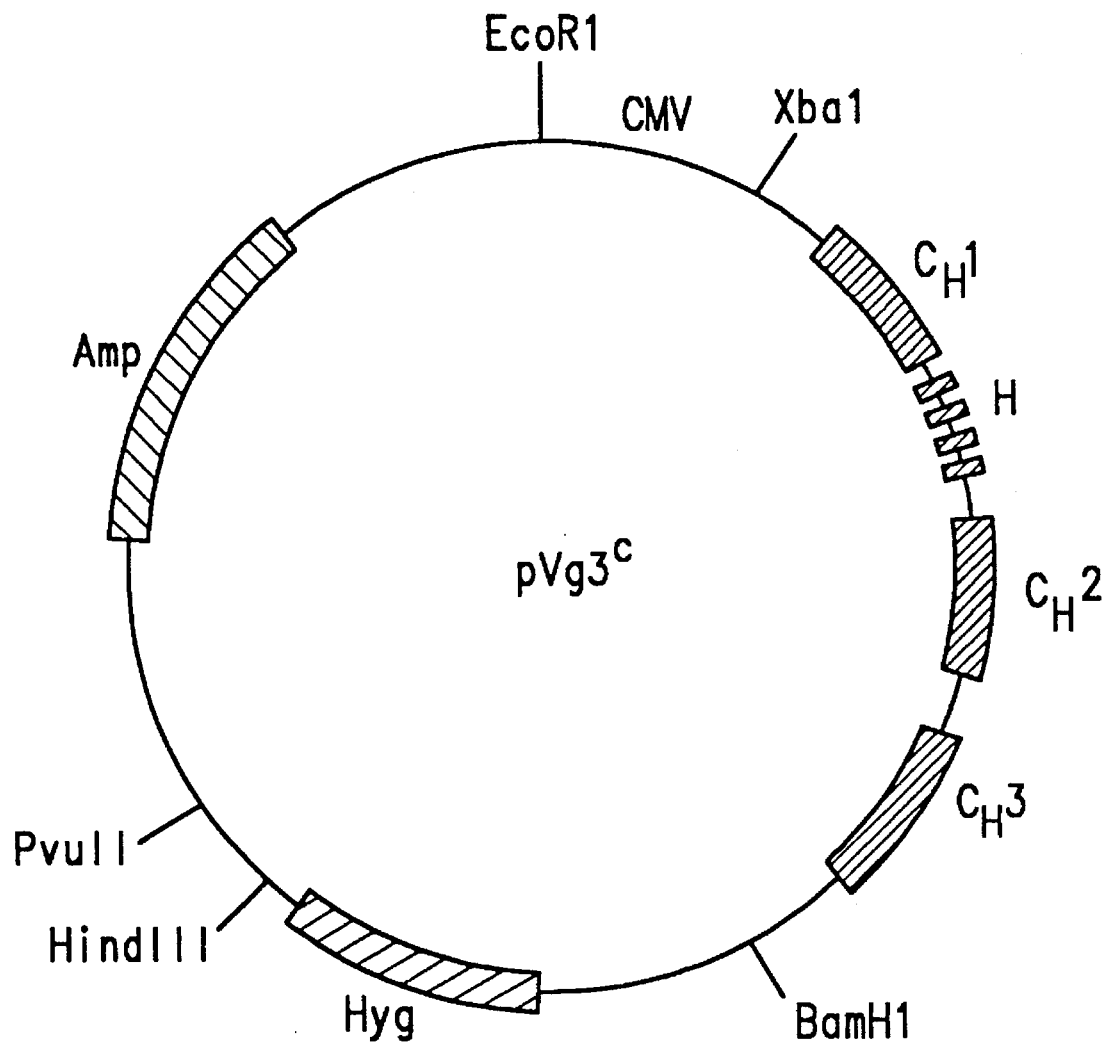

FIG. 7: Diagram of plasmid $pVg3^3$: component parts are labeled, coding regions are shown as boxes, and restriction sites used in the construction are labeled.

FIG. 8: BR55-2 light chain variable region (VL) (SEQ ID NOS:8 and 9) the nucleotide sequence and the translated amino acid sequence of the variable region segment in pVk is shown. The XbaI sites are underlined. The splice donor signal is marked by arrow. The peptide signal is also translated. The first amino acid of the mature protein is labeled 1.

FIG. 9: BR55-2 heavy chain variable region (VH) (SEQ ID NOS:10 and 11): the nucleotide sequence and the translated amino acid sequence of the variable region segment in $pVg1^c$ (or $pVg3^c$) is shown. The XbaI sites are underlined. The splice donor signal is marked by arrow. The peptide signal is also translated. The first amino acid of the mature protein is labeled 1.

Figure 10:
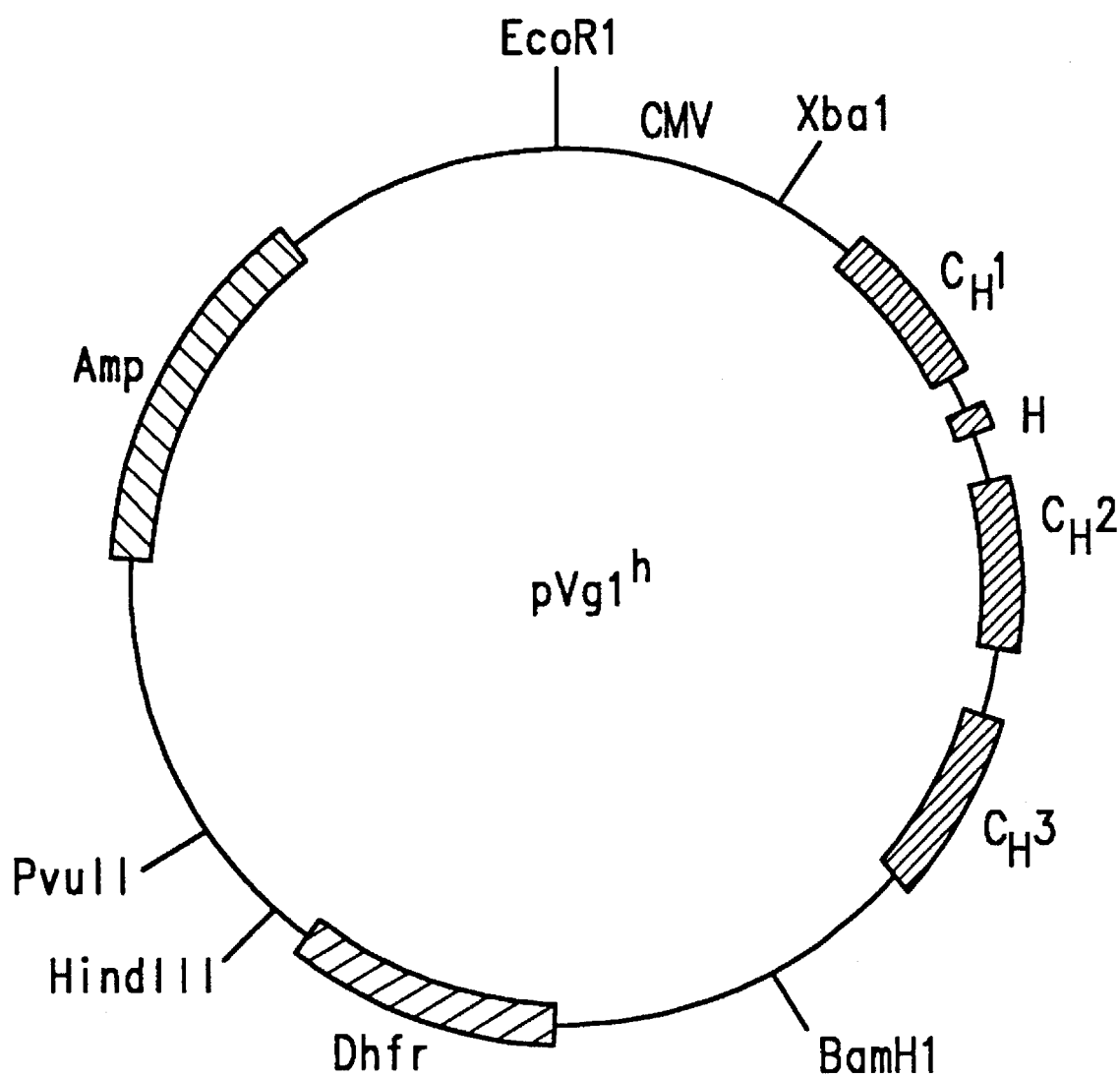

FIG. 10: Diagram of plasmid $pVg1^R$: coding regions are shown as boxes, component parts and restriction sites used in the construction are labeled.

FIG. 11: Amino acid sequence of humanized BR55-2, heavy chain variants (SEQ ID NOS:12, 13, and 14): amino acid sequence alignment of three humanized heavy chain variants. The top line shows the H-hu-BR55-2/1 sequence. Substitutions in H-hu-BR55-2/2 and H-hu-BR55-2/3 sequences are shown underneath. The CDR sequences are underlined.

FIG. 12: Amino acid sequence of humanized BR55-2, light chain comparison with Tew sequence (SEQ ID NOS:15 and 16): amino acid sequence of the light chain of the humanized BR55-2 (upper line) compared with the Tew sequence (lower line). The three CDR's are underlined. Residues in the framework that have been replaced with mouse amino acids in the humanized antibody are double underlined.

FIG. 13: Amino acid sequence of humanized BR55-2/3, heavy chain comparison with Pom sequence (SEQ ID NOS:17 and 18): amino acid sequence of the heavy chain of the humanized BR55-2/3 (upper line) compared with the Pom sequence (lower line). The three CDR's are underlined. Residues in the framework that have been replaced with mouse amino acids in the humanized antibody are double underlined.

FIG. 14: Oligonucleotides (SEQ ID NOS:19–22): the four oligonucleotides to be used for the construction of the humanized BR55-2 light chain (L-hu-BR55-2 sequence).

FIG. 15: Oligonucleotides (SEQ ID NOS:23–26): the four oligonucleotides to be used for the construction of the humanized BR55-2/3 heavy chain (H-hu-BR55-2/3 sequence).

Figure 16:
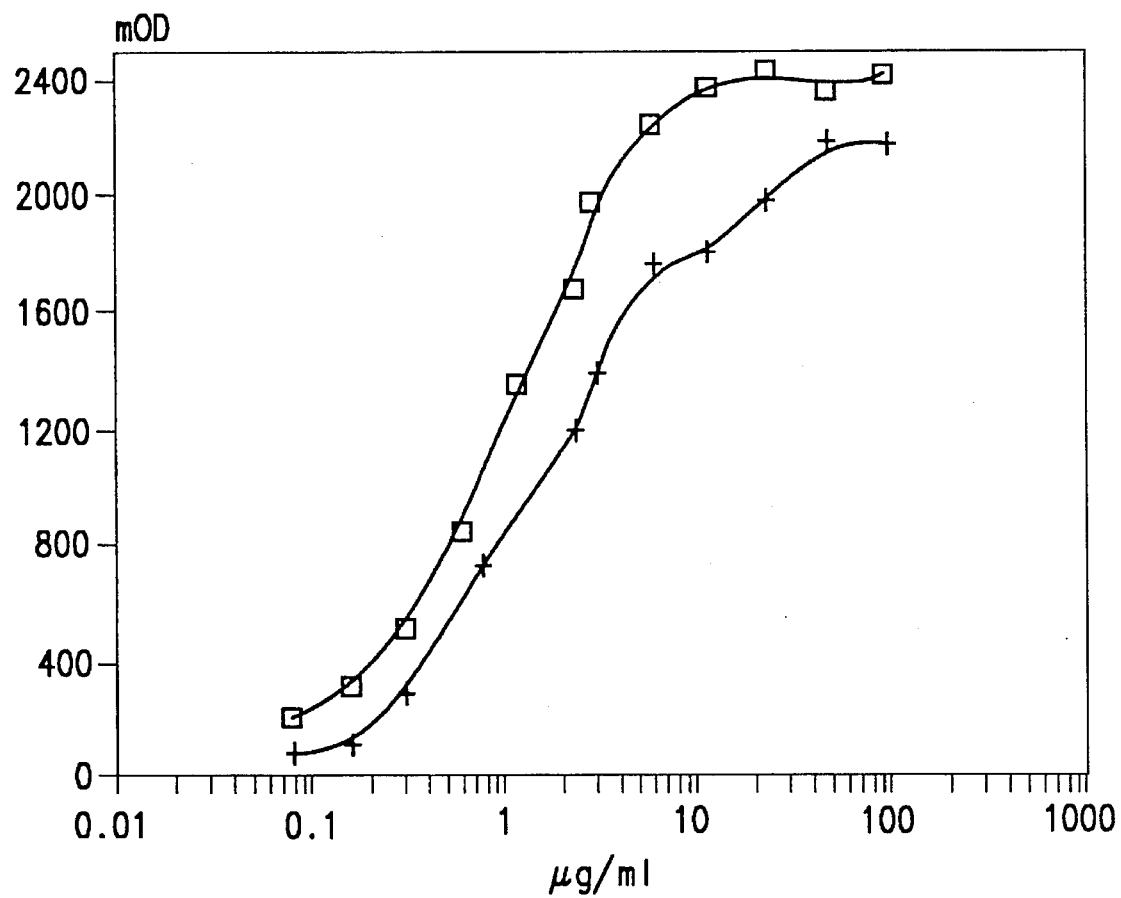

FIG. 16: Binding to SKBR5 breast cancer cell line (cell-ELISA):

crosses=BR55-2 mouse/human chimeric IgG1;

squares=BR55-2 mouse/human chimeric IgG3

Figure 17:
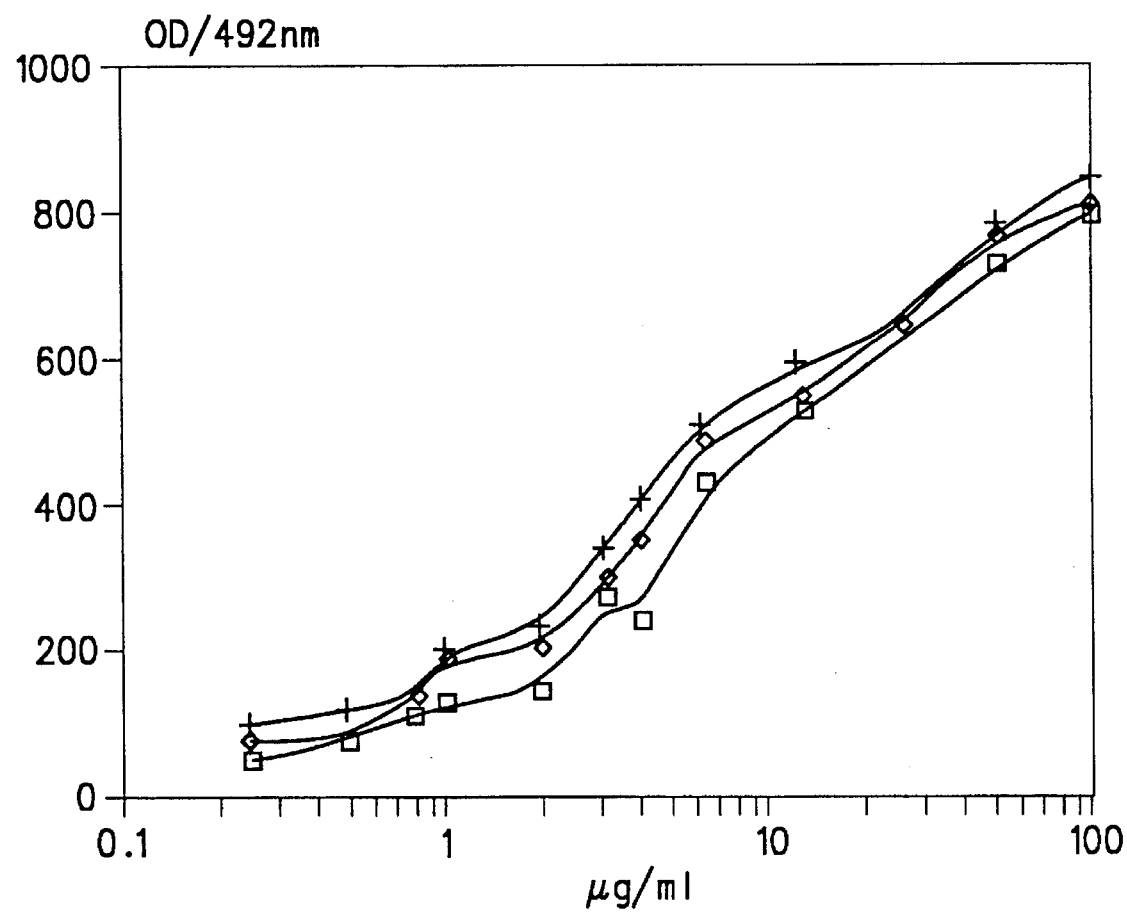

FIG. 17: Binding to SKBR5 breast cancer cell line (cell-ELISA):

crosses=BR55-2 mouse/human chimeric IgG1;

squares=BR55-2 humanized IgG1/2;

losanges=BR55-2 humanized IgG1/3.

Figure 18:
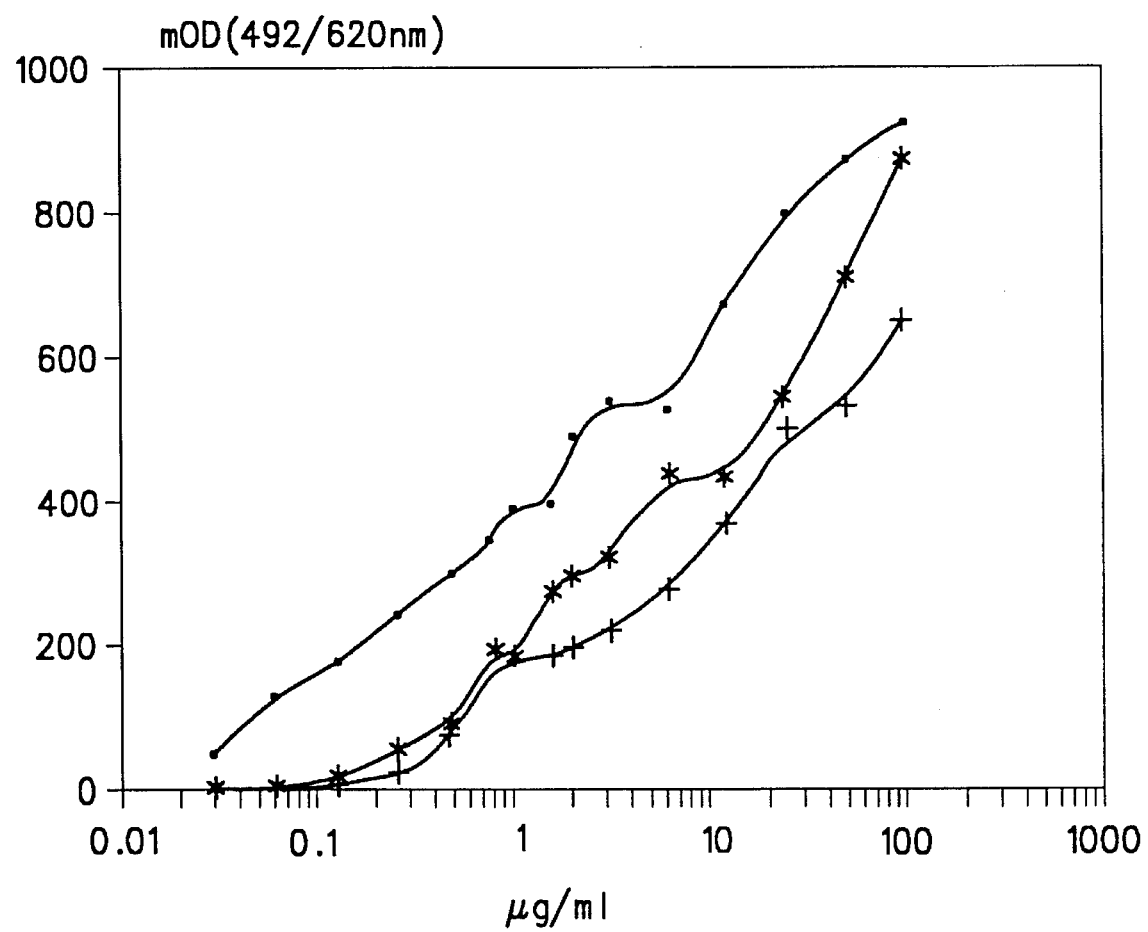

FIG. 18: Binding to SKBR5 breast cancer cell line (cell-ELISA):

crosses=BR55-2 humanized IgG2;

dots=BR55-2 humanized IgG3;

asterisks=BR55-2 humanized IgG4.

Figure 19:
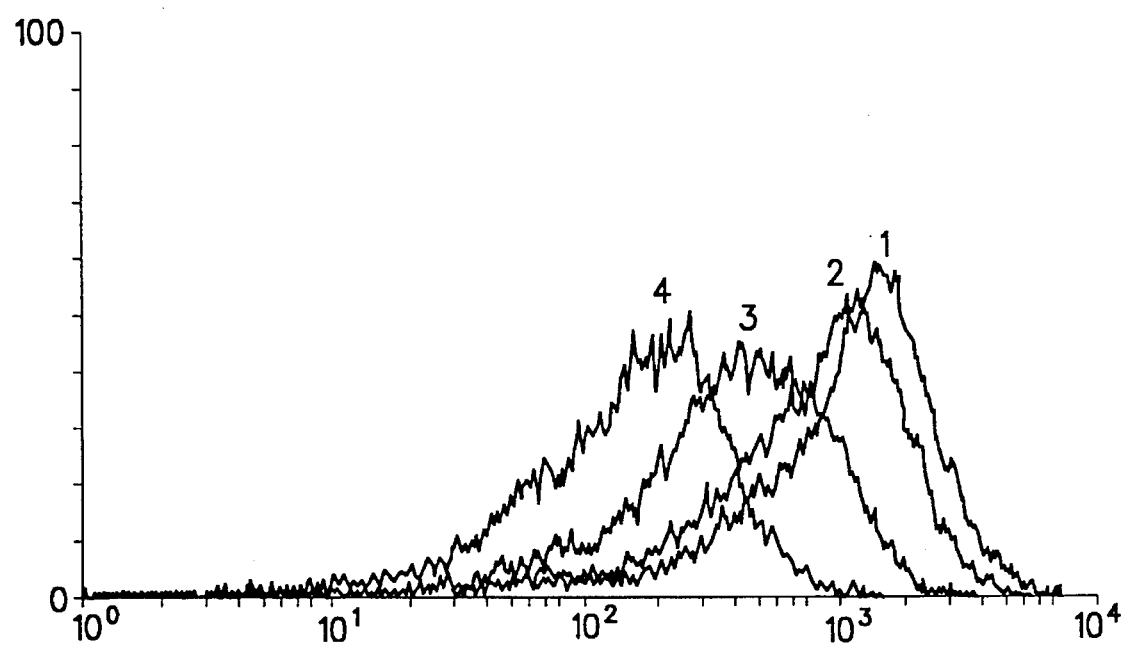
Figure 20:
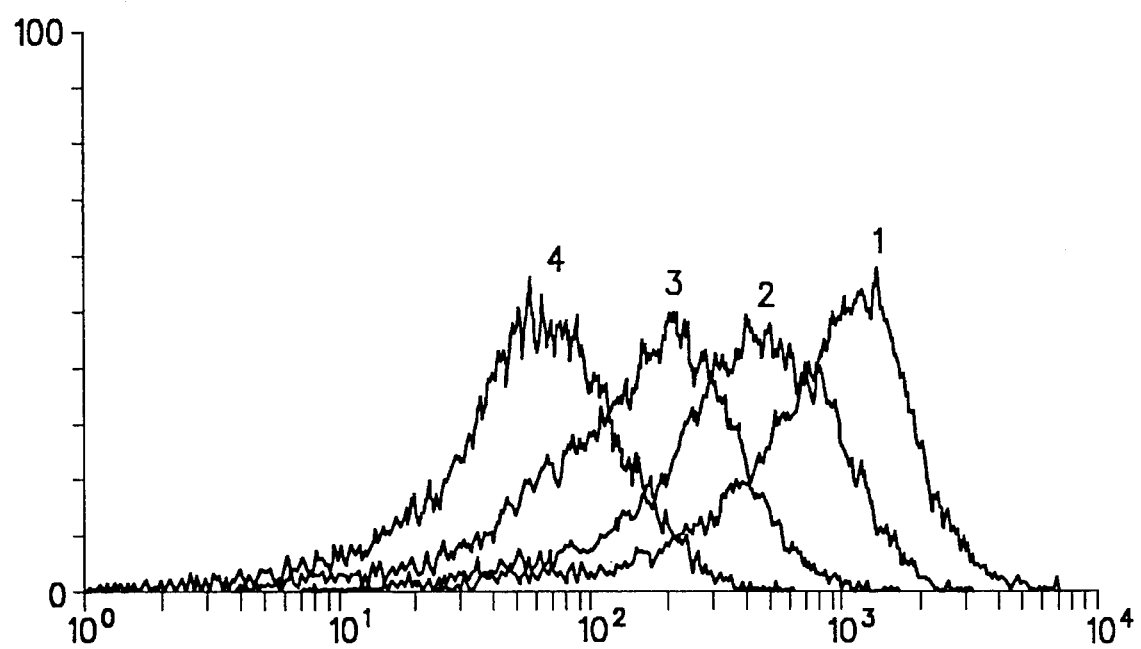
Figure 21:
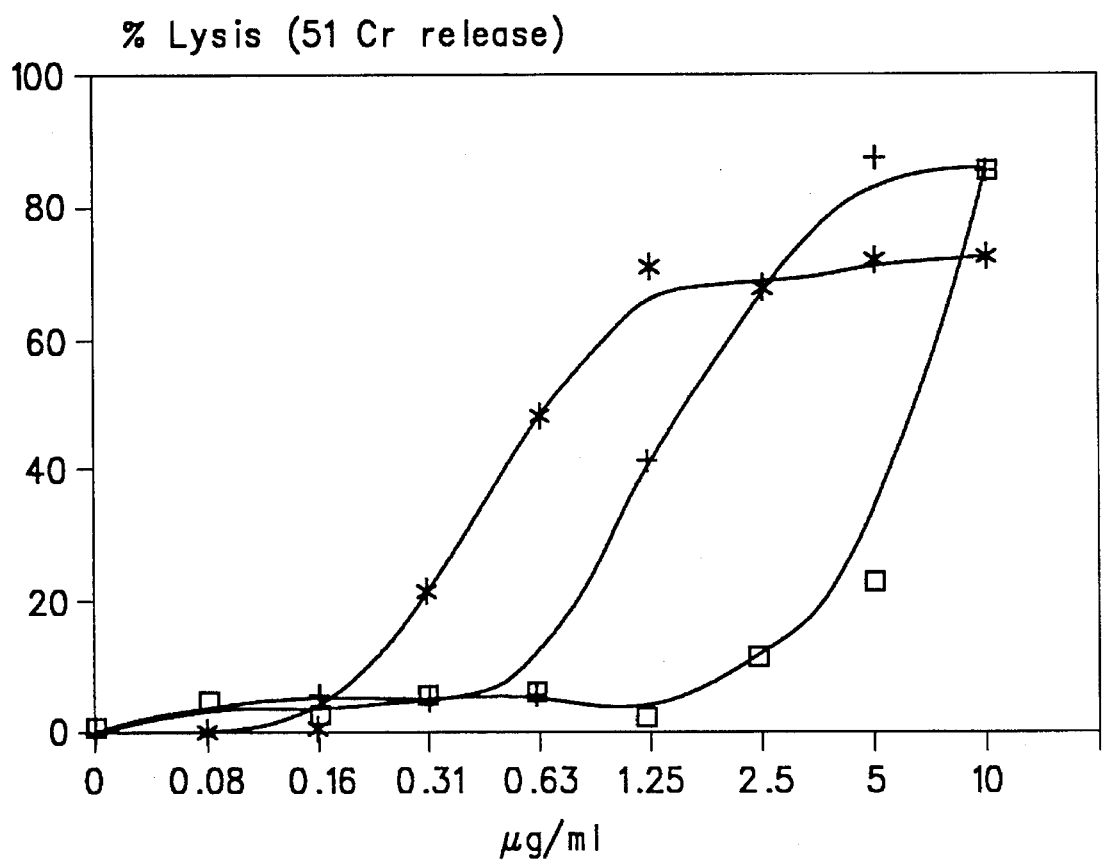
Figure 22:
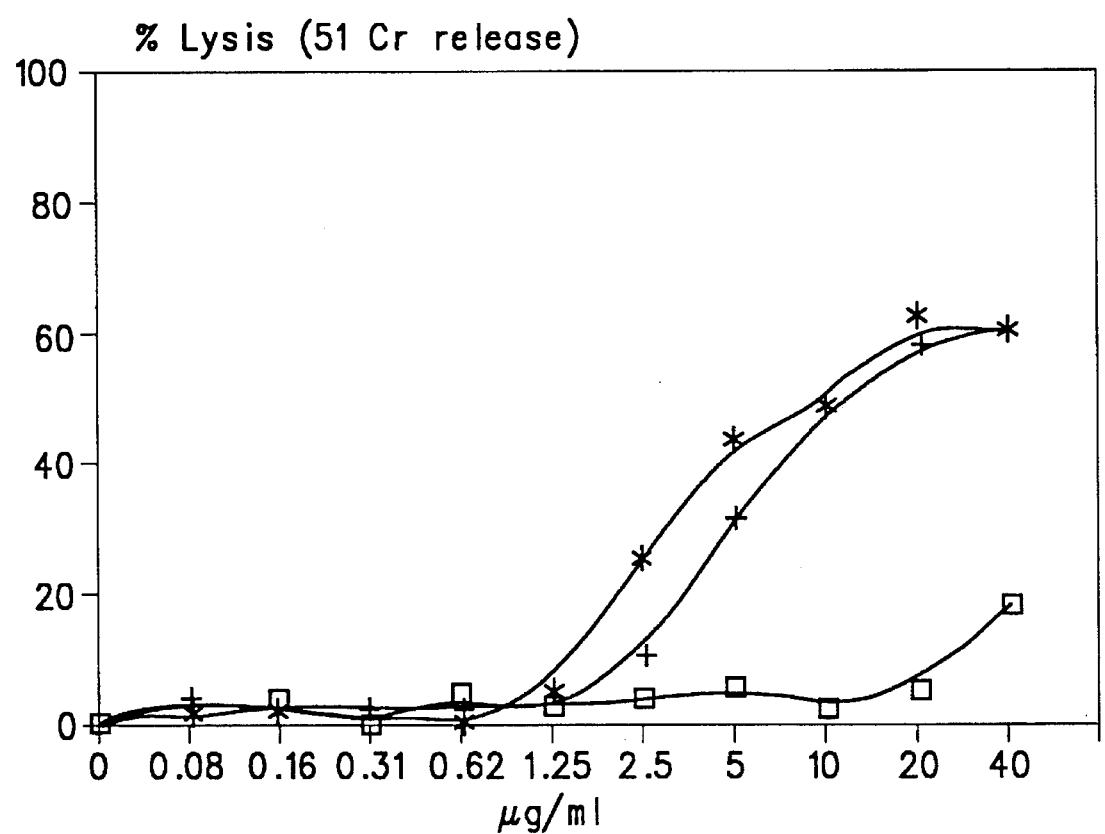
Figure 23:
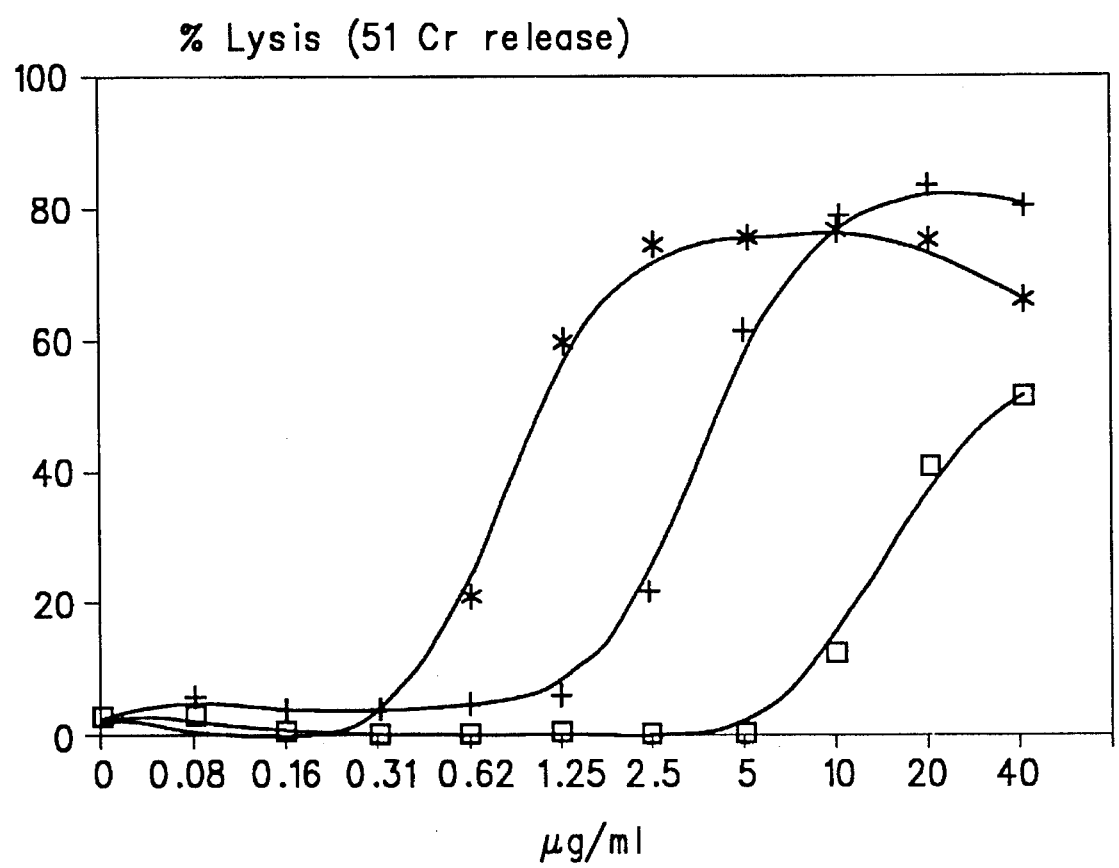
Figure 24:
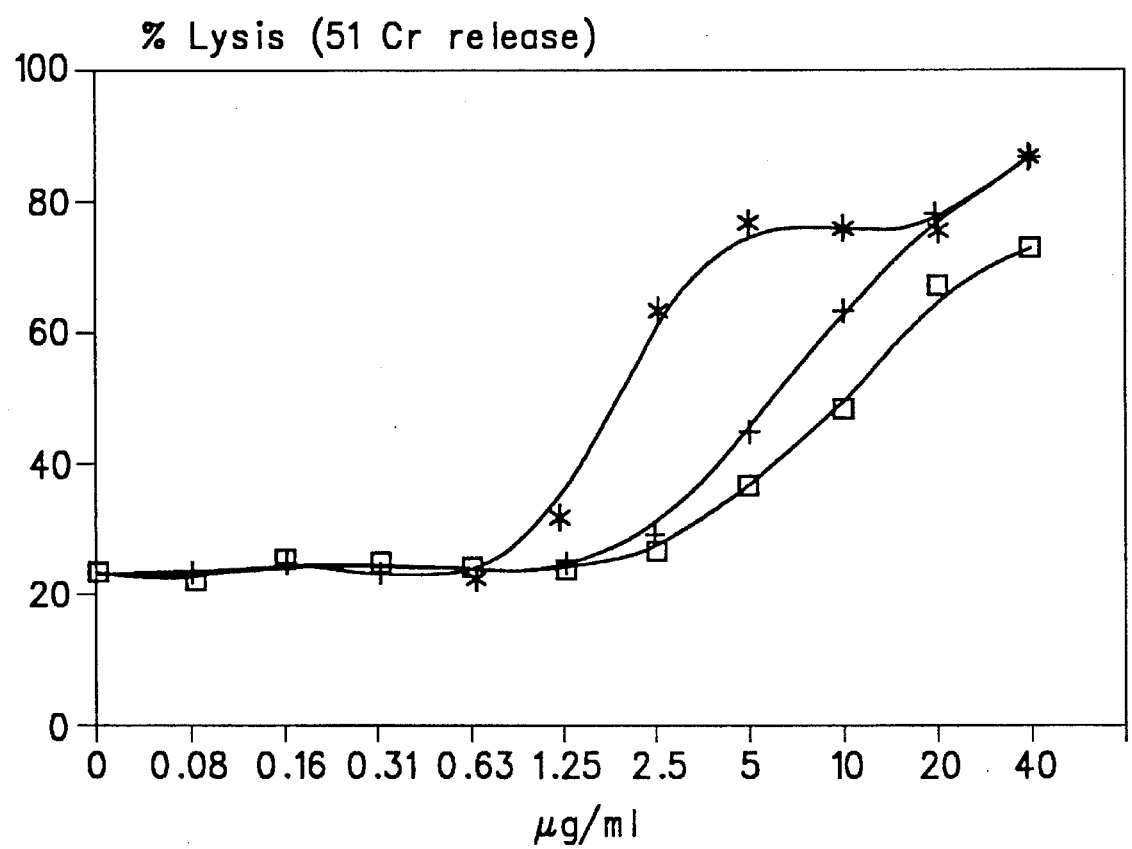
Figure 25:
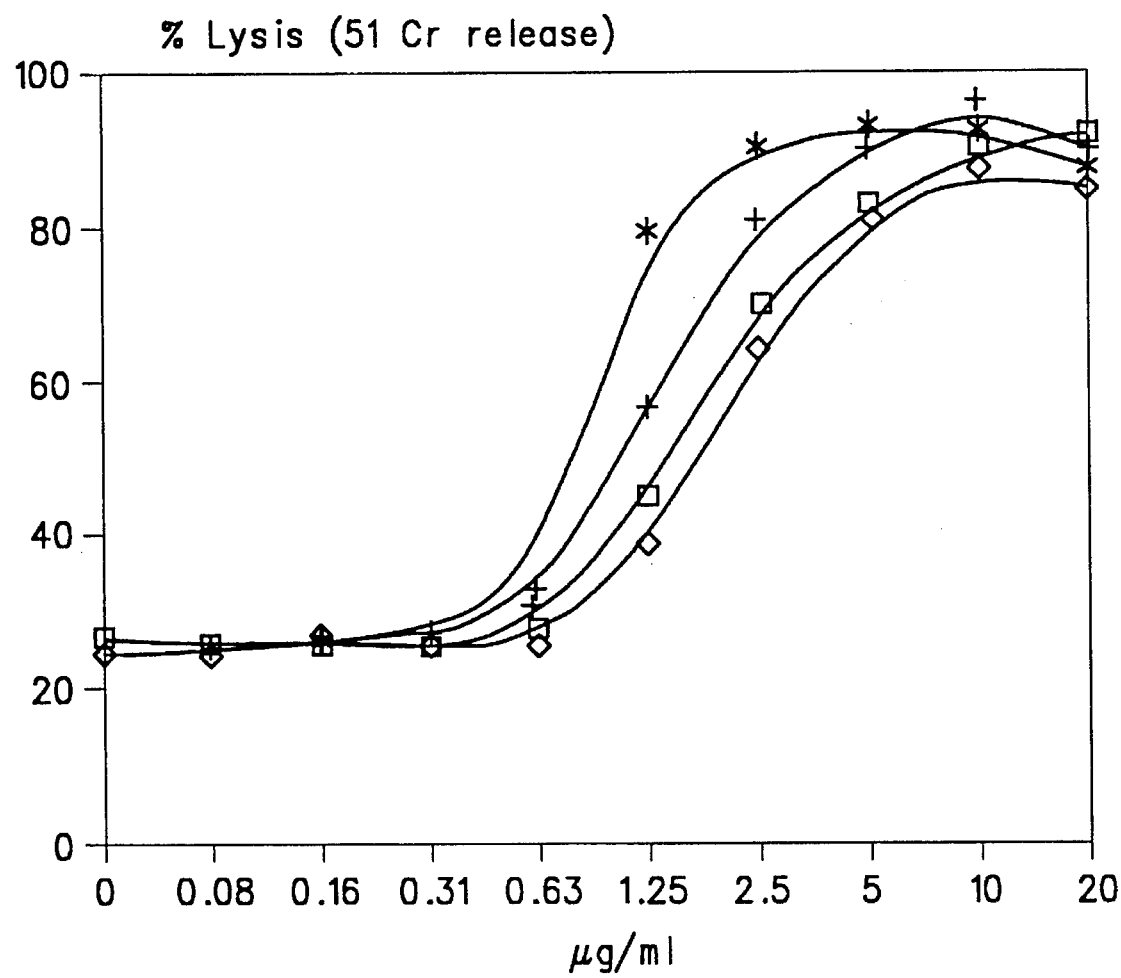
Figure 26:
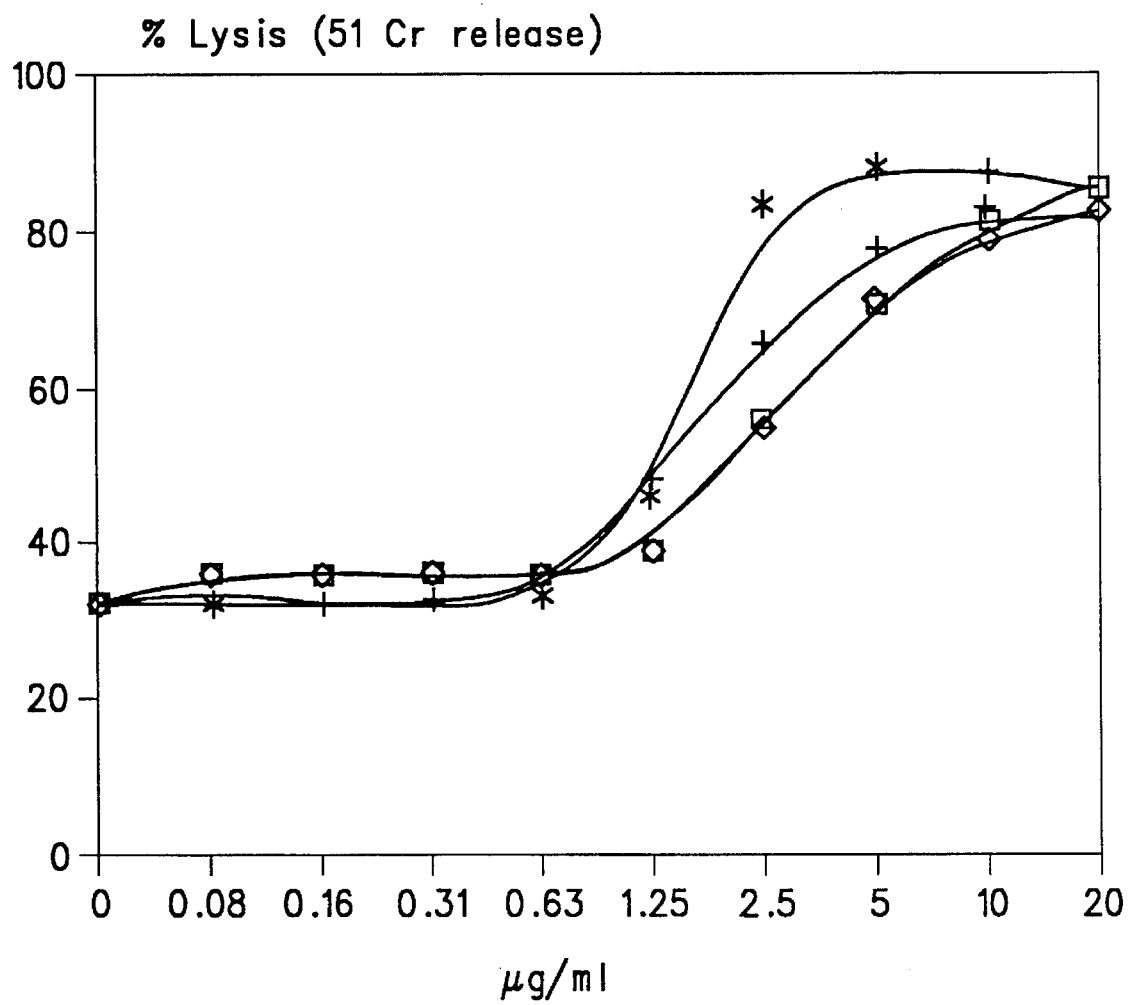
Figure 27:
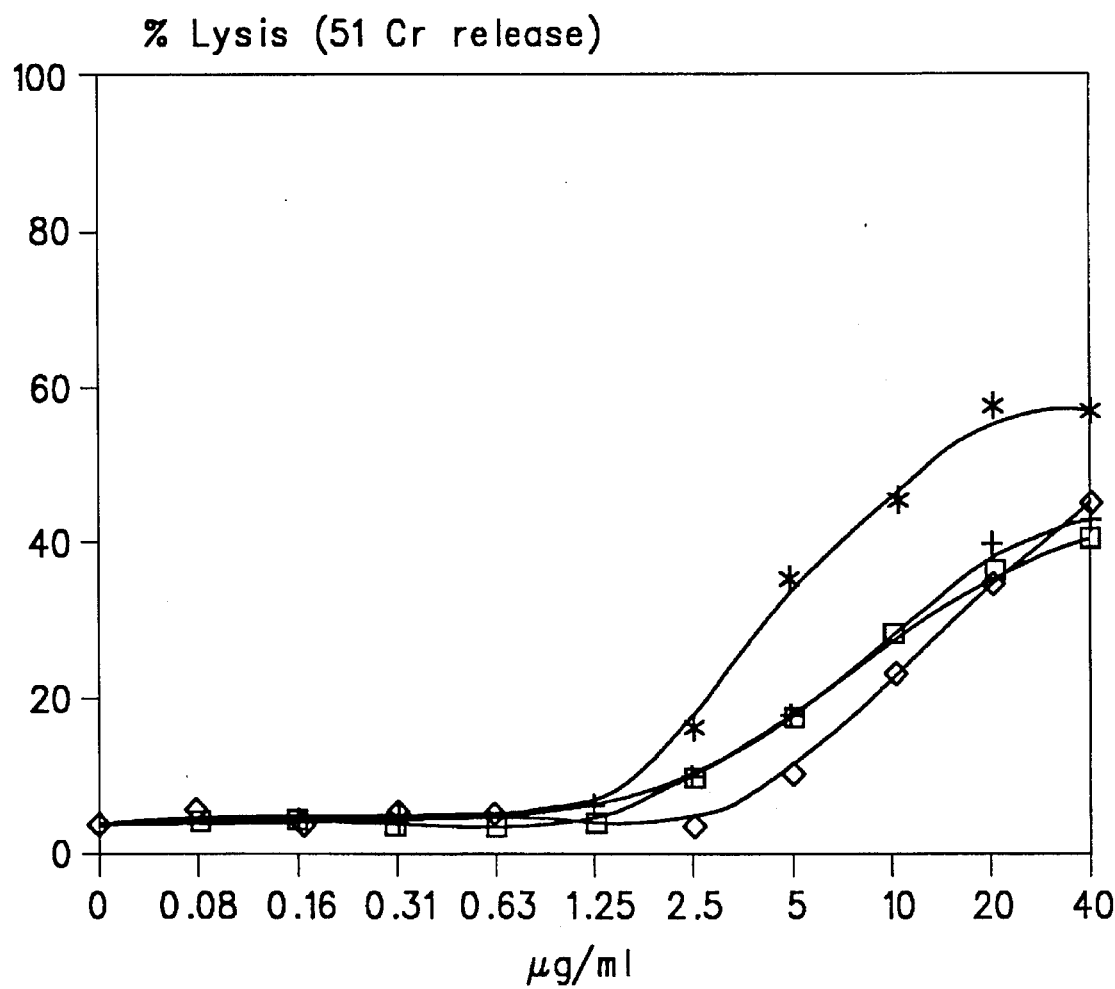
Figure 28:
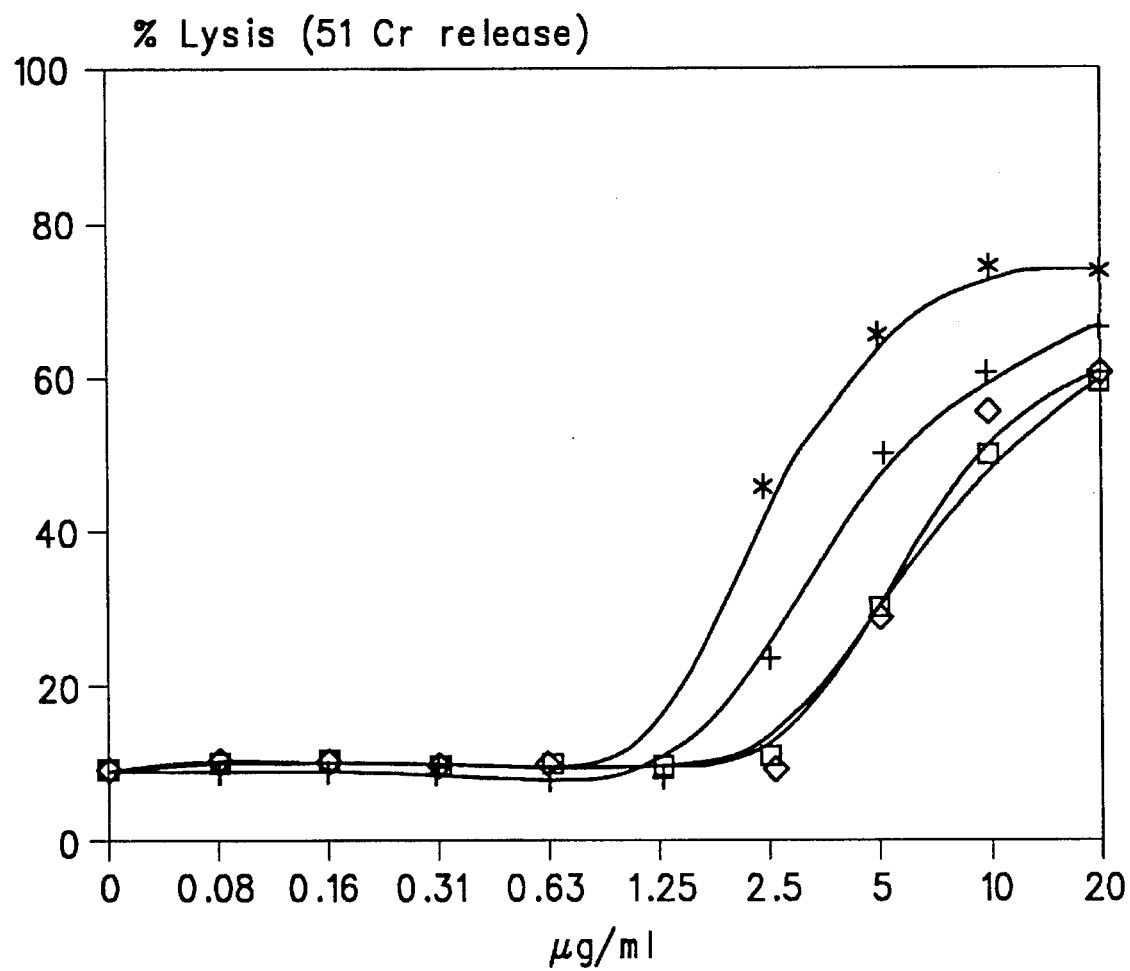
Figure 29:
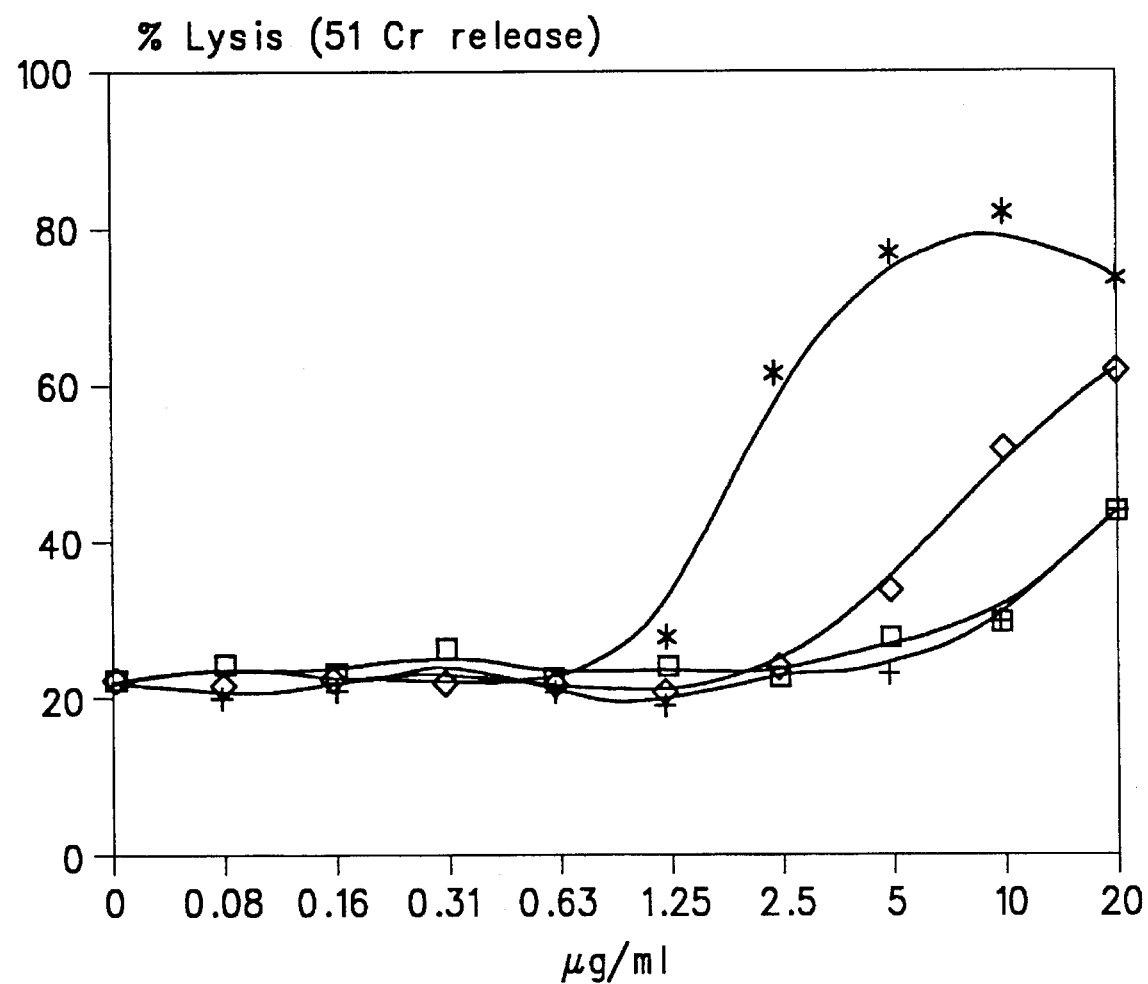
Figure 30:
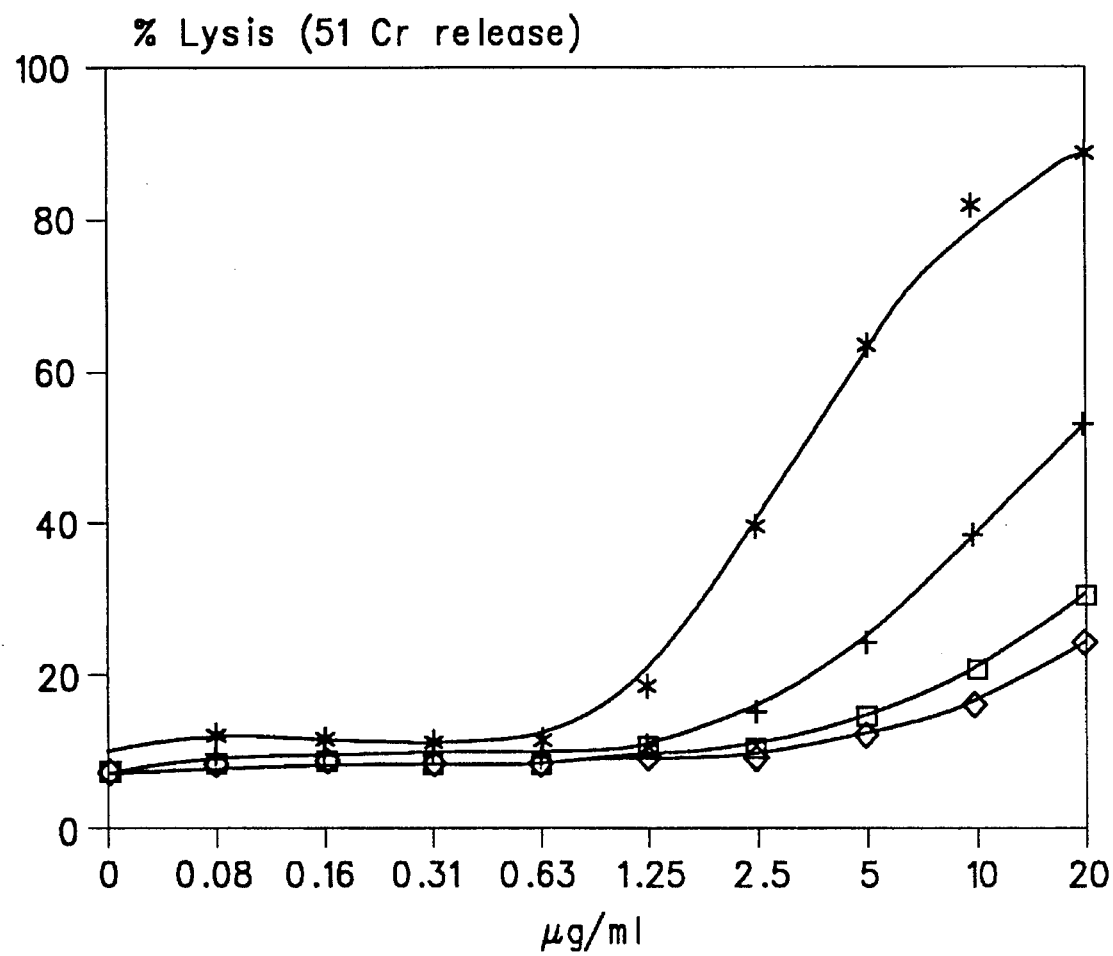
Figure 31:
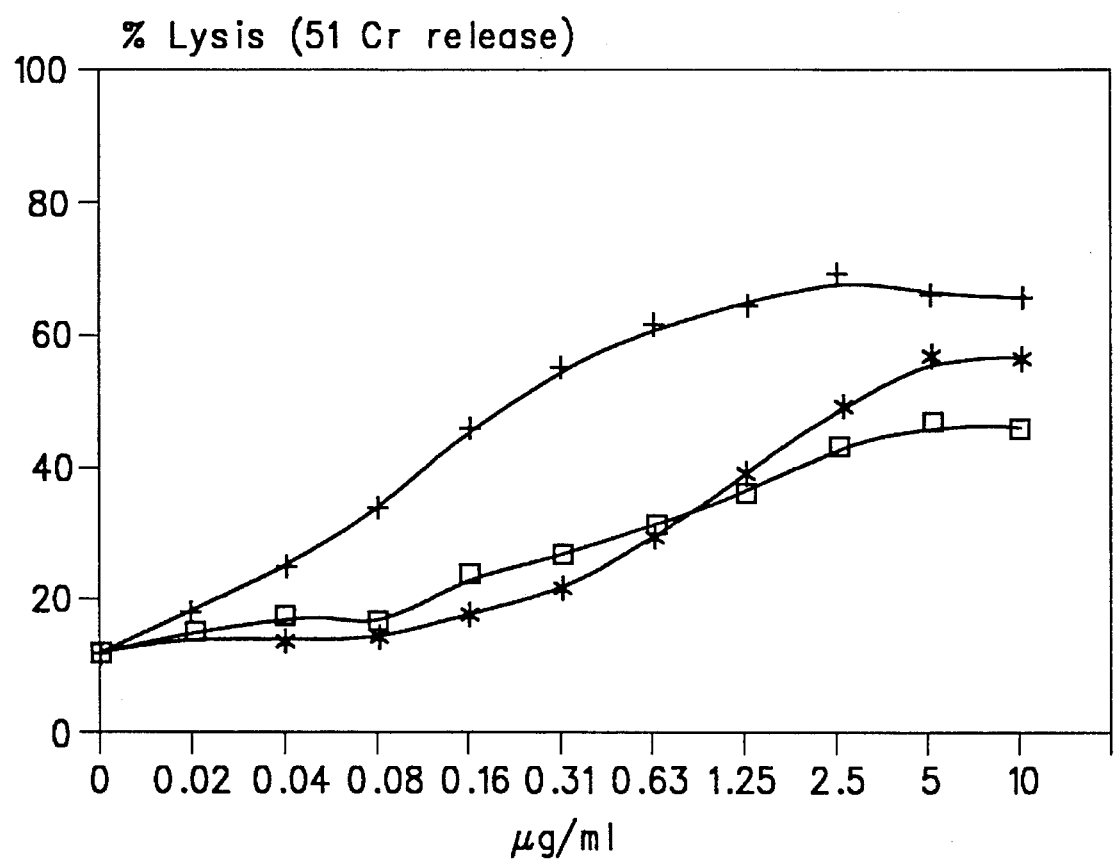
Figure 32:
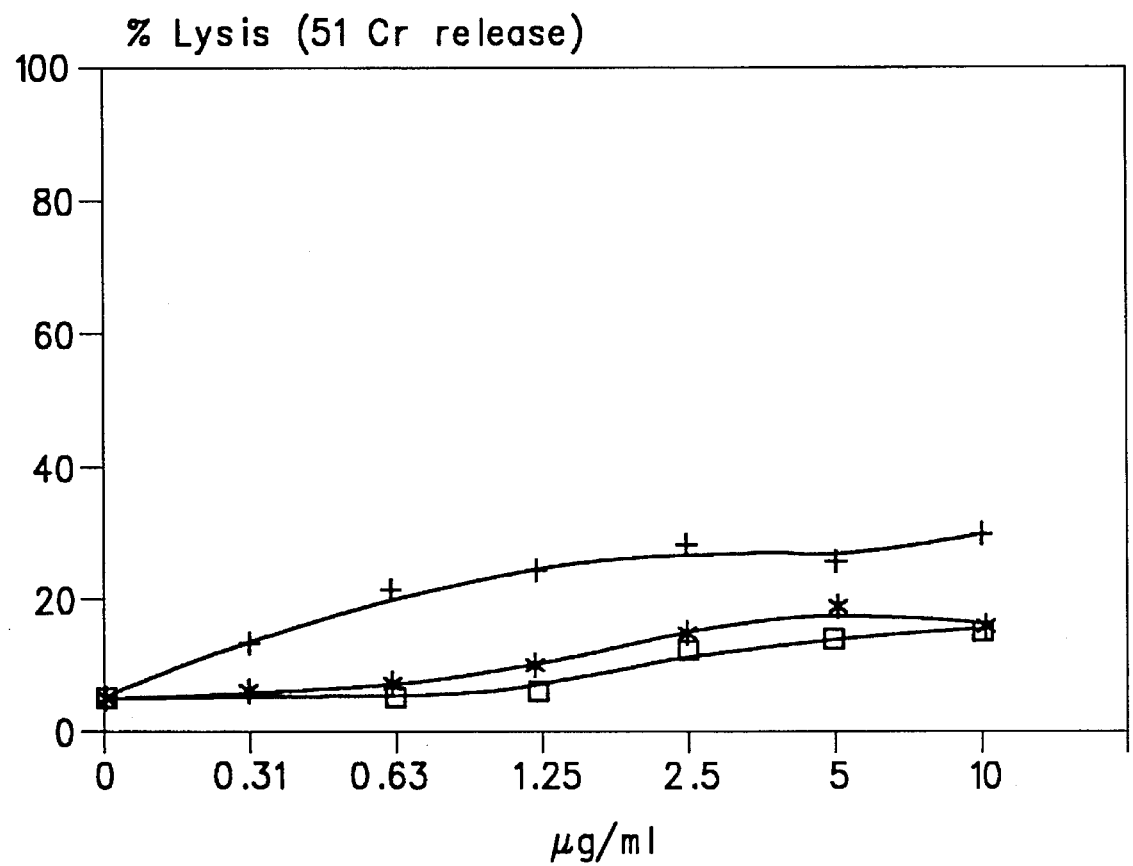
Figure 33:
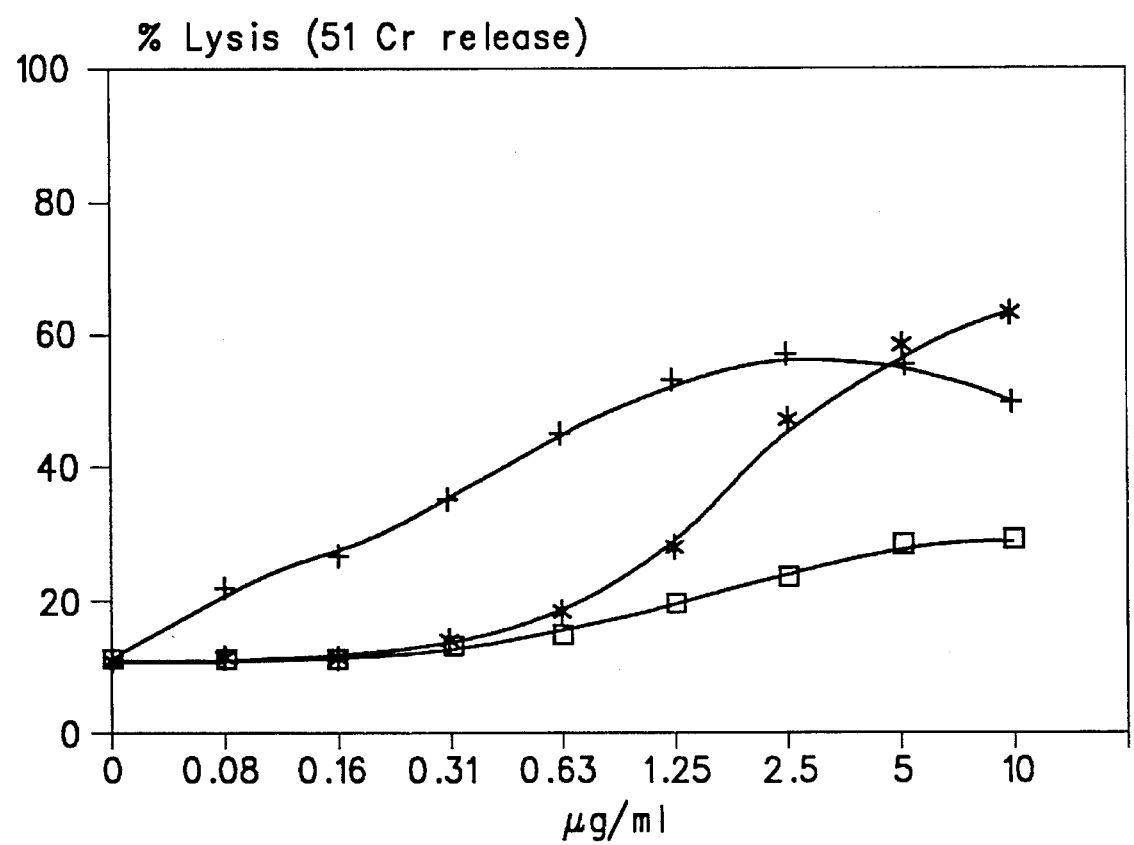
Figure 34:
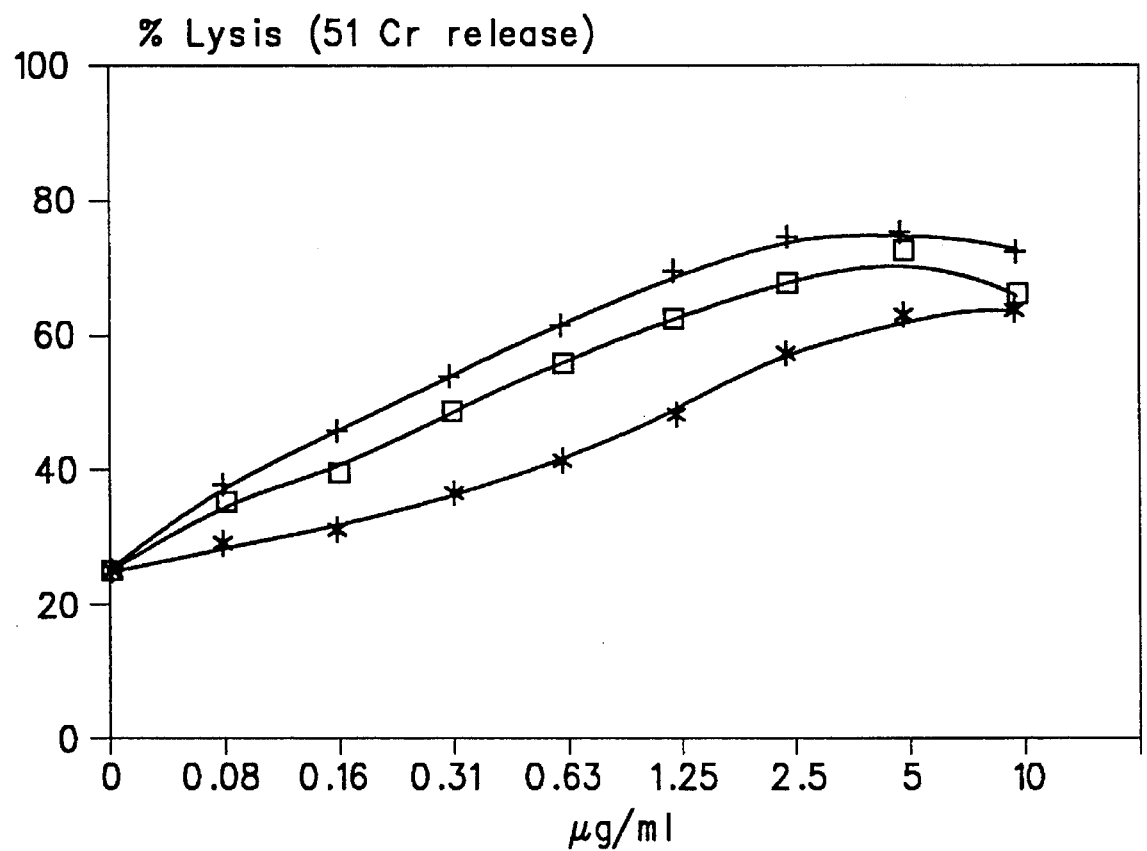
Figure 35:
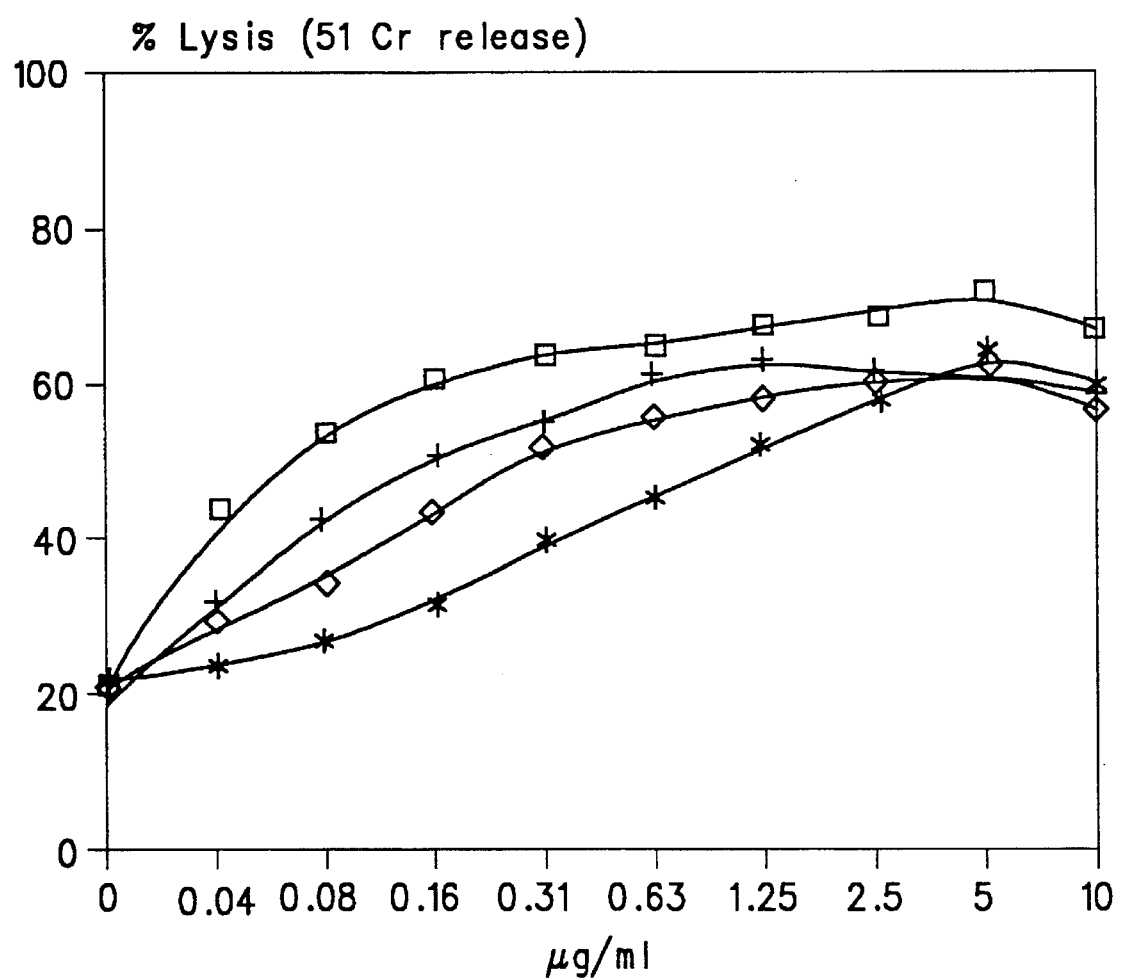
Figure 36:
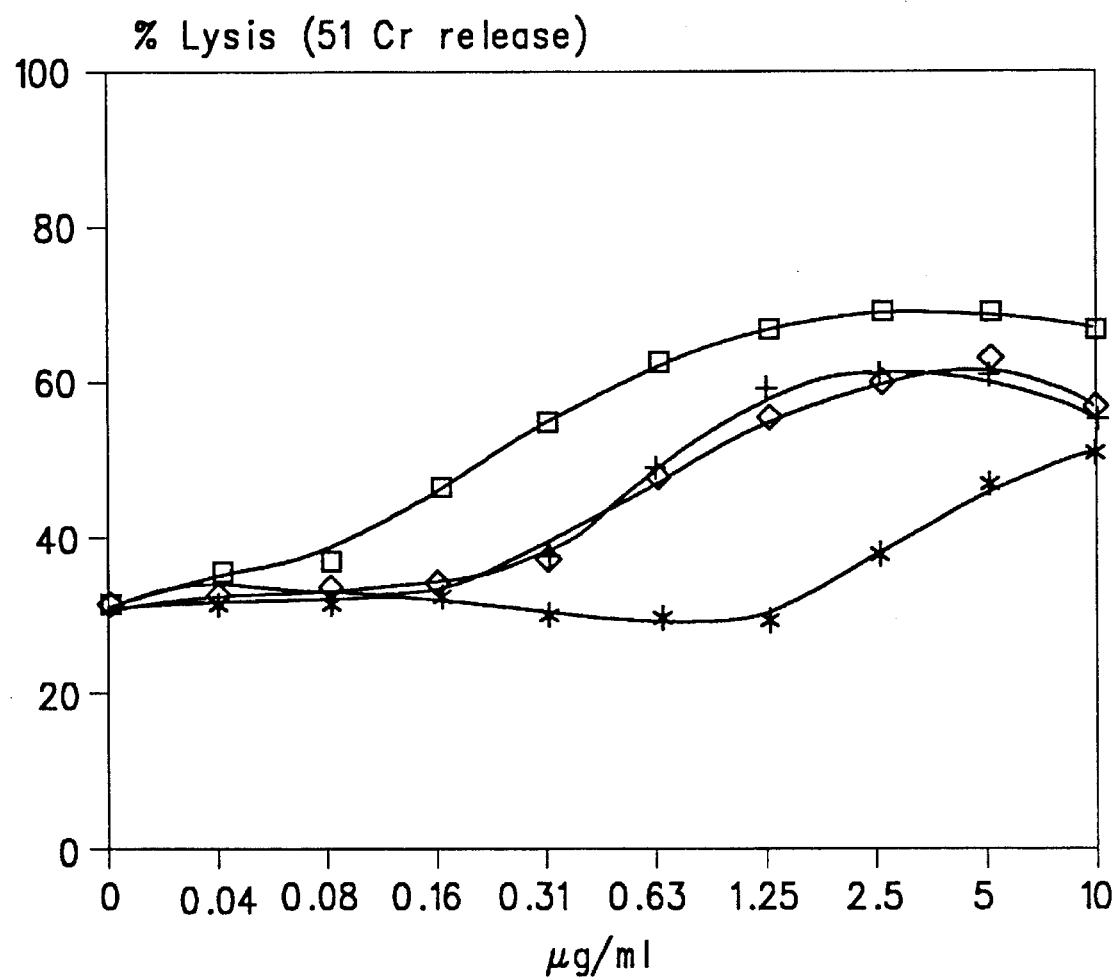
Figure 37:
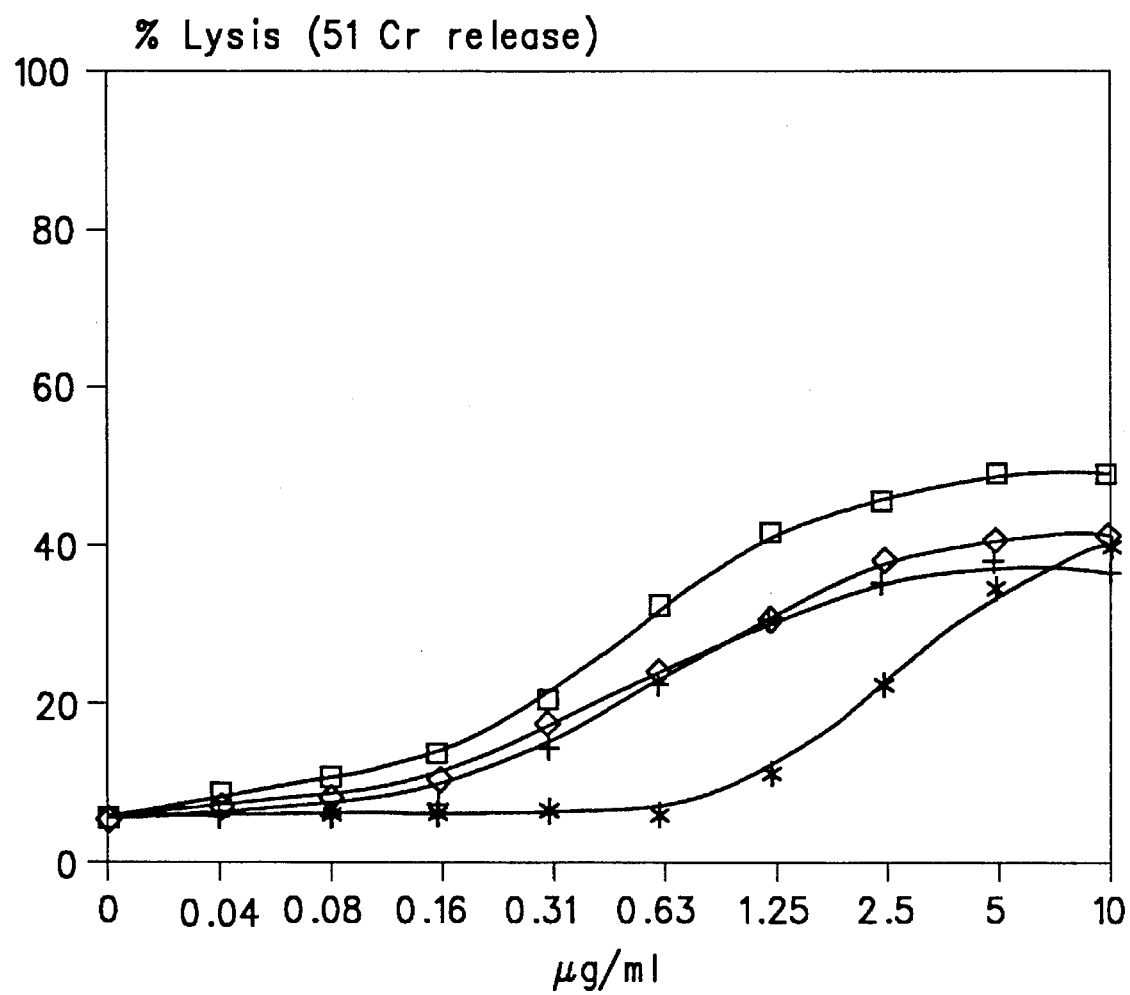
Figure 38:
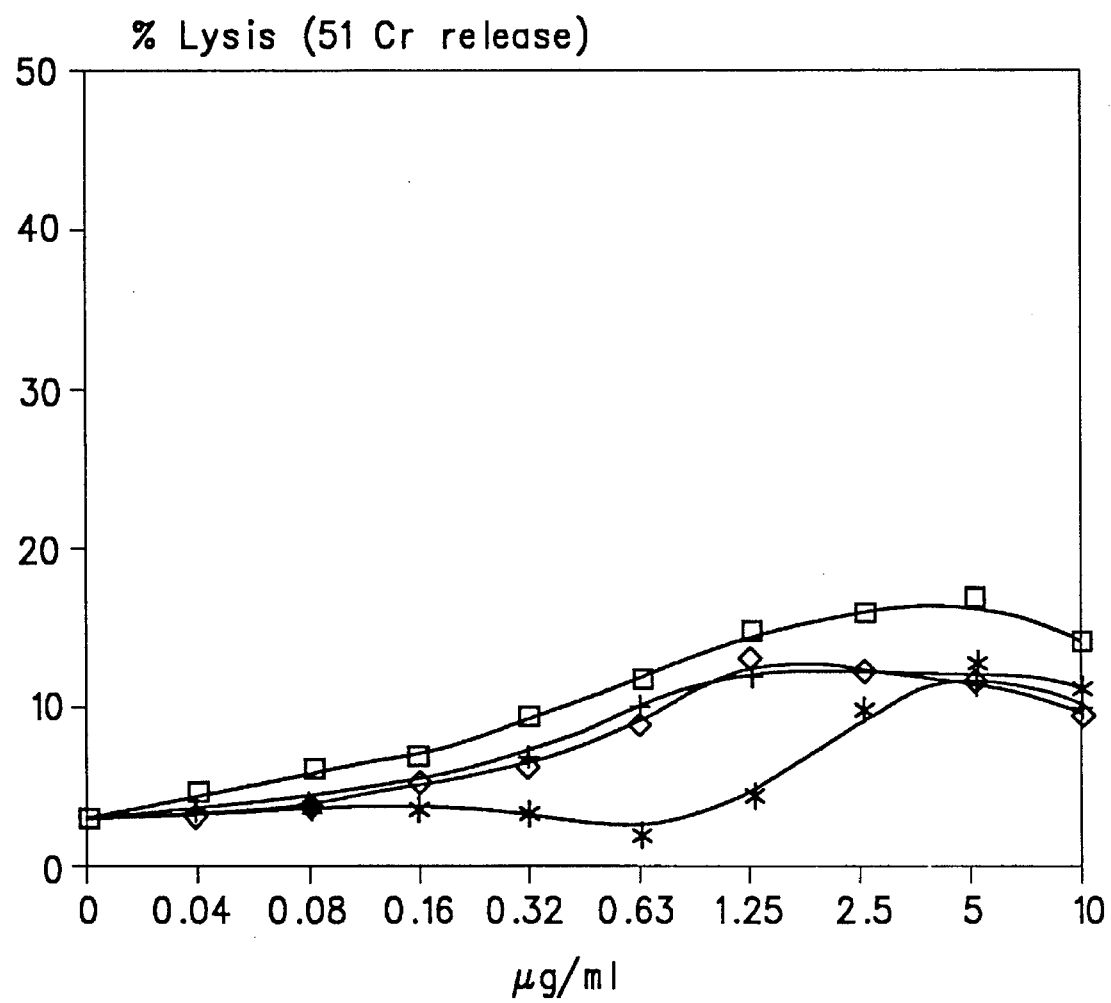
Figure 39:
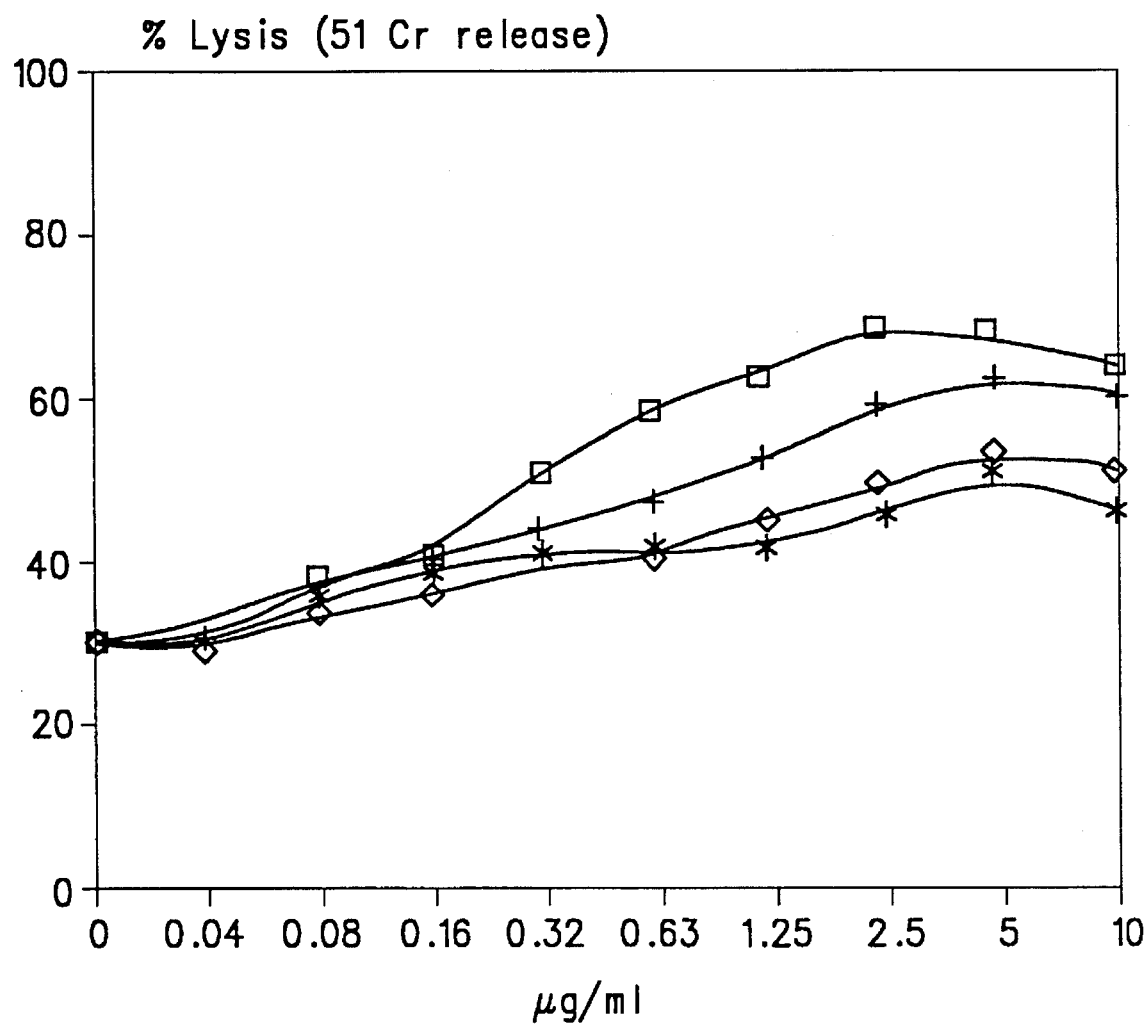

FIG. 19: Binding to SKBR5 breast cancer cell line (fluorescence-activated flow cytometry):

1=60 μg BR55-2 mouse/human chimeric IgG1;
2=15 μg BR55-2 mouse/human chimeric IgG1;
3=3.75 μg BR55-2 mouse/human chimeric IgG1;
4=0.94 μg BR55-2 mouse/human chimeric IgG1;
FIG. 20: Binding to SKBR5 breast cancer cell line (fluorescence-activated flow cytometry):
1=60 μg BR55-2 humanized IgG3;
2=15 μg BR55-2 humanized IgG3;
3=3.75 μg BR55-2 humanized IgG3;
4=0.94 μg BR55-2 humanized IgG3;
FIG. 21: CDC to SKBR5 breast cancer cell line: complement-dependent cytotoxicity with human serum (1:2.5):
asterisks=BR55-2 mouse IgG3;
crosses=BR55-2 mouse/human chimeric IgG1;
squares=BR55-2 mouse/human chimeric IgG3.
FIG. 22: CDC to SW948 colon cancer cell line: complement-dependent cytotoxicity with human serum (1:2.5):
asterisks=BR55-2 mouse IgG3;
crosses=BR55-2 mouse/human chimeric IgG1;
squares=BR55-2 mouse/human chimeric IgG3.
FIG. 23: CDC to CATO gastric cancer cell line: complement-dependent cytotoxicity with human serum (1:2.5):
asterisks=BR55-2 mouse IgG3;
crosses=BR55-2 mouse/human chimeric IgG1;
squares=BR55-2 mouse/human chimeric IgG3.
FIG. 24: CDC to SW2 small cell lung cancer cell line: complement-dependent cytotoxicity with human serum (1:2.5):
asterisks=BR55-2 mouse IgG3;
crosses=BR55-2 mouse/human chimeric IgG1;
squares=BR55-2 mouse/human chimeric IgG3.
FIG. 25: CDC to SKBR5 breast cancer cell line: complement-dependent cytotoxicity with human serum (1:2.5):
asterisks=BR55-2 mouse IgG3;
crosses=BR55-2 mouse/human chimeric IgG1;
squares=BR55-2 humanized IgG1/2;
losanges=BR55-2 humanized IgG1/3.
FIG. 26: CDC to SKBR5 breast cancer cell line: complement-dependent cytotoxicity with human serum (1:2.5):
asterisks=BR55-2 mouse IgG3;
crosses=BR55-2 mouse/human chimeric IgG1;
squares=BR55-2 humanized IgG1/2;
losanges=BR55-2 humanized IgG1/3.
FIG. 27: CDC to MCF7 breast cancer cell line: complement-dependent cytotoxicity with human serum (1:2.5):
asterisks=BR55-2 mouse IgG3;
crosses=BR55-2 mouse/human chimeric IgG1;
squares=BR55-2 humanized IgG1/2;
losanges=BR55-2 humanized IgG1/3.
FIG. 28: CDC to SW948 colon cancer cell line: complement-dependent cytotoxicity with human serum (1:2.5):
asterisks=BR55-2 mouse IgG3;
crosses=BR55-2 mouse/human chimeric IgG1;
squares=BR55-2 humanized IgG1/2;
losanges=BR55-2 humanized IgG1/3.
FIG. 29: CDC to CATO gastric cancer cell line: complement-dependent cytotoxicity with human serum (1:2.5):
asterisks=BR55-2 mouse IgG3;
crosses=BR55-2 mouse/human chimeric IgG1;
squares=BR55-2 humanized IgG1/2;
losanges=BR55-2 humanized IgG1/3.
FIG. 30: CDC to SW2 small cell lung cancer cell line: complement-dependent cytotoxicity with human serum (1:2.5):
asterisks=BR55-2 mouse IgG3;
crosses=BR55-2 mouse/human chimeric IgG1;
squares=BR55-2 humanized IgG1/2;
losanges=BR55-2 humanized IgG1/3.
FIG. 31: ADCC to SKBR5 breast cancer cell line: antibody dependent cellular cytotoxicity with human PBMC (E:T=15:1):
asterisks=BR55-2 mouse IgG3;
crosses=BR55-2 mouse/human chimeric IgG1;
squares=BR55-2 mouse/human chimeric IgG3.
FIG. 32: ADCC to SW 948 colon cancer cell line: antibody dependent cellular cytotoxicity with human PBMC (E:T=15:1):
asterisks=BR55-2 mouse IgG3;
crosses=BR55-2 mouse/human chimeric IgG1;
squares=BR55-2 mouse/human chimeric IgG3.
FIG. 33: ADCC to CATO gastric cancer cell line: antibody dependent cellular cytotoxicity with human PBMC (E:T=15:1):
asterisks=BR55-2 mouse IgG3;
crosses=BR55-2 mouse/human chimeric IgG1;
squares=BR55-2 mouse/human chimeric IgG3.
FIG. 34: ADCC to MCF 7 breast cancer cell line: antibody dependent cellular cytotoxicity with human PBMC (E:T=15:1):
asterisks=BR55-2 mouse IgG3;
crosses=BR55-2 mouse/human chimeric IgG1;
squares=BR55-2 mouse/human chimeric IgG3.
FIG. 35: ADCC to SKBR5 breast cancer cell line: antibody dependent cellular cytotoxicity with human PBMC (E:T=15:1):
asterisks=BR55-2 mouse IgG3;
crosses=BR55-2 mouse/human chimeric IgG1;
squares=BR55-2 humanized IgG1/2;
losanges=BR55-2 humanized IgG1/3.
FIG. 36: ADCC to SKBR5 breast cancer cell line: antibody dependent cellular cytotoxicity with human PBMC (E:T=15:1):
asterisks=BR55-2 mouse IgG3;
crosses=BR55-2 mouse/human chimeric IgG1;
squares=BR55-2 humanized IgG1/2;
losanges=BR55-2 humanized IgG1/3.
FIG. 37: ADCC to MCF7 breast cancer cell line: antibody dependent cellular cytotoxicity with human PBMC (E:T=15:1):
asterisks=BR55-2 mouse IgG3;
crosses=BR55-2 mouse/human chimeric IgG1;
squares=BR55-2 humanized IgG1/2;
losanges=BR55-2 humanized IgG1/3.
FIG. 38: ADCC to SW948 colon cancer cell line: antibody dependent cellular cytotoxicity with human PBMC (E:T=15:1):
asterisks=BR55-2 mouse IgG3;
crosses=BR55-2 mouse/human chimeric IgG1;
squares=BR55-2 humanized IgG1/2;
losanges=BR55-2 humanized IgG1/3.
FIG. 39: ADCC to SW2 small cell lung cancer cell line: antibody dependent cellular cytotoxicity with human PBMC (E:T=15:1):

asterisks=BR55-2 mouse IgG3;
crosses=BR55-2 mouse/human chimeric IgG1;
squares=BR55-2 humanized IgG1/2;
losanges=BR55-2 humanized IgG1/3.

Figure 40:
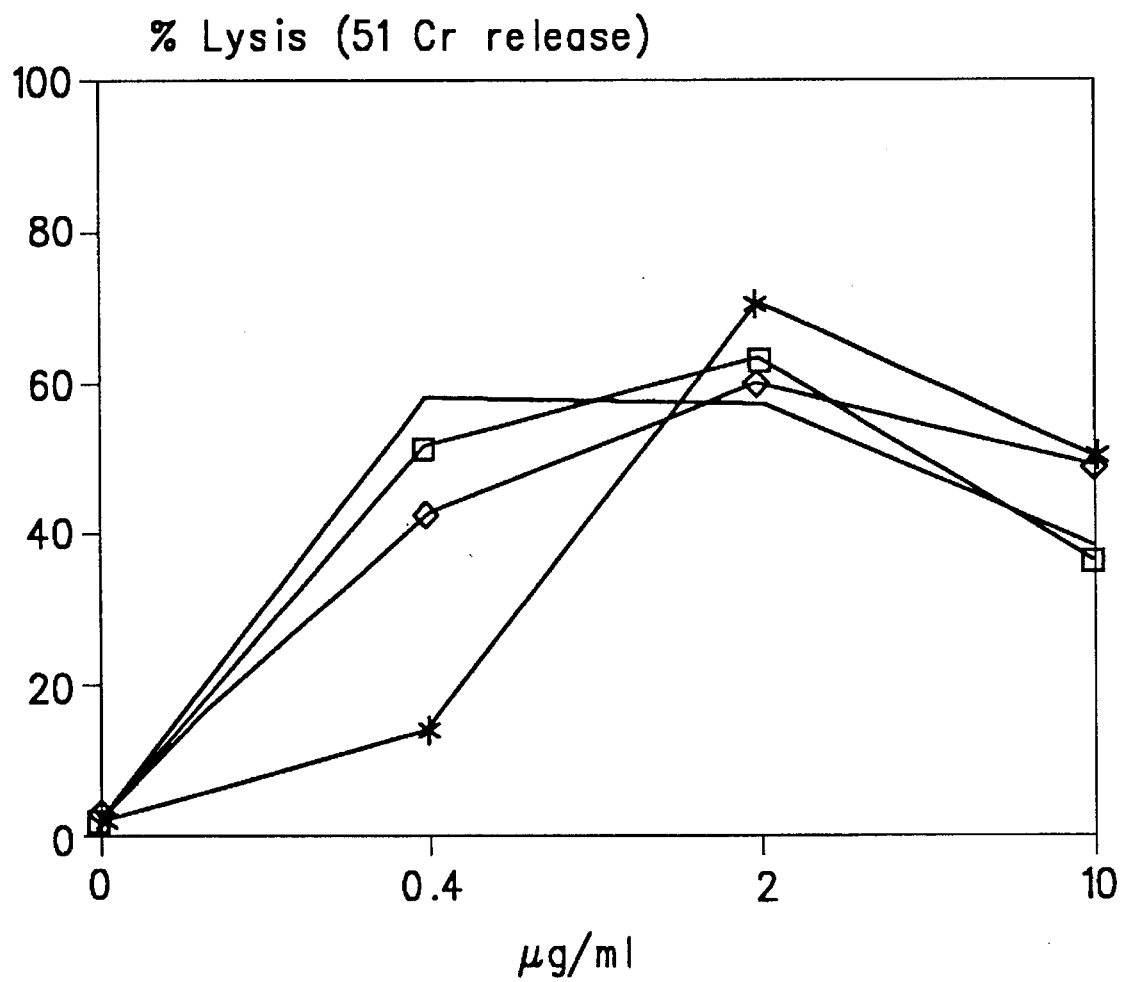

FIG. 40: Human monocyte ADCC to SKBR5 breast cancer cell line: antibody dependent cellular cytotoxicity with human monocytes (E:T=40:1):

asterisks=BR55-2 mouse IgG3;
crosses=BR55-2 mouse/human chimeric IgG1;
squares=BR55-2 humanized IgG1/2;
losanges=BR55-2 humanized IgG1/3.

Figure 41:
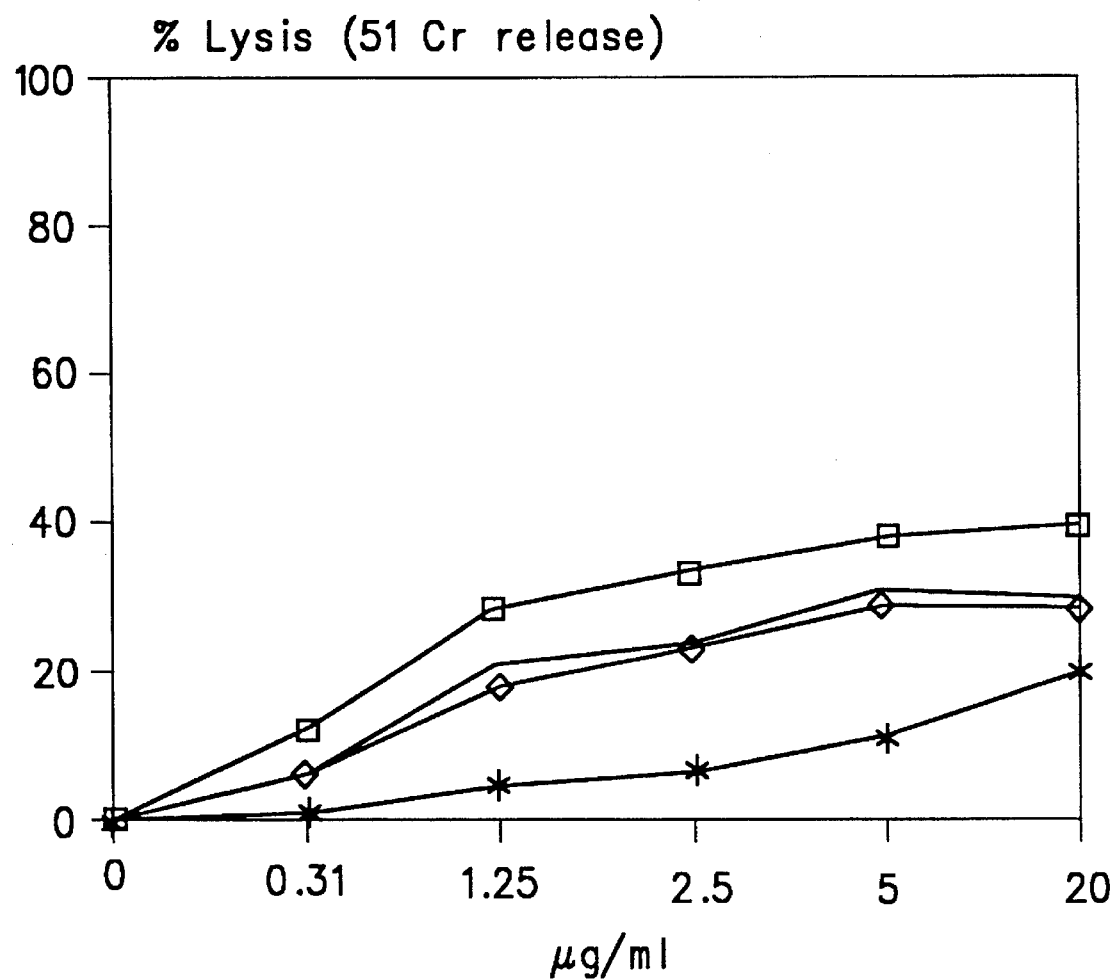
Figure 42A:
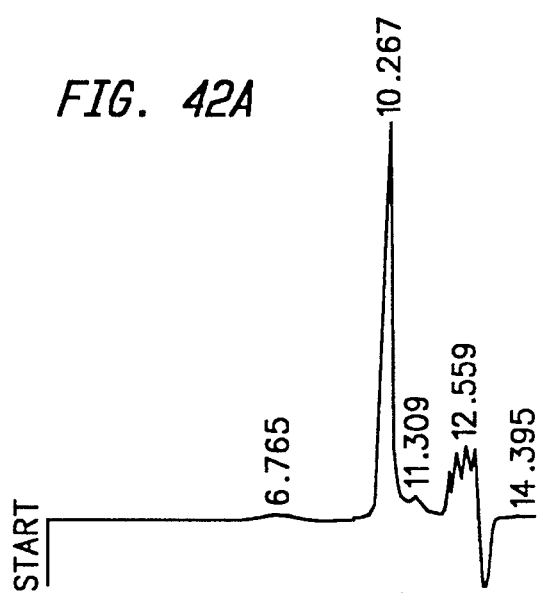
Figure 42B:
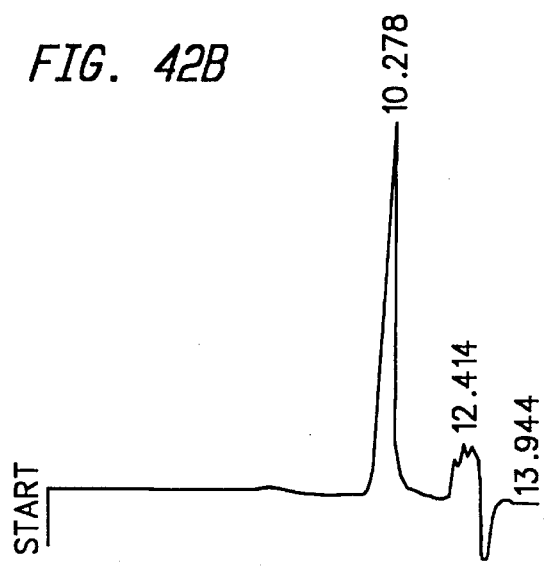
Figure 42C:
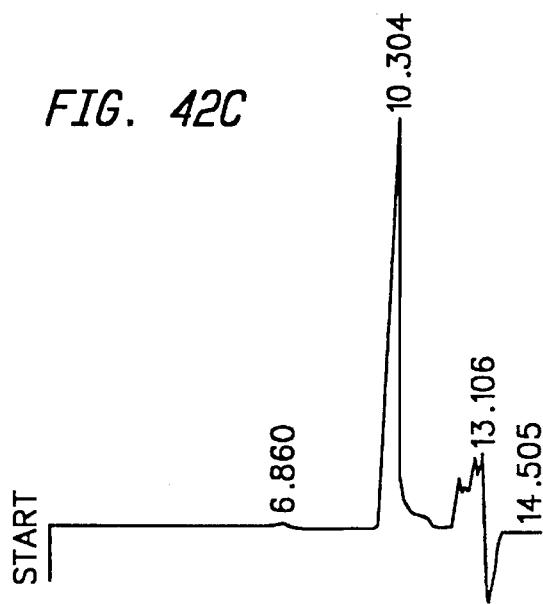
Figure 42D:
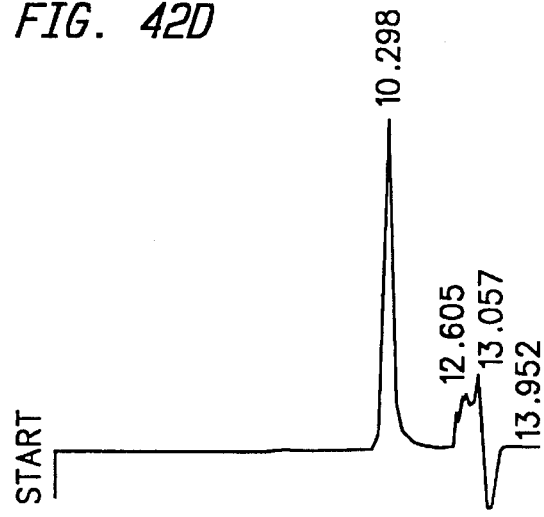

FIG. 41: Human granulocyte ADCC to SKBR5 breast cancer cell line: antibody dependent cellular cytotoxicity with human granulocytes (E:T=40:1):

asterisks=BR55-2 mouse IgG3;
crosses=BR55-2 mouse/human chimeric IgG1;
squares=BR55-2 humanized IgG1/2;
losanges=BR55-2 humanized IgG1/3;

FIG. 42: Size-exclusion HPLC:
42A=BR55-2 mouse IgG3;
42B=BR55-2 mouse/human chimeric IgG1;
42C=BR55-2 humanized IgG1/2;
42D=BR55-2 humanized IgG1/3.

STARTING MATERIALS

Murine monoclonal antibodies BR55-2 are available from e.g. hybridomas BR55.2 (BR55-2/IgG3) and, respectively, BR55.2S2a (BR-55-2/IgG2a).

These hybridomas were originally deposited on Feb. 17, 1987 and, respectively, Mar. 10, 1987 with the American Type Culture Collection, Rockville, Md. 20852, USA, under the provisions of the Budapest Treaty, under deposit numbers ATCC HB 9324 and, respectively, ATCC HB 9347.

SEQUENCE LISTING ( 1 ) GENERAL INFORMATION:

( i i i ) NUMBER OF SEQUENCES: 32

( 2 ) INFORMATION FOR SEQ ID NO:1:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Synthetic ( i x ) FEATURE:
        ( A ) NAME/KEY: misc_feature
        ( B ) LOCATION: 1..30
        ( D ) OTHER INFORMATION: /standard_name="Primer mc45"

( x i ) SEQUENCE DESCRIPTION: SEQ ID NO:1:

TATATCTAGA ATTCCCCCCC CCCCCCCCCC    30

( 2 ) INFORMATION FOR SEQ ID NO:2:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Synthetic ( i x ) FEATURE:
        ( A ) NAME/KEY: misc_feature
        ( B ) LOCATION: 1..46
        ( D ) OTHER INFORMATION: /standard_name="Primer mc46"

( x i ) SEQUENCE DESCRIPTION: SEQ ID NO:2:

TATAGAGCTC AAGCTTGGAT GGTGGGAAGA TGGATACAGT TGGTGC    46

(2) INFORMATION FOR SEQ ID NO:3:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (A) ORGANISM: Synthetic (ix) FEATURE:
        (A) NAME/KEY: misc_feature
        (B) LOCATION: 1..50
        (D) OTHER INFORMATION: /standard_name="Primer mc47"

(xi) SEQUENCE DESCRIPTION: SEQ ID NO:3:

```
TATAGAGCTC AAGCTTCCAG TGGATAGACH GATGGGGSTG TYGTTTTGGC          50
```

(2) INFORMATION FOR SEQ ID NO:4:

(i) SEQUENCE CHARACTERISTICS:
        (A) LENGTH: 434 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (A) ORGANISM: ATCC HB 9324

(ix) FEATURE:
        (A) NAME/KEY: CDS
        (B) LOCATION: 42..434

(ix) FEATURE:
        (A) NAME/KEY: misc_feature
        (B) LOCATION: 1..434
        (D) OTHER INFORMATION: /standard_name="Light Chain
            Variable Domain of BR55-2 Murine IgG3"

(ix) FEATURE:
        (A) NAME/KEY: misc_feature
        (B) LOCATION: 168..215
        (D) OTHER INFORMATION: /standard_name=
            " Complementarity-determining Region"

(ix) FEATURE:
        (A) NAME/KEY: misc_feature
        (B) LOCATION: 261..281
        (D) OTHER INFORMATION: /standard_name=
            " Complementarity-determining Region"

(ix) FEATURE:
        (A) NAME/KEY: misc_feature
        (B) LOCATION: 378..404
        (D) OTHER INFORMATION: /standard_name=
            " Complementarity-determining Region"

(xi) SEQUENCE DESCRIPTION: SEQ ID NO:4:

```
ATCAGTCTCC TCAGGCTGTC TCCTCAGGTT GCCTCCTCAA A ATG AAG TTG CCT         53
                                             Met Lys Leu Pro
                                              1

GTT AGG CTG TTG GTG CTG ATG TTC TGG ATT CCT GCT TCC AGC AGT GAT       101
Val Arg Leu Leu Val Leu Met Phe Trp Ile Pro Ala Ser Ser Ser Asp
 5               10                  15                      20

GTT TTG ATG ACC CAA ACT CCA CTC TCC CTG CCT GTC AGT CTT GGA GAT       149
Val Leu Met Thr Gln Thr Pro Leu Ser Leu Pro Val Ser Leu Gly Asp
```

|  |  |  |  |  |  |  | 25 |  |  |  |  | 30 |  |  |  |  | 35 |  |  |
|---|---|---|---|---|---|---|---|---|---|---|---|---|---|---|---|---|---|---|---|

```
CAA  GCC  TCC  ATC  TCT  TGC  AGA  TCT  AGT  CAG  AGC  ATT  GTA  CAT  AGT  AAT      197
Gln  Ala  Ser  Ile  Ser  Cys  Arg  Ser  Ser  Gln  Ser  Ile  Val  His  Ser  Asn
               40                      45                      50

GGA  AAC  ACC  TAT  TTA  GAA  TGG  TAC  CTG  CAG  AAA  CCA  GGC  CAG  TCT  CCA      245
Gly  Asn  Thr  Tyr  Leu  Glu  Trp  Tyr  Leu  Gln  Lys  Pro  Gly  Gln  Ser  Pro
          55                       60                       65

AAG  CTC  CTG  ATC  TCC  AAA  GTT  TCC  AAC  CGA  TTT  TCT  GGG  GTC  CCA  GAC      293
Lys  Leu  Leu  Ile  Ser  Lys  Val  Ser  Asn  Arg  Phe  Ser  Gly  Val  Pro  Asp
     70                       75                       80

AGG  TTC  AGT  GGC  AGT  GGA  TCA  GGG  ACA  GAT  TTC  ACA  CTC  AAG  ATC  AGC      341
Arg  Phe  Ser  Gly  Ser  Gly  Ser  Gly  Thr  Asp  Phe  Thr  Leu  Lys  Ile  Ser
85                       90                       95                      100

AGA  GTG  GAG  GCT  GAG  GAT  CTG  GGA  GTT  TAT  TAC  TGC  TTT  CAA  GGT  TCA      389
Arg  Val  Glu  Ala  Glu  Asp  Leu  Gly  Val  Tyr  Tyr  Cys  Phe  Gln  Gly  Ser
                    105                      110                     115

CAT  GTT  CCA  TTC  ACG  TTC  GGC  TCG  GGG  ACA  AAG  TTG  GAA  ATA  AAA           434
His  Val  Pro  Phe  Thr  Phe  Gly  Ser  Gly  Thr  Lys  Leu  Glu  Ile  Lys
               120                      125                     130
```

(2) INFORMATION FOR SEQ ID NO:5:

(i) SEQUENCE CHARACTERISTICS:
        (A) LENGTH: 131 amino acids
        (B) TYPE: amino acid
        (D) TOPOLOGY: linear (ii) MOLECULE TYPE: protein (xi) SEQUENCE DESCRIPTION: SEQ ID NO:5:

```
Met  Lys  Leu  Pro  Val  Arg  Leu  Leu  Val  Leu  Met  Phe  Trp  Ile  Pro  Ala
 1                    5                      10                      15

Ser  Ser  Ser  Asp  Val  Leu  Met  Thr  Gln  Thr  Pro  Leu  Ser  Leu  Pro  Val
               20                      25                      30

Ser  Leu  Gly  Asp  Gln  Ala  Ser  Ile  Ser  Cys  Arg  Ser  Ser  Gln  Ser  Ile
          35                       40                       45

Val  His  Ser  Asn  Gly  Asn  Thr  Tyr  Leu  Glu  Trp  Tyr  Leu  Gln  Lys  Pro
     50                       55                       60

Gly  Gln  Ser  Pro  Lys  Leu  Leu  Ile  Ser  Lys  Val  Ser  Asn  Arg  Phe  Ser
65                       70                       75                      80

Gly  Val  Pro  Asp  Arg  Phe  Ser  Gly  Ser  Gly  Ser  Gly  Thr  Asp  Phe  Thr
                    85                       90                       95

Leu  Lys  Ile  Ser  Arg  Val  Glu  Ala  Glu  Asp  Leu  Gly  Val  Tyr  Tyr  Cys
               100                     105                     110

Phe  Gln  Gly  Ser  His  Val  Pro  Phe  Thr  Phe  Gly  Ser  Gly  Thr  Lys  Leu
          115                     120                     125

Glu  Ile  Lys
     130
```

(2) INFORMATION FOR SEQ ID NO:6:

(i) SEQUENCE CHARACTERISTICS:
        (A) LENGTH: 491 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (A) ORGANISM: ATCC HB 9324

( i x ) FEATURE:
    ( A ) NAME/KEY: misc_feature
    ( B ) LOCATION: 1..491
    ( D ) OTHER INFORMATION: /standard_name="Heavy Chain
        Variable Domain of BR55-2 Murine IgG3"

( i x ) FEATURE:
    ( A ) NAME/KEY: CDS
    ( B ) LOCATION: 78..491

( i x ) FEATURE:
    ( A ) NAME/KEY: misc_feature
    ( B ) LOCATION: 225..239
    ( D ) OTHER INFORMATION: /standard_name=
        " Complementarity-determining Region CDR1"

( i x ) FEATURE:
    ( A ) NAME/KEY: misc_feature
    ( B ) LOCATION: 282..332
    ( D ) OTHER INFORMATION: /standard_name=
        " Complementarity-determining Region CDR2"

( i x ) FEATURE:
    ( A ) NAME/KEY: misc_feature
    ( B ) LOCATION: 429..458
    ( D ) OTHER INFORMATION: /standard_name=
        " Complementarity-determining Region CDR3"

( x i ) SEQUENCE DESCRIPTION: SEQ ID NO:6:

```
TTGACAGAGG AGGCCAGTCT GGATTCGATT CCCAGTTCCT CACATTCAGT GATCAGCACT         60

GAACACGGAC CCTCACC ATG AAC TTG GGG CTC AGC TTG ATT TTC CTT GTC           110
                   Met Asn Leu Gly Leu Ser Leu Ile Phe Leu Val
                    1               5                      10

CTT GTT TTA AAA GGT GTC CAG TGT GAA GTG AAG CTG GTG GAG TCT GGG          158
Leu Val Leu Lys Gly Val Gln Cys Glu Val Lys Leu Val Glu Ser Gly
             15              20                  25

GGA GGC TTA GTG CAG CCT GGA GGG TCC CTG AAA CTC TCC TGT GCA ACC          206
Gly Gly Leu Val Gln Pro Gly Gly Ser Leu Lys Leu Ser Cys Ala Thr
         30              35                  40

TCT GGA TTC ACT TTC AGT GAC TAT TAC ATG TAT TGG GTT CGC CAG ACT          254
Ser Gly Phe Thr Phe Ser Asp Tyr Tyr Met Tyr Trp Val Arg Gln Thr
     45              50                  55

CCA GAG AAG AGG CTG GAG TGG GTC GCA TAC ATT AGT AAT GGT GGT GGT          302
Pro Glu Lys Arg Leu Glu Trp Val Ala Tyr Ile Ser Asn Gly Gly Gly
 60              65                  70                      75

AGT AGC CAT TAT GTA GAC AGT GTA AAG GGC CGA TTC ACC ATC TCC AGA          350
Ser Ser His Tyr Val Asp Ser Val Lys Gly Arg Phe Thr Ile Ser Arg
             80              85                  90

GAC AAT GCC AAG AAC ACC CTG TAC CTG CAA ATG AGC CGT CTG AGG TCT          398
Asp Asn Ala Lys Asn Thr Leu Tyr Leu Gln Met Ser Arg Leu Arg Ser
         95              100                 105

GAG GAC ACA GCC ATG TAT CAC TGC GCA AGG GGG ATG GAT TAC GGG GCC          446
Glu Asp Thr Ala Met Tyr His Cys Ala Arg Gly Met Asp Tyr Gly Ala
     110             115                 120

TGG TTT GCT TAC TGG GGC CAG GGG ACT CTG GTC ACT GTC TCT GCA              491
Trp Phe Ala Tyr Trp Gly Gln Gly Thr Leu Val Thr Val Ser Ala
 125             130                 135
```

( 2 ) INFORMATION FOR SEQ ID NO:7:

( i ) SEQUENCE CHARACTERISTICS:
        ( A ) LENGTH: 138 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

```
Met  Asn  Leu  Gly  Leu  Ser  Leu  Ile  Phe  Leu  Val  Leu  Val  Leu  Lys  Gly
 1              5                        10                       15

Val  Gln  Cys  Glu  Val  Lys  Leu  Val  Glu  Ser  Gly  Gly  Gly  Leu  Val  Gln
              20                       25                       30

Pro  Gly  Gly  Ser  Leu  Lys  Leu  Ser  Cys  Ala  Thr  Ser  Gly  Phe  Thr  Phe
              35                       40                  45

Ser  Asp  Tyr  Tyr  Met  Tyr  Trp  Val  Arg  Gln  Thr  Pro  Glu  Lys  Arg  Leu
     50                       55                       60

Glu  Trp  Val  Ala  Tyr  Ile  Ser  Asn  Gly  Gly  Gly  Ser  Ser  His  Tyr  Val
 65                      70                  75                            80

Asp  Ser  Val  Lys  Gly  Arg  Phe  Thr  Ile  Ser  Arg  Asp  Asn  Ala  Lys  Asn
              85                       90                            95

Thr  Leu  Tyr  Leu  Gln  Met  Ser  Arg  Leu  Arg  Ser  Glu  Asp  Thr  Ala  Met
              100                      105                      110

Tyr  His  Cys  Ala  Arg  Gly  Met  Asp  Tyr  Gly  Ala  Trp  Phe  Ala  Tyr  Trp
          115                      120                      125

Gly  Gln  Gly  Thr  Leu  Val  Thr  Val  Ser  Ala
          130                 135
```

(2) INFORMATION FOR SEQ ID NO:8:

(i) SEQUENCE CHARACTERISTICS:
    (A) LENGTH: 427 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (ix) FEATURE:
    (A) NAME/KEY: misc_feature
    (B) LOCATION: 1..427
    (D) OTHER INFORMATION: /standard_name="Light Chain
         Variable Region of BR55-2 Antibody in pVk"

(ix) FEATURE:
    (A) NAME/KEY: CDS
    (B) LOCATION: 12..404

(ix) FEATURE:
    (A) NAME/KEY: misc_feature
    (B) LOCATION: 1..6
    (D) OTHER INFORMATION: /standard_name="Xba I restriction
         site"

(ix) FEATURE:
    (A) NAME/KEY: misc_feature
    (B) LOCATION: 422..427
    (D) OTHER INFORMATION: /standard_name="Xba I restriction
         site"

(xi) SEQUENCE DESCRIPTION: SEQ ID NO:8:

```
TCTAGACCAC C ATG AAG TTG CCT GTT AGG CTG TTG GTG CTG ATG TTC TGG        50
             Met Lys Leu Pro Val Arg Leu Leu Val Leu Met Phe Trp
              1               5                      10

ATT CCT GCT TCC AGC AGT GAT GTT TTG ATG ACC CAA ACT CCA CTC TCC          98
Ile Pro Ala Ser Ser Ser Asp Val Leu Met Thr Gln Thr Pro Leu Ser
     15              20                  25

CTG CCT GTC AGT CTT GGA GAT CAA GCC TCC ATC TCT TGC AGA TCT AGT         146
Leu Pro Val Ser Leu Gly Asp Gln Ala Ser Ile Ser Cys Arg Ser Ser
 30                  35                  40                  45

CAG AGC ATT GTA CAT AGT AAT GGA AAC ACC TAT TTA GAA TGG TAC CTG         194
Gln Ser Ile Val His Ser Asn Gly Asn Thr Tyr Leu Glu Trp Tyr Leu
             50                  55                  60
```

```
CAG  AAA  CCA  GGC  CAG  TCT  CCA  AAG  CTC  CTG  ATC  TCC  AAA  GTT  TCC  AAC              242
Gln  Lys  Pro  Gly  Gln  Ser  Pro  Lys  Leu  Leu  Ile  Ser  Lys  Val  Ser  Asn
               65                      70                      75

CGA  TTT  TCT  GGG  GTC  CCA  GAC  AGG  TTC  AGT  GGC  AGT  GGA  TCA  GGG  ACA              290
Arg  Phe  Ser  Gly  Val  Pro  Asp  Arg  Phe  Ser  Gly  Ser  Gly  Ser  Gly  Thr
               80                      85                      90

GAT  TTC  ACA  CTC  AAG  ATC  AGC  AGA  GTG  GAG  GCT  GAG  GAT  CTG  GGA  GTT              338
Asp  Phe  Thr  Leu  Lys  Ile  Ser  Arg  Val  Glu  Ala  Glu  Asp  Leu  Gly  Val
         95                     100                     105

TAT  TAC  TGC  TTT  CAA  GGT  TCA  CAT  GTT  CCA  TTC  ACG  TTC  GGC  TCG  GGG              386
Tyr  Tyr  Cys  Phe  Gln  Gly  Ser  His  Val  Pro  Phe  Thr  Phe  Gly  Ser  Gly
110                      115                     120                     125

ACA  AAG  TTG  GAA  ATA  AAA  CGTAAGTAGA  CTTTTGCTCT  AGA                                   427
Thr  Lys  Leu  Glu  Ile  Lys
                    130
```

( 2 ) INFORMATION FOR SEQ ID NO:9:

( i ) SEQUENCE CHARACTERISTICS:
        ( A ) LENGTH: 131 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

```
Met  Lys  Leu  Pro  Val  Arg  Leu  Leu  Val  Leu  Met  Phe  Trp  Ile  Pro  Ala
 1                   5                    10                      15

Ser  Ser  Ser  Asp  Val  Leu  Met  Thr  Gln  Thr  Pro  Leu  Ser  Leu  Pro  Val
               20                       25                      30

Ser  Leu  Gly  Asp  Gln  Ala  Ser  Ile  Ser  Cys  Arg  Ser  Ser  Gln  Ser  Ile
          35                        40                      45

Val  His  Ser  Asn  Gly  Asn  Thr  Tyr  Leu  Glu  Trp  Tyr  Leu  Gln  Lys  Pro
     50                       55                      60

Gly  Gln  Ser  Pro  Lys  Leu  Leu  Ile  Ser  Lys  Val  Ser  Asn  Arg  Phe  Ser
65                        70                      75                       80

Gly  Val  Pro  Asp  Arg  Phe  Ser  Gly  Ser  Gly  Ser  Gly  Thr  Asp  Phe  Thr
                    85                       90                       95

Leu  Lys  Ile  Ser  Arg  Val  Glu  Ala  Glu  Asp  Leu  Gly  Val  Tyr  Tyr  Cys
               100                      105                     110

Phe  Gln  Gly  Ser  His  Val  Pro  Phe  Thr  Phe  Gly  Ser  Gly  Thr  Lys  Leu
          115                     120                     125

Glu  Ile  Lys
          130
```

( 2 ) INFORMATION FOR SEQ ID NO:10:

( i ) SEQUENCE CHARACTERISTICS:
        ( A ) LENGTH: 445 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i x ) FEATURE:
        ( A ) NAME/KEY: misc_feature
        ( B ) LOCATION: 1..445
        ( D ) OTHER INFORMATION: /standard_name="Heavy Chain
            V-region of BR55-2 Antibody in pVg-1c and pVg-3c"

( i x ) FEATURE:

( A ) NAME/KEY: CDS
( B ) LOCATION: 12..425

( i x ) FEATURE:
( A ) NAME/KEY: misc_feature
( B ) LOCATION: 1..6
( D ) OTHER INFORMATION: /standard_name="Xba I restriction site"

( i x ) FEATURE:
( A ) NAME/KEY: misc_feature
( B ) LOCATION: 440..445
( D ) OTHER INFORMATION: /standard_name="Xba I restriction site"

( x i ) SEQUENCE DESCRIPTION: SEQ ID NO:10:

```
TCTAGACCAC C ATG AAC TTG GGG CTC AGC TTG ATT TTC CTT GTC CTT GTT           50
             Met Asn Leu Gly Leu Ser Leu Ile Phe Leu Val Leu Val
              1               5                      10

TTA AAA GGT GTC CAG TGT GAA GTG AAG CTG GTG GAG TCT GGG GGA GGC             98
Leu Lys Gly Val Gln Cys Glu Val Lys Leu Val Glu Ser Gly Gly Gly
         15                  20                  25

TTA GTG CAG CCT GGA GGG TCC CTG AAA CTC TCC TGT GCA ACC TCT GGA            146
Leu Val Gln Pro Gly Gly Ser Leu Lys Leu Ser Cys Ala Thr Ser Gly
 30                  35                  40                  45

TTC ACT TTC AGT GAC TAT TAC ATG TAT TGG GTT CGC CAG ACT CCA GAG            194
Phe Thr Phe Ser Asp Tyr Tyr Met Tyr Trp Val Arg Gln Thr Pro Glu
                 50                  55                  60

AAG AGG CTG GAG TGG GTC GCA TAC ATT AGT AAT GGT GGT GGT AGT AGC            242
Lys Arg Leu Glu Trp Val Ala Tyr Ile Ser Asn Gly Gly Gly Ser Ser
             65                  70                  75

CAT TAT GTA GAC AGT GTA AAG GGC CGA TTC ACC ATC TCC AGA GAC AAT            290
His Tyr Val Asp Ser Val Lys Gly Arg Phe Thr Ile Ser Arg Asp Asn
             80                  85                  90

GCC AAG AAC ACC CTG TAC CTG CAA ATG AGC CGT CTG AGG TCT GAG GAC            338
Ala Lys Asn Thr Leu Tyr Leu Gln Met Ser Arg Leu Arg Ser Glu Asp
 95                 100                 105

ACA GCC ATG TAT CAC TGC GCA AGG GGG ATG GAT TAC GGG GCC TGG TTT            386
Thr Ala Met Tyr His Cys Ala Arg Gly Met Asp Tyr Gly Ala Trp Phe
110                 115                 120                 125

GCT TAC TGG GGC CAG GGG ACT CTG GTC ACT GTC TCT GCA GGTGAGTCCT             435
Ala Tyr Trp Gly Gln Gly Thr Leu Val Thr Val Ser Ala
                 130                 135

AACTTCTAGA                                                                 445
```

( 2 ) INFORMATION FOR SEQ ID NO:11:

( i ) SEQUENCE CHARACTERISTICS:
( A ) LENGTH: 138 amino acids
( B ) TYPE: amino acid
( D ) TOPOLOGY: linear ( i i ) MOLECULE TYPE: protein ( x i ) SEQUENCE DESCRIPTION: SEQ ID NO:11:

```
Met Asn Leu Gly Leu Ser Leu Ile Phe Leu Val Leu Val Leu Lys Gly
 1               5                  10                  15

Val Gln Cys Glu Val Lys Leu Val Glu Ser Gly Gly Gly Leu Val Gln
             20                  25                  30

Pro Gly Gly Ser Leu Lys Leu Ser Cys Ala Thr Ser Gly Phe Thr Phe
             35                  40                  45

Ser Asp Tyr Tyr Met Tyr Trp Val Arg Gln Thr Pro Glu Lys Arg Leu
         50                  55                  60

Glu Trp Val Ala Tyr Ile Ser Asn Gly Gly Gly Ser Ser His Tyr Val
```

|       |       |       |       |       |       |       |       |       |       |       |       |       |       |       |       |
|---|---|---|---|---|---|---|---|---|---|---|---|---|---|---|---|
| 65 | | | | | 70 | | | | | 75 | | | | | 80 |

Asp Ser Val Lys Gly Arg Phe Thr Ile Ser Arg Asp Asn Ala Lys Asn
                85                          90                          95

Thr Leu Tyr Leu Gln Met Ser Arg Leu Arg Ser Glu Asp Thr Ala Met
                100                         105                         110

Tyr His Cys Ala Arg Gly Met Asp Tyr Gly Ala Trp Phe Ala Tyr Trp
            115                         120                     125

Gly Gln Gly Thr Leu Val Thr Val Ser Ala
        130                 135

( 2 ) INFORMATION FOR SEQ ID NO:12:

( i ) SEQUENCE CHARACTERISTICS:
        ( A ) LENGTH: 119 amino acids
        ( B ) TYPE: amino acid
        ( D ) TOPOLOGY: linear ( i i ) MOLECULE TYPE: peptide ( i i i ) HYPOTHETICAL: NO ( i x ) FEATURE:
        ( A ) NAME/KEY: Peptide
        ( B ) LOCATION: 1..119
        ( D ) OTHER INFORMATION: /note="Sequence of Humanized
            BR55-2 Antibody, Heavy Chain Variant
            H-hu-BR55- 2/1"

( i x ) FEATURE:
        ( A ) NAME/KEY: Region
        ( B ) LOCATION: 31..35
        ( D ) OTHER INFORMATION: /note="Complementarity-determining
            region"

( i x ) FEATURE:
        ( A ) NAME/KEY: Region
        ( B ) LOCATION: 50..66
        ( D ) OTHER INFORMATION: /note="Complementarity-determining
            region"

( i x ) FEATURE:
        ( A ) NAME/KEY: Region
        ( B ) LOCATION: 99..108
        ( D ) OTHER INFORMATION: /note="Complementarity-determining
            region"

( x i ) SEQUENCE DESCRIPTION: SEQ ID NO:12:

Glu Val Gln Leu Leu Glu Ser Gly Gly Gly Leu Val Gln Pro Gly Gly
1               5                       10                      15

Ser Leu Arg Leu Ser Cys Ala Ala Ser Gly Phe Thr Phe Ser Asp Tyr
                20                      25                      30

Tyr Met Tyr Trp Val Arg Gln Ala Pro Gly Lys Gly Leu Glu Trp Val
            35                      40                      45

Ala Tyr Ile Ser Asn Gly Gly Gly Ser Ser His Tyr Val Asp Ser Val
        50                      55                      60

Lys Gly Arg Phe Thr Ile Ser Arg Asp Asn Ser Lys Asn Thr Leu Tyr
65                      70                      75                      80

Leu Gln Met Asn Ser Leu Arg Ala Glu Asp Thr Ala Leu Tyr Tyr Cys
                85                      90                      95

Ala Arg Gly Met Asp Tyr Gly Ala Trp Phe Ala Tyr Trp Gly Gln Gly
            100                     105                     110

Thr Leu Val Thr Val Ser Ser
        115

( 2 ) INFORMATION FOR SEQ ID NO:13:

( i ) SEQUENCE CHARACTERISTICS:
 ( A ) LENGTH: 119 amino acids
 ( B ) TYPE: amino acid
 ( D ) TOPOLOGY: linear ( i i ) MOLECULE TYPE: peptide ( i i i ) HYPOTHETICAL: NO ( i x ) FEATURE:
 ( A ) NAME/KEY: Peptide
 ( B ) LOCATION: 1..119
 ( D ) OTHER INFORMATION: /note="Sequence of Humanized
  BR55-2 Antibody, Heavy Chain Variant H-hu-BR5-2/2"

( i x ) FEATURE:
 ( A ) NAME/KEY: Region
 ( B ) LOCATION: 31..35
 ( D ) OTHER INFORMATION: /note="Complementarity-determining
  region"

( i x ) FEATURE:
 ( A ) NAME/KEY: Region
 ( B ) LOCATION: 50..66
 ( D ) OTHER INFORMATION: /note="Complementarity-determining
  region"

( i x ) FEATURE:
 ( A ) NAME/KEY: Region
 ( B ) LOCATION: 99..108
 ( D ) OTHER INFORMATION: /note="Complementarity-determining
  region"

( x i ) SEQUENCE DESCRIPTION: SEQ ID NO:13:

| Glu | Val | Gln | Leu | Leu | Glu | Ser | Gly | Gly | Gly | Leu | Val | Gln | Pro | Gly | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ser | Leu | Arg | Leu | Ser | Cys | Ala | Ala | Ser | Gly | Phe | Thr | Phe | Ser | Asp | Tyr |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Tyr | Met | Tyr | Trp | Val | Arg | Gln | Ala | Pro | Glu | Lys | Arg | Leu | Glu | Trp | Val |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Ala | Tyr | Ile | Ser | Asn | Gly | Gly | Gly | Ser | Ser | His | Tyr | Val | Asp | Ser | Val |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Lys | Gly | Arg | Phe | Thr | Ile | Ser | Arg | Asp | Asn | Ser | Lys | Asn | Thr | Leu | Tyr |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Leu | Gln | Met | Asn | Ser | Leu | Arg | Ala | Glu | Asp | Thr | Ala | Leu | Tyr | His | Cys |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Ala | Arg | Gly | Met | Asp | Tyr | Gly | Ala | Trp | Phe | Ala | Tyr | Trp | Gly | Gln | Gly |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Thr | Leu | Val | Thr | Val | Ser | Ser |
|-----|-----|-----|-----|-----|-----|-----|
|     |     | 115 |     |     |     |     |

( 2 ) INFORMATION FOR SEQ ID NO:14:

( i ) SEQUENCE CHARACTERISTICS:
 ( A ) LENGTH: 119 amino acids
 ( B ) TYPE: amino acid
 ( D ) TOPOLOGY: linear ( i i ) MOLECULE TYPE: peptide ( i i i ) HYPOTHETICAL: NO ( i x ) FEATURE:
 ( A ) NAME/KEY: Peptide
 ( B ) LOCATION: 1..119
 ( D ) OTHER INFORMATION: /note="Sequence of Humanized
  BR55-2 Antibody, Heavy Chain Variant
  H-hu-BR55- 2/3"

( i x ) FEATURE:
 ( A ) NAME/KEY: Region ( B ) LOCATION: 31..35
            ( D ) OTHER INFORMATION: /note="Complementarity-determining
                    region"

( i x ) FEATURE:
            ( A ) NAME/KEY: Region
            ( B ) LOCATION: 50..66
            ( D ) OTHER INFORMATION: /note="Complementarity-determining
                    region"

( i x ) FEATURE:
            ( A ) NAME/KEY: Region
            ( B ) LOCATION: 99..108
            ( D ) OTHER INFORMATION: /note="Complementarity-determining
                    region"

( x i ) SEQUENCE DESCRIPTION: SEQ ID NO:14:

| Glu | Val | Gln | Leu | Leu | Glu | Ser | Gly | Gly | Gly | Leu | Val | Gln | Pro | Gly | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ser | Leu | Arg | Leu | Ser | Cys | Ala | Ala | Ser | Gly | Phe | Thr | Phe | Ser | Asp | Tyr |
|     |     |     | 20  |     |     |     |     | 25  |     |     |     |     | 30  |     |     |

| Tyr | Met | Tyr | Trp | Val | Arg | Gln | Ala | Pro | Glu | Lys | Arg | Leu | Glu | Trp | Val |
|     |     | 35  |     |     |     |     | 40  |     |     |     |     | 45  |     |     |     |

| Ala | Tyr | Ile | Ser | Asn | Gly | Gly | Gly | Ser | Ser | His | Tyr | Val | Asp | Ser | Val |
|     | 50  |     |     |     |     | 55  |     |     |     |     | 60  |     |     |     |     |

| Lys | Gly | Arg | Phe | Thr | Ile | Ser | Arg | Asp | Asn | Ala | Lys | Asn | Thr | Leu | Tyr |
| 65  |     |     |     |     | 70  |     |     |     |     | 75  |     |     |     |     | 80  |

| Leu | Gln | Met | Asn | Ser | Leu | Arg | Ala | Glu | Asp | Thr | Ala | Leu | Tyr | His | Cys |
|     |     |     |     | 85  |     |     |     |     | 90  |     |     |     |     | 95  |     |

| Ala | Arg | Gly | Met | Asp | Tyr | Gly | Ala | Trp | Phe | Ala | Tyr | Trp | Gly | Gln | Gly |
|     |     |     | 100 |     |     |     |     | 105 |     |     |     |     | 110 |     |     |

| Thr | Leu | Val | Thr | Val | Ser | Ser |
|     |     | 115 |     |     |     |     |

( 2 ) INFORMATION FOR SEQ ID NO:15:

( i ) SEQUENCE CHARACTERISTICS:
            ( A ) LENGTH: 112 amino acids
            ( B ) TYPE: amino acid
            ( D ) TOPOLOGY: linear ( i i ) MOLECULE TYPE: peptide ( i i i ) HYPOTHETICAL: NO ( i x ) FEATURE:
            ( A ) NAME/KEY: Peptide
            ( B ) LOCATION: 1..112
            ( D ) OTHER INFORMATION: /note="Sequence of the Light Chain
                    of Humanized BR55-2 Antibody"

( i x ) FEATURE:
            ( A ) NAME/KEY: Region
            ( B ) LOCATION: 24..39
            ( D ) OTHER INFORMATION: /note="Complementarity-determining
                    region"

( i x ) FEATURE:
            ( A ) NAME/KEY: Region
            ( B ) LOCATION: 55..61
            ( D ) OTHER INFORMATION: /note="Complementarity-determining
                    region"

( i x ) FEATURE:
            ( A ) NAME/KEY: Region
            ( B ) LOCATION: 94..102
            ( D ) OTHER INFORMATION: /note="Complementarity-determining
                    region"

( i x ) FEATURE:
            ( A ) NAME/KEY: Modified-site (B) LOCATION: 54
(D) OTHER INFORMATION: /note="Residue that has been
replaced with mouse amino acid in the humanized
antibody."

(ix) FEATURE:
(A) NAME/KEY: Modified-site
(B) LOCATION: 108
(D) OTHER INFORMATION: /note="Residue in the framework
that is replaced with mouse amino acid in the
humanized antibody."

(xi) SEQUENCE DESCRIPTION: SEQ ID NO:15:

| Asp | Ile | Val | Met | Thr | Gln | Ser | Pro | Leu | Ser | Leu | Pro | Val | Thr | Pro | Gly |
|---|---|---|---|---|---|---|---|---|---|---|---|---|---|---|---|
| 1 | | | | 5 | | | | | 10 | | | | | 15 | |
| Glu | Pro | Ala | Ser | Ile | Ser | Cys | Arg | Ser | Ser | Gln | Ser | Ile | Val | His | Ser |
| | | | 20 | | | | | 25 | | | | | 30 | | |
| Asn | Gly | Asn | Thr | Tyr | Leu | Glu | Trp | Tyr | Leu | Gln | Lys | Pro | Gly | Gln | Ser |
| | | 35 | | | | | 40 | | | | | 45 | | | |
| Pro | Gln | Leu | Leu | Ile | Ser | Lys | Val | Ser | Asn | Arg | Phe | Ser | Gly | Val | Pro |
| | 50 | | | | | 55 | | | | | 60 | | | | |
| Asp | Arg | Phe | Ser | Gly | Ser | Gly | Ser | Gly | Thr | Asp | Phe | Thr | Leu | Lys | Ile |
| 65 | | | | | 70 | | | | | 75 | | | | | 80 |
| Ser | Arg | Val | Glu | Ala | Glu | Asp | Val | Gly | Val | Tyr | Tyr | Cys | Phe | Gln | Gly |
| | | | | 85 | | | | | 90 | | | | | 95 | |
| Ser | His | Val | Pro | Phe | Thr | Phe | Gly | Gln | Gly | Thr | Lys | Leu | Glu | Ile | Lys |
| | | | 100 | | | | | 105 | | | | | 110 | | |

(2) INFORMATION FOR SEQ ID NO:16:

(i) SEQUENCE CHARACTERISTICS:
(A) LENGTH: 112 amino acids
(B) TYPE: amino acid
(D) TOPOLOGY: linear (ii) MOLECULE TYPE: peptide (iii) HYPOTHETICAL: NO (ix) FEATURE:
(A) NAME/KEY: Peptide
(B) LOCATION: 1..112
(D) OTHER INFORMATION: /note="Sequence of Tew antibody
fragment"

(ix) FEATURE:
(A) NAME/KEY: Peptide
(B) LOCATION: 1..112
(D) OTHER INFORMATION: /note="E.A. Kabat, et al.,
Sequences of Protein of Immunological Interest,
4th Ed. (1987), US Dept. of Health and Human Services (xi) SEQUENCE DESCRIPTION: SEQ ID NO:16:

| Asp | Ile | Val | Met | Thr | Gln | Ser | Pro | Leu | Ser | Leu | Pro | Val | Thr | Pro | Gly |
|---|---|---|---|---|---|---|---|---|---|---|---|---|---|---|---|
| 1 | | | | 5 | | | | | 10 | | | | | 15 | |
| Glu | Pro | Ala | Ser | Ile | Ser | Cys | Arg | Ser | Ser | Gln | Ser | Leu | Leu | His | Ser |
| | | | 20 | | | | | 25 | | | | | 30 | | |
| Asp | Gly | Phe | Asp | Tyr | Leu | Asn | Trp | Tyr | Leu | Gln | Lys | Pro | Gly | Gln | Ser |
| | | 35 | | | | | 40 | | | | | 45 | | | |
| Pro | Gln | Leu | Leu | Ile | Tyr | Ala | Leu | Ser | Asn | Arg | Ala | Ser | Gly | Val | Pro |
| | 50 | | | | | 55 | | | | | 60 | | | | |
| Asp | Arg | Phe | Ser | Gly | Ser | Gly | Ser | Gly | Thr | Asp | Phe | Thr | Leu | Lys | Ile |
| 65 | | | | | 70 | | | | | 75 | | | | | 80 |
| Ser | Arg | Val | Glu | Ala | Glu | Asp | Val | Gly | Val | Tyr | Tyr | Cys | Met | Gln | Ala |
| | | | | 85 | | | | | 90 | | | | | 95 | |

Leu Gln Ala Pro Ile Thr Phe Gly Gln Gly Thr Arg Leu Glu Ile Lys
                100                 105                 110

(2) INFORMATION FOR SEQ ID NO:17:

(i) SEQUENCE CHARACTERISTICS:
        (A) LENGTH: 119 amino acids
        (B) TYPE: amino acid
        (D) TOPOLOGY: linear (ii) MOLECULE TYPE: peptide (iii) HYPOTHETICAL: NO (ix) FEATURE:
        (A) NAME/KEY: Peptide
        (B) LOCATION: 1..119
        (D) OTHER INFORMATION: /note="Sequence of the heavy chain of humanized BR55-2/3 antibody."

(ix) FEATURE:
        (A) NAME/KEY: Region
        (B) LOCATION: 31..35
        (D) OTHER INFORMATION: /note="Complementarity-determining region"

(ix) FEATURE:
        (A) NAME/KEY: Region
        (B) LOCATION: 50..66
        (D) OTHER INFORMATION: /note="Complementarity-determining region"

(ix) FEATURE:
        (A) NAME/KEY: Region
        (B) LOCATION: 99..108
        (D) OTHER INFORMATION: /note="Complementarity-determining region"

(ix) FEATURE:
        (A) NAME/KEY: Modified-site
        (B) LOCATION: 42
        (D) OTHER INFORMATION: /note="Residue in the framework replaced with mouse amino acid in the humanized antibody."

(ix) FEATURE:
        (A) NAME/KEY: Modified-site
        (B) LOCATION: 44
        (D) OTHER INFORMATION: /note="Residue replaced with mouse amino acid in humanized antibody."

(ix) FEATURE:
        (A) NAME/KEY: Modified-site
        (B) LOCATION: 73..75
        (D) OTHER INFORMATION: /note="Residues replaced with mouse amino acids in humanized antibody."

(ix) FEATURE:
        (A) NAME/KEY: Modified-site
        (B) LOCATION: 82
        (D) OTHER INFORMATION: /note="Residue replaced with mouse amino acids in humanized antibody."

(ix) FEATURE:
        (A) NAME/KEY: Modified-site
        (B) LOCATION: 87
        (D) OTHER INFORMATION: /note="Residue replaced with mouse amino acid in humanized antibody."

(ix) FEATURE:
        (A) NAME/KEY: Modified-site
        (B) LOCATION: 109
        (D) OTHER INFORMATION: /note="Residue replaced with mouse amino acid in humanized antibody."

(xi) SEQUENCE DESCRIPTION: SEQ ID NO:17:

Glu Val Gln Leu Leu Glu Ser Gly Gly Gly Leu Val Gln Pro Gly Gly
 1               5                  10                  15

```
             Ser  Leu  Arg  Leu  Ser  Cys  Ala  Ala  Ser  Gly  Phe  Thr  Phe  Ser  Asp  Tyr
                            20                       25                      30

Tyr  Met  Tyr  Trp  Val  Arg  Gln  Ala  Pro  Glu  Lys  Arg  Leu  Glu  Trp  Val
                       35                       40                      45

Ala  Tyr  Ile  Ser  Asn  Gly  Gly  Gly  Ser  Ser  His  Tyr  Val  Asp  Ser  Val
                  50                      55                      60

Lys  Gly  Arg  Phe  Thr  Ile  Ser  Arg  Asp  Asn  Ala  Lys  Asn  Thr  Leu  Tyr
             65                      70                      75                           80

Leu  Gln  Met  Asn  Ser  Leu  Arg  Ala  Glu  Asp  Thr  Ala  Leu  Tyr  His  Cys
                            85                       90                      95

Ala  Arg  Gly  Met  Asp  Tyr  Gly  Ala  Trp  Phe  Ala  Tyr  Trp  Gly  Gln  Gly
                            100                      105                     110

Thr  Leu  Val  Thr  Val  Ser  Ser
                            115
```

( 2 ) INFORMATION FOR SEQ ID NO:18:

( i ) SEQUENCE CHARACTERISTICS:
        ( A ) LENGTH: 122 amino acids
        ( B ) TYPE: amino acid
        ( D ) TOPOLOGY: linear ( i i ) MOLECULE TYPE: peptide ( i i i ) HYPOTHETICAL: NO ( i x ) FEATURE:
        ( A ) NAME/KEY: Peptide
        ( B ) LOCATION: 1..122
        ( D ) OTHER INFORMATION: /note="Sequence of Pom antibody
            fragment"

( i x ) FEATURE:
        ( A ) NAME/KEY: Peptide
        ( B ) LOCATION: 1..122
        ( D ) OTHER INFORMATION: /note="E.A. Kabat et al.,
            Sequences of Proteins of Immunological Interest,
            4th Ed. (1987), US Dept. of Health and Human Services ( x i ) SEQUENCE DESCRIPTION: SEQ ID NO:18:

```
             Glu  Val  Gln  Leu  Leu  Glu  Ser  Gly  Gly  Gly  Leu  Val  Gln  Pro  Gly  Gly
             1                       5                       10                          15

Ser  Leu  Arg  Leu  Ser  Cys  Ala  Ala  Ser  Gly  Phe  Thr  Phe  Ser  Ser  Ser
                            20                      25                      30

Ala  Met  Ser  Trp  Val  Arg  Gln  Ala  Pro  Gly  Lys  Gly  Leu  Glu  Trp  Val
                       35                      40                      45

Ala  Trp  Lys  Tyr  Glu  Asn  Gly  Asn  Asp  Lys  His  Tyr  Ala  Asp  Ser  Val
                  50                      55                      60

Asn  Gly  Arg  Phe  Thr  Ile  Ser  Arg  Asn  Asp  Ser  Lys  Asn  Thr  Leu  Tyr
             65                      70                      75                           80

Leu  Leu  Met  Asn  Ser  Leu  Gln  Ala  Glu  Asp  Thr  Ala  Leu  Tyr  Tyr  Cys
                            85                      90                      95

Ala  Arg  Asp  Ala  Gly  Pro  Tyr  Val  Ser  Pro  Thr  Phe  Phe  Ala  His  Tyr
                            100                     105                     110

Gly  Gln  Gly  Thr  Leu  Val  Thr  Val  Ser  Ser
                            115                     120
```

( 2 ) INFORMATION FOR SEQ ID NO:19:

( i ) SEQUENCE CHARACTERISTICS:
        ( A ) LENGTH: 108 base pairs
        ( B ) TYPE: nucleic acid
        ( C ) STRANDEDNESS: single (D) TOPOLOGY: linear (i i) MOLECULE TYPE: DNA (genomic)

(i i i) HYPOTHETICAL: NO (v i) ORIGINAL SOURCE:
    (A) ORGANISM: Synthetic (i x) FEATURE:
    (A) NAME/KEY: misc_feature
    (B) LOCATION: 1..108
    (D) OTHER INFORMATION: /standard_name="Oligonucleotide jb37"

(x i) SEQUENCE DESCRIPTION: SEQ ID NO:19:

```
TATATCTAGA CCACCATGAA GTTGCCTGTT AGGCTGTTGG TGCTGATGTT CTGGATTCCT        60
GCTTCCAGCA GTGATATTGT GATGACCCAA TCTCCACTCT CCCTGCCT                    108
```

(2) INFORMATION FOR SEQ ID NO:20:

(i) SEQUENCE CHARACTERISTICS:
    (A) LENGTH: 108 base pairs
    (B) TYPE: nucleic acid
    (C) STRANDEDNESS: single
    (D) TOPOLOGY: linear (i i) MOLECULE TYPE: DNA (genomic)

(i i i) HYPOTHETICAL: NO (v i) ORIGINAL SOURCE:
    (A) ORGANISM: Synthetic (i x) FEATURE:
    (A) NAME/KEY: misc_feature
    (B) LOCATION: 1..108
    (D) OTHER INFORMATION: /standard_name="Oligonucleotide jb38"

(x i) SEQUENCE DESCRIPTION: SEQ ID NO:20:

```
TATAGGTACC ATTCTAAATA GGTGTTTCCA TTACTATGTA CAATGCTCTG ACTAGACCTG        60
CAAGAGATGG AGGCTGGCTC TCCAGGAGTG ACAGGCAGGG AGAGTGGA                    108
```

(2) INFORMATION FOR SEQ ID NO:21:

(i) SEQUENCE CHARACTERISTICS:
    (A) LENGTH: 133 base pairs
    (B) TYPE: nucleic acid
    (C) STRANDEDNESS: single
    (D) TOPOLOGY: linear (i i) MOLECULE TYPE: DNA (genomic)

(i i i) HYPOTHETICAL: NO (v i) ORIGINAL SOURCE:
    (A) ORGANISM: Synthetic (i x) FEATURE:
    (A) NAME/KEY: misc_feature
    (B) LOCATION: 1..133
    (D) OTHER INFORMATION: /standard_name="Oligonucleotide jb39"

(x i) SEQUENCE DESCRIPTION: SEQ ID NO:21:

```
TATAGGTACC TTCAGAAACC AGGCCAGTCT CCACAGCTCC TGATCTCCAA AGTTTCCAAC        60
CGATTTTCTG GGGTCCCAGA CAGGTTCAGT GGCAGTGGAT CAGGGACAGA TTTCACACTC       120
AAGATCAGCA GAG                                                          133
```

( 2 ) INFORMATION FOR SEQ ID NO:22:

( i ) SEQUENCE CHARACTERISTICS:
        ( A ) LENGTH: 132 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Synthetic ( i x ) FEATURE:
        ( A ) NAME/KEY: misc_feature
        ( B ) LOCATION: 1..132
        ( D ) OTHER INFORMATION: /standard_name="Oligonucleotide
            jb40"

( x i ) SEQUENCE DESCRIPTION: SEQ ID NO:22:

```
TATATCTAGA GCAAAAGTCT ACTTACGTTT TATTTCCAAC TTTGTCCCCT GGCCGAACGT    60

GAATGGAACA TGTGAACCTT GAAAGCAGTA ATAAACTCCC ACATCCTCAG CCTCCACTCT   120

GCTGATCTTG AG                                                       132
```

( 2 ) INFORMATION FOR SEQ ID NO:23:

( i ) SEQUENCE CHARACTERISTICS:
        ( A ) LENGTH: 132 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Synthetic ( i x ) FEATURE:
        ( A ) NAME/KEY: misc_feature
        ( B ) LOCATION: 1..132
        ( D ) OTHER INFORMATION: /standard_name="Oligonucleotide
            mc108"

( x i ) SEQUENCE DESCRIPTION: SEQ ID NO:23:

```
TATATCTAGA CCACCATGAA CTTCGGGCTA AGCTTGATTT TCCTTGTCCT TGTTTTAAAA    60

GGTGTCCAGT GTGAAGTGCA ACTGCTGGAG TCTGGGGGAG GCTTAGTGCA GCCTGGAGGA   120

AGTCTACGAC TC                                                       132
```

( 2 ) INFORMATION FOR SEQ ID NO:24:

( i ) SEQUENCE CHARACTERISTICS:
        ( A ) LENGTH: 133 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Synthetic ( i x ) FEATURE:
        ( A ) NAME/KEY: misc_feature
        ( B ) LOCATION: 1..133
        ( D ) OTHER INFORMATION: /standard_name="Oligonucleotide
            mc109"

( x i ) SEQUENCE DESCRIPTION: SEQ ID NO:24:

TATAGAGCTC CCACCACCGT TGCTAATGTA TGCGACCCAC TCCAGCCTCT TTTCTGGAGC 60

CTGGCGAACC CAGTACATGT AATAATCACT GAAAGTGAAT CCAGAGGCTG CACAGGAGAG 120

TCGTAGACTT CCT 133

( 2 ) INFORMATION FOR SEQ ID NO:25:

( i ) SEQUENCE CHARACTERISTICS:
        ( A ) LENGTH: 118 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Synthetic ( i x ) FEATURE:
        ( A ) NAME/KEY: misc_feature
        ( B ) LOCATION: 1..118
        ( D ) OTHER INFORMATION: /standard_name="Oligonucleotide
            mc110"

( x i ) SEQUENCE DESCRIPTION: SEQ ID NO:25:

TATAGAGCTC ACATTACGTA GATTCGGTCA AGGGCCGATT CACCATCTCC AGAGATAATG 60

CCAAGAACAC CCTGTACCTG CAGATGAACT CACTGCGAGC TGAGGACACG GCCTTATA 118

( 2 ) INFORMATION FOR SEQ ID NO:26:

( i ) SEQUENCE CHARACTERISTICS:
        ( A ) LENGTH: 118 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Synthetic ( i x ) FEATURE:
        ( A ) NAME/KEY: misc_feature
        ( B ) LOCATION: 1..118
        ( D ) OTHER INFORMATION: /standard_name="Oligonucleotide
            mc111"

( x i ) SEQUENCE DESCRIPTION: SEQ ID NO:26:

TATATCTAGA AAAAGCCAG CTTACCTGAG GAGACGGTGA CCAGGGTCCC TTGGCCCCAG 60

TATGCGAACC ATGCCCCGTA GTCCATCCCT CTTGCACAGT GATATAAGGC CGTGTCCT 118

( 2 ) INFORMATION FOR SEQ ID NO:27:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( i i i ) HYPOTHETICAL: NO ( i x ) FEATURE:
        ( A ) NAME/KEY: Peptide
        ( B ) LOCATION: 1..16

(D) OTHER INFORMATION: /note="First
complementarity-determining region (CDR1) of
BR55-1 antibody light chain"

(xi) SEQUENCE DESCRIPTION: SEQ ID NO:27:

Arg Ser Ser Gln Ser Ile Val His Ser Asn Gly Asn Thr Tyr Leu Glu
1               5                   10                  15

(2) INFORMATION FOR SEQ ID NO:28:

(i) SEQUENCE CHARACTERISTICS:
 (A) LENGTH: 7 amino acids
 (B) TYPE: amino acid
 (D) TOPOLOGY: linear (ii) MOLECULE TYPE: peptide (iii) HYPOTHETICAL: NO (ix) FEATURE:
 (A) NAME/KEY: Peptide
 (B) LOCATION: 1..7
 (D) OTHER INFORMATION: /note="Second
complementarity-determining region (CDR2) of
BR55-2 antibody light chain"

(xi) SEQUENCE DESCRIPTION: SEQ ID NO:28:

Lys Val Ser Asn Arg Phe Ser
1               5

(2) INFORMATION FOR SEQ ID NO:29:

(i) SEQUENCE CHARACTERISTICS:
 (A) LENGTH: 9 amino acids
 (B) TYPE: amino acid
 (D) TOPOLOGY: linear (ii) MOLECULE TYPE: peptide (iii) HYPOTHETICAL: NO (ix) FEATURE:
 (A) NAME/KEY: Peptide
 (B) LOCATION: 1..9
 (D) OTHER INFORMATION: /note="Third
complementarity-determining region (CDR3) of
BR55-2 antibody light chain"

(xi) SEQUENCE DESCRIPTION: SEQ ID NO:29:

Phe Gln Gly Ser His Val Pro Phe Thr
1               5

(2) INFORMATION FOR SEQ ID NO:30:

(i) SEQUENCE CHARACTERISTICS:
 (A) LENGTH: 5 amino acids
 (B) TYPE: amino acid
 (D) TOPOLOGY: linear (ii) MOLECULE TYPE: peptide (iii) HYPOTHETICAL: NO (ix) FEATURE:
 (A) NAME/KEY: Peptide
 (B) LOCATION: 1..5
 (D) OTHER INFORMATION: /note="First
complementarity-determining region (CDR1) of
BR55-2 antibody heavy chain"

(xi) SEQUENCE DESCRIPTION: SEQ ID NO:30:

Asp Tyr Tyr Met Tyr
1               5

(2) INFORMATION FOR SEQ ID NO:31:

(i) SEQUENCE CHARACTERISTICS:
    (A) LENGTH: 17 amino acids
    (B) TYPE: amino acid
    (D) TOPOLOGY: linear (ii) MOLECULE TYPE: peptide (iii) HYPOTHETICAL: NO (ix) FEATURE:
    (A) NAME/KEY: Peptide
    (B) LOCATION: 1..17
    (D) OTHER INFORMATION: /note="Second
        complementarity-determining region (CDR2) of
        BR55-2 antibody heavy chain"

(xi) SEQUENCE DESCRIPTION: SEQ ID NO:31:

```
Tyr Ile Ser Asn Gly Gly Gly Ser Ser His Tyr Val Asp Ser Val Lys
1               5                   10                  15
Gly
```

(2) INFORMATION FOR SEQ ID NO:32:

(i) SEQUENCE CHARACTERISTICS:
    (A) LENGTH: 10 amino acids
    (B) TYPE: amino acid
    (D) TOPOLOGY: linear (ii) MOLECULE TYPE: peptide (iii) HYPOTHETICAL: NO (ix) FEATURE:
    (A) NAME/KEY: Peptide
    (B) LOCATION: 1..10
    (D) OTHER INFORMATION: /note="Third
        complementarity-determining region (CDR3) of
        BR55-2 antibody heavy chain"

(xi) SEQUENCE DESCRIPTION: SEQ ID NO:32:

```
Gly Met Asp Tyr Gly Ala Trp Phe Ala Tyr
1               5                   10
```

We claim:

1. A humanized monoclonal antibody that recognizes the difucosyl Lewis blood group antigens Y-6 and B-7-2 comprising a humanized light chain variable region, a human light chain constant region, a humanized heavy chain variable region and a human heavy chain constant region, wherein the humanized light chain variable region has the sequence:

DIVMTQSPLS LPVTPGEPAS ISCRSSQSIV HSNGN-TYLEW YLQKPGQSPQ LLISKVSNRF SGVPDRF-SGS GSGTDFTLKI SRVEAEDVGV YYCFQGSHVP FTFGQGTKLE IK (SEQ ID NO:15)

and the humanized heavy chain variable region has the sequence:

EVQLLESGGG LVQPGGSLRL SCAASGFTFS DYY-MYWVRQA PEKRLEWVAY ISNGGGSSHY VDS-VKGRFTI SRDNSKNTLY LQMNSLRAED TALYH-CARGM DYGAWFAYWG QGTLVTVSS (SEQ ID NO:13).

2. The humanized monoclonal antibody of claim 1 wherein the human light chain constant region is a kappa chain constant region and the human heavy chain constant region is a gamma chain constant region.

3. The humanized monoclonal antibody of claim 2 wherein the gamma chain is a gamma 1 chain.

4. A fragment of the antibody of any of claims 1–3, wherein the fragment recognizes the difucosyl Lewis blood group antigens Y-6 and B-7-2.

5. A pharmaceutical composition comprising an antibody of any of claims 1–3 in a pharmaceutically acceptable carrier or diluent.

6. A pharmaceutical composition comprising a fragment of an antibody of claim 4 in a pharmaceutically acceptable carrier or diluent.

7. A humanized monoclonal antibody that recognizes the difucosyl Lewis blood group antigens Y-6 and B-7-2 comprising a humanized light chain variable region, a human light chain constant region, a humanized heavy chain variable region and a human heavy chain constant region, wherein the humanized light chain variable region has the sequence:

DIVMTQSPLS LPVTPGEPAS ISCRSSQSIV HSNGN-TYLEWYLQKPGQSPQ LLISKVSNRF SGVPDRF-SGS GSGTDFTLKI SRVEAEDVGV YYCFQGSHVP FTFGQGTKLE IK (SEQ ID NO:15)

and the humanized heavy chain variable region has the sequence:

EVQLLESGGG LVQPGGSLRL SCAASGFTFS DYY-MYWVRQA PEKRLEWVAY ISNGGGSSHY VDS-VKGRFTI SRDNAKNTLY LQMNSLRAED TALYH-CARGM DYGAWFAYWG QGTLVTVSS (SEQ ID NO:14).

8. The humanized monoclonal antibody of claim 7 wherein the human light chain constant region is a kappa chain constant region and the human heavy chain constant region is a gamma chain constant region.

9. The humanized monoclonal antibody of claim 8 wherein the gamma chain is a gamma 1 chain.

10. A fragment of the antibody of any of claims 7–9, wherein the fragment recognizes the difucosyl Lewis blood group antigens Y-6 and B-7-2.

11. A pharmaceutical composition comprising an antibody of any of claims 7–9 in a pharmaceutically acceptable carrier or diluent.

12. A pharmaceutical composition comprising a fragment of an antibody of claim 10 in a pharmaceutically acceptable carrier or diluent.

\* \* \* \* \*